(12) United States Patent
Guzman et al.

(10) Patent No.: US 8,328,808 B2
(45) Date of Patent: Dec. 11, 2012

(54) MINIMALLY INVASIVE ORTHOPAEDIC APPARATUS AND METHODS

(75) Inventors: Pamela C. Guzman, Fort Wayne, IN (US); Michael A. Wack, Warsaw, IN (US); Dale R. Schulze, Lebanon, OH (US); Gary W. Knight, West Chester, OH (US); Christopher J. Hess, Lebanon, OH (US); Rudolph H. Nobis, Mason, OH (US); Michael F. Clem, Maineville, OH (US); Ronald J. Kolata, Cincinnati, OH (US)

(73) Assignee: Biomet, C.V. (GI)

( * ) Notice: Subject to any disclaimer, the term of this patent is extended or adjusted under 35 U.S.C. 154(b) by 1233 days.

(21) Appl. No.: 10/480,053

(22) PCT Filed: May 24, 2002

(86) PCT No.: PCT/US02/16505
§ 371 (c)(1),
(2), (4) Date: Dec. 9, 2003

(87) PCT Pub. No.: WO03/002022
PCT Pub. Date: Jan. 9, 2003

(65) Prior Publication Data
US 2005/0261555 A1   Nov. 24, 2005

Related U.S. Application Data

(60) Provisional application No. 60/301,309, filed on Jun. 27, 2001.

(51) Int. Cl.
*A61B 17/56* (2006.01)
(52) U.S. Cl. .................................................. 606/68

(58) Field of Classification Search .............. 606/86, 606/96, 90, 98; 600/114
See application file for complete search history.

(56) References Cited

U.S. PATENT DOCUMENTS

| | | | |
|---|---|---|---|
| 2,494,229 A * | 1/1950 | Collison | 606/916 |
| 3,486,500 A * | 12/1969 | Ball et al. | 606/67 |
| 4,109,263 A | 8/1978 | Johnson | |
| 4,465,065 A * | 8/1984 | Gotfried | 606/65 |
| 4,541,424 A * | 9/1985 | Grosse et al. | 606/98 |
| 4,621,628 A * | 11/1986 | Brudermann | 606/97 |

(Continued)

FOREIGN PATENT DOCUMENTS

CA   2047521 A1   1/1992

(Continued)

OTHER PUBLICATIONS

Online Press Release entitled "Wright Medical Technology, Inc. Launches Minimally Invasive Bone Grafting Instrumentation", Date Unknown, 4 pages.

(Continued)

*Primary Examiner* — Alvin Stewart
*Assistant Examiner* — Mary Hoffman
(74) *Attorney, Agent, or Firm* — Harness, Dickey

(57) ABSTRACT

Apparatus (20, 120, 300) and methods for use in the performance of minimally invasive orthopedic procedures, including apparatus and methods for use in the performance of such procedures under the visualization of an endoscope (22), are herein disclosed. Such procedures include a minimally invasive intramedullary nailing procedure, a minimally invasive bone graft harvesting procedure, a minimally invasive pelvic osteotomy procedure, an orthopedic implant revision procedure, and a minimally invasive percutaneous bone plating procedure.

10 Claims, 43 Drawing Sheets

U.S. PATENT DOCUMENTS

| | | | |
|---|---|---|---|
| 4,624,243 A | | 11/1986 | Lowery et al. |
| 4,733,654 A | | 3/1988 | Marino |
| 4,815,833 A | | 3/1989 | Zobel et al. |
| 4,865,025 A | * | 9/1989 | Buzzi et al. ............... 606/96 |
| 4,881,535 A | * | 11/1989 | Sohngen ..................... 606/98 |
| 4,900,138 A | | 2/1990 | Atkinson, III et al. |
| 4,913,137 A | * | 4/1990 | Azer et al. ................. 606/64 |
| 4,917,111 A | * | 4/1990 | Pennig et al. ............... 606/97 |
| 4,919,112 A | | 4/1990 | Siegmund |
| 5,028,127 A | | 7/1991 | Spitzberg |
| 5,049,151 A | * | 9/1991 | Durham et al. ............. 606/98 |
| 5,165,387 A | | 11/1992 | Woodson |
| 5,281,224 A | * | 1/1994 | Faccioli et al. ............. 606/62 |
| 5,334,194 A | | 8/1994 | Mikhail |
| 5,359,453 A | | 10/1994 | Ning |
| 5,361,166 A | | 11/1994 | Atkinson et al. |
| 5,369,525 A | | 11/1994 | Bala et al. |
| 5,403,322 A | | 4/1995 | Herzenberg et al. |
| 5,429,641 A | * | 7/1995 | Gotfried ..................... 606/67 |
| 5,433,720 A | | 7/1995 | Faccioli et al. |
| 5,448,990 A | | 9/1995 | De Faria-Correa |
| 5,457,576 A | | 10/1995 | Atkinson et al. |
| 5,533,496 A | | 7/1996 | De Faria-Correa et al. |
| 5,665,086 A | | 9/1997 | Itoman et al. |
| 5,666,222 A | | 9/1997 | Ning |
| 5,667,480 A | | 9/1997 | Knight et al. |
| 5,701,200 A | | 12/1997 | Horton |
| 5,759,185 A | | 6/1998 | Grinberg |
| 5,797,944 A | | 8/1998 | Nobles et al. |
| 5,817,015 A | | 10/1998 | Adair |
| 5,827,172 A | | 10/1998 | Takahashi et al. |
| 5,881,195 A | | 3/1999 | Walker |
| 5,892,630 A | | 4/1999 | Broome |
| 5,897,557 A | * | 4/1999 | Chin et al. ................. 606/71 |
| 5,904,685 A | | 5/1999 | Walawalkar |
| 5,928,138 A | | 7/1999 | Knight et al. |
| 5,931,839 A | * | 8/1999 | Medoff ....................... 606/69 |
| 5,947,970 A | * | 9/1999 | Schmelzeisen et al. ...... 606/70 |
| 5,957,927 A | | 9/1999 | Magee et al. |
| 5,972,020 A | * | 10/1999 | Carpentier et al. ......... 606/208 |
| 5,980,549 A | | 11/1999 | Chin |
| 6,033,407 A | | 3/2000 | Behrens |
| 6,042,538 A | * | 3/2000 | Puskas ....................... 600/114 |
| 6,053,863 A | | 4/2000 | Chin et al. |
| 6,071,284 A | | 6/2000 | Fox |
| 6,096,044 A | * | 8/2000 | Boyd et al. ................. 606/96 |
| 6,139,489 A | | 10/2000 | Wampler et al. |
| 6,139,509 A | | 10/2000 | Yuan et al. |
| 6,171,236 B1 | | 1/2001 | Bonutti |
| 6,183,477 B1 | | 2/2001 | Pepper |
| 6,193,651 B1 | | 2/2001 | DeFonzo |
| 6,193,653 B1 | | 2/2001 | Evans et al. |
| 6,196,968 B1 | | 3/2001 | Rydin et al. |
| 6,203,557 B1 | | 3/2001 | Chin |
| 6,206,823 B1 | | 3/2001 | Kolata et al. |
| 6,206,899 B1 | | 3/2001 | Ginn |
| 6,228,024 B1 | | 5/2001 | Co et al. |
| 6,228,025 B1 | | 5/2001 | Hipps et al. |
| 6,248,100 B1 | | 6/2001 | de Toledo et al. |
| 6,248,110 B1 | | 6/2001 | Reiley et al. |

FOREIGN PATENT DOCUMENTS

| | | |
|---|---|---|
| DE | 8512040 U1 | 6/1985 |
| DE | 19914387 A1 | 10/2000 |
| DE | 200 19 026 U1 | 3/2002 |
| EP | 0 468 192 A2 | 1/1992 |
| EP | 0761171 A2 | 3/1997 |
| WO | WO 95/11632 A1 | 5/1995 |
| WO | WO 99/17661 | 4/1999 |

OTHER PUBLICATIONS

Christian Krettek (Hannover), Orthopaedic Trauma Association—Technological Advances in Trauma Care, "Minimally Invasive Plate Osteosynthesis", Date Unknown, 4 pages.

Iván Rubel et al., Osteosynthese International, "Endoscopic fixation of the symphysis pubis", 1999, vol. 7, pp. 204-208.

Mathys Medical Ltd. (Bettlach, Switzerland), Item No. 0336.078, "Less Invasive Stabilization System (LISS)—Surgical technique—Distal Femur", Jul. 1998, 28 pages.

\* cited by examiner

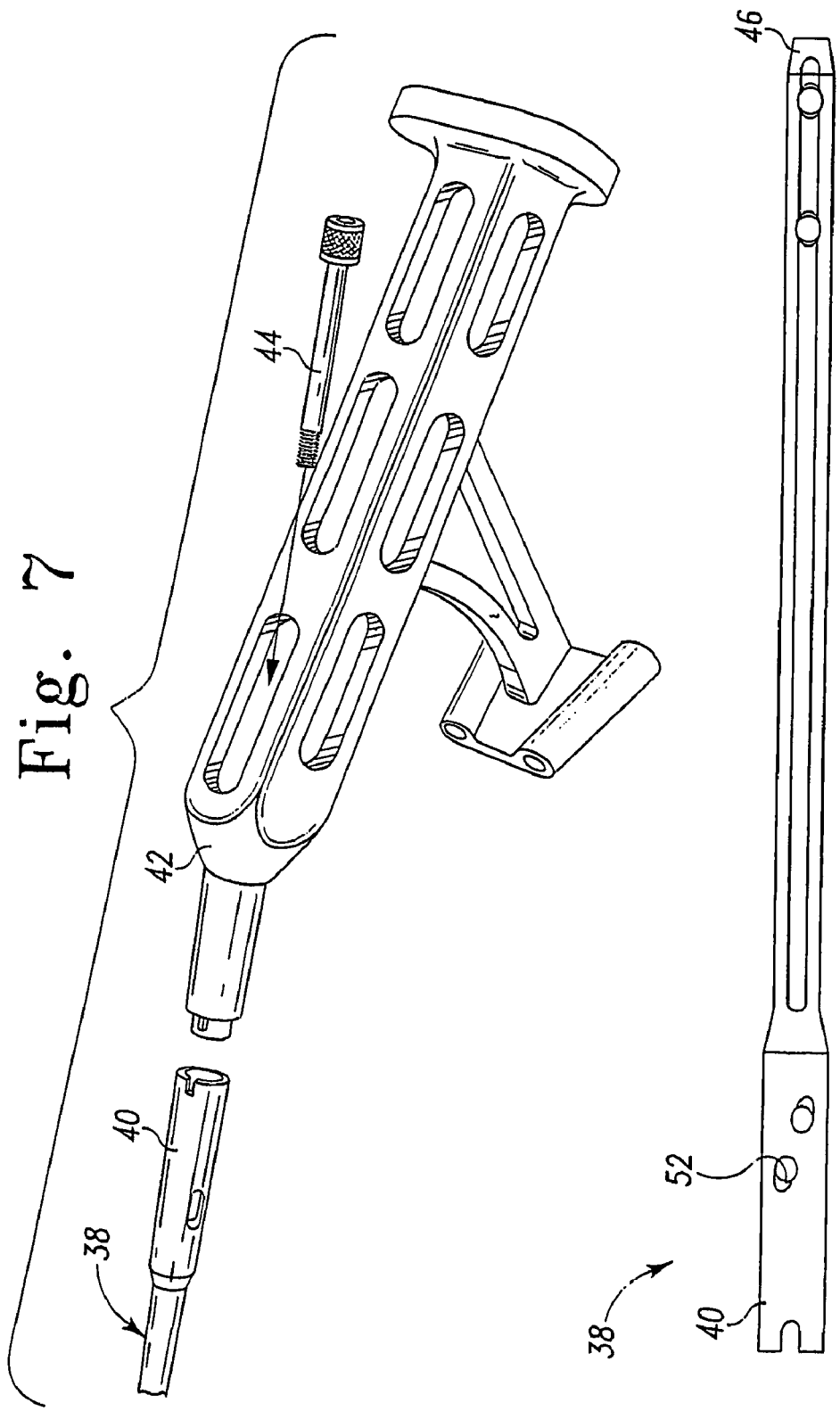

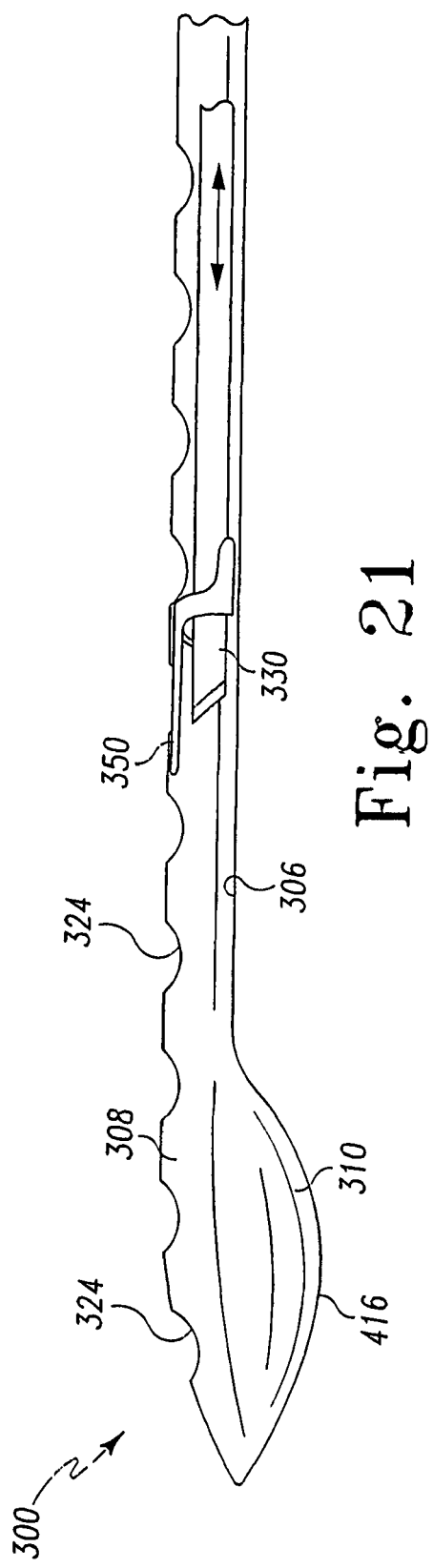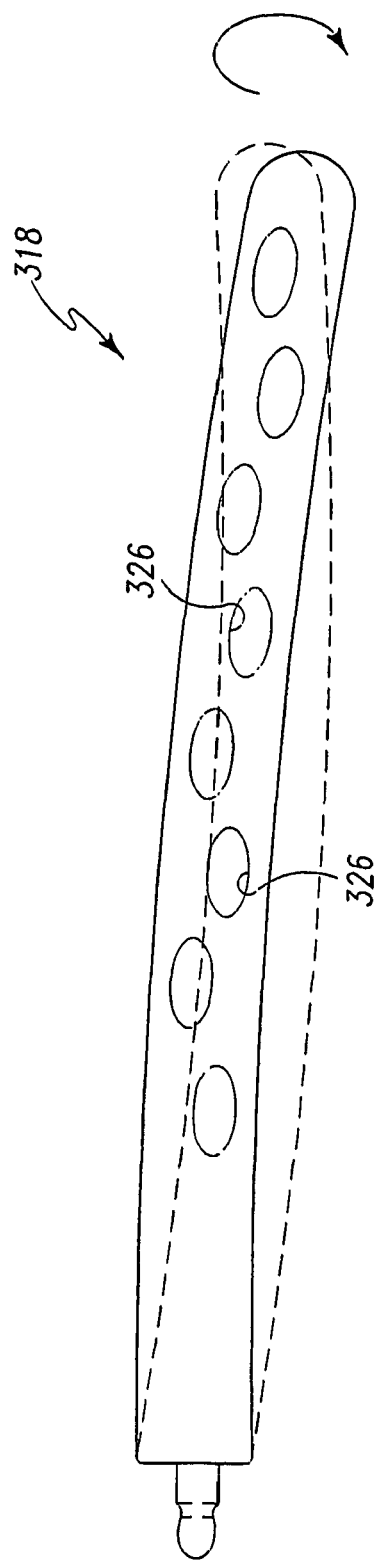
Fig. 21
Fig. 22

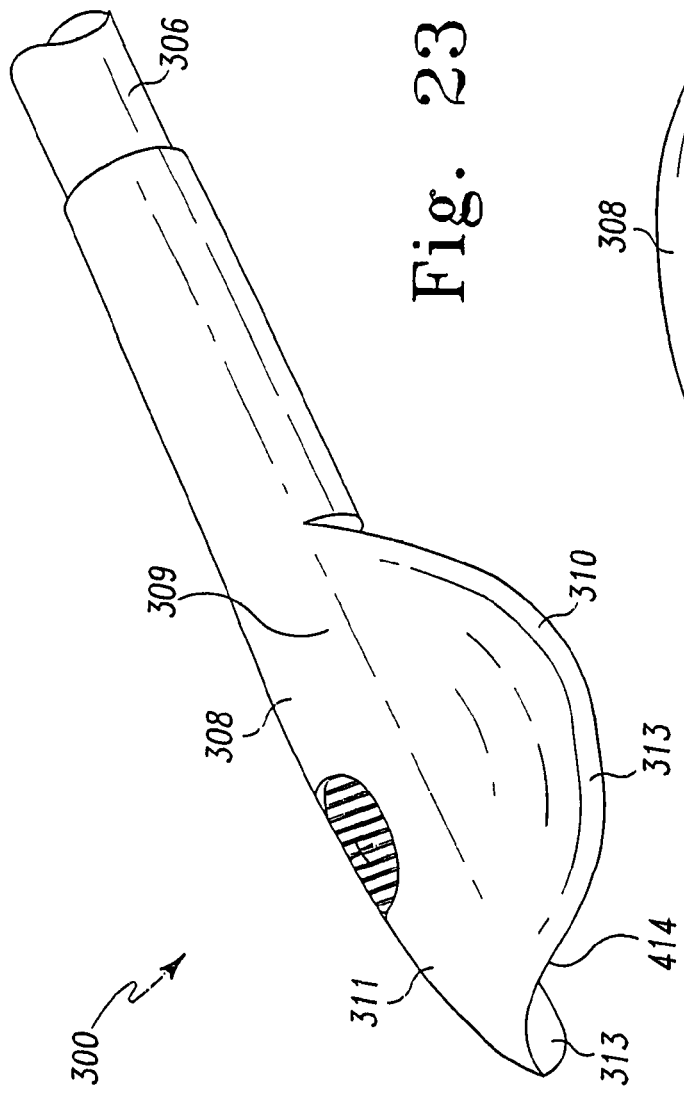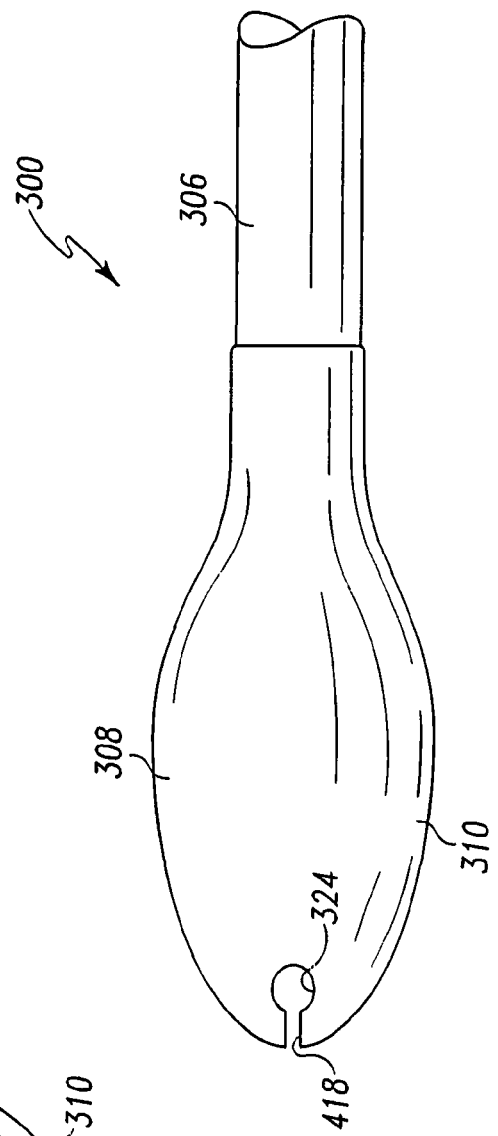

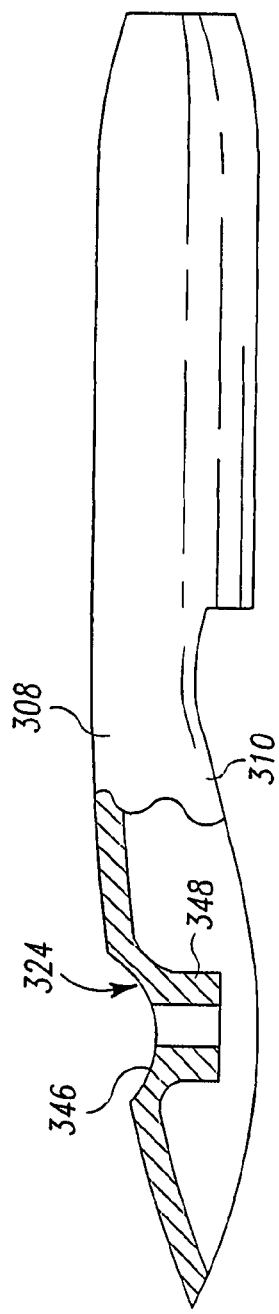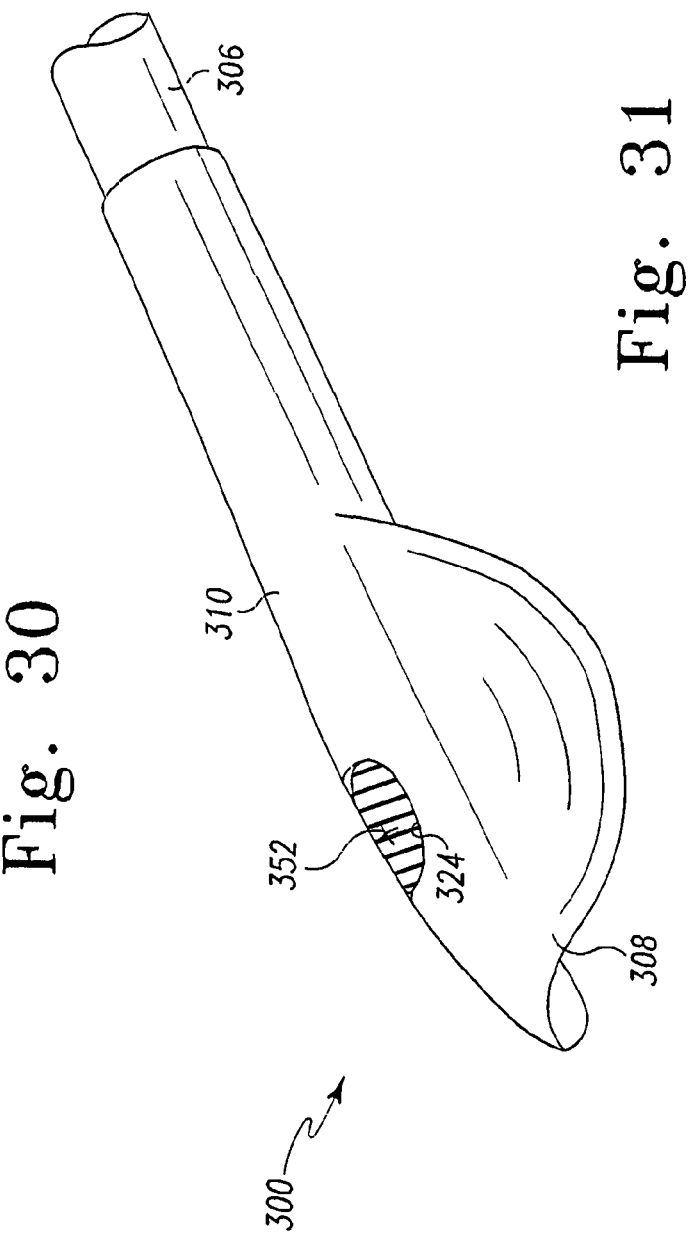
Fig. 30
Fig. 31

MINIMALLY INVASIVE ORTHOPAEDIC APPARATUS AND METHODS

This application is a U.S. national counterpart application of international application Ser. No. PCT/US02/16505 filed May 24, 2002, which claims priority to U.S. provisional application Ser. No. 60/301,309, filed Jun. 27, 2001, the entirety of both of these applications is hereby incorporated by reference.

FIELD OF THE DISCLOSURE

The present disclosure relates generally to orthopaedic methods and apparatus, and more particularly to methods and apparatus for use in the performance of endoscopic minimally invasive orthopaedic procedures.

BACKGROUND OF THE DISCLOSURE

Minimally invasive surgical techniques have been developed for many different types of surgical procedures. Such techniques attempt to balance the need to achieve the goal of the surgical procedure while minimizing the surgical injury to the patient. As such, surgeries performed by use of minimally invasive techniques generally result in lower postoperative morbidity, shorter postoperative stay, less postoperative pain, decreased cost, and quicker recovery as compared to "open" or conventional surgical techniques. Because of the aforementioned advantages, these minimally invasive techniques are being applied to an increasing variety of surgical procedures. For example, minimally invasive techniques in the form of laparoscopic procedures, such as a laparoscopic colectomy for carcinoma of the colon, have been developed.

However, despite growing use in other surgical fields, minimally invasive techniques have not been significantly developed for use in orthopaedic procedures. In particular, although orthopaedic surgeons have recognized the general principle that maintenance of soft tissue contributes significantly to the postoperative healing process, conventional techniques in which the soft tissue is completely opened in order to gain complete access to the bone structure therein are still in widespread use. One reason for this is the unique nature of many orthopaedic procedures. In particular, orthopaedic procedures often involve the "delivery" and implantation of devices which are relatively large in design compared to the "deliverables" associated with other forms of surgery. In particular, in the case of, for example, an appendectomy, minimally invasive techniques are adaptable since the surgeon may aptly remove the subject tissue (i.e., the patient's appendix) and thereafter deliver and install the necessary sutures through the relatively small confines of a cannula of a trocar. However, in the case of, for example, trauma repair of a heavily fractured long bone (e.g., a femur or tibia), one or more relatively large plates are screwed or otherwise fastened to the fractured bone. The size of such plates has long since been viewed as prohibitive in regard to the use of minimally invasive techniques for the implantation thereof.

Another reason commonly cited in regard to the use of traditional techniques (i.e., "open" incisions) is the surgeon's need to visualize the surgical site. In particular, orthopaedic procedures commonly include complicated fractures which require precision in regard to the installation of fixation devices (e.g., screws and the like) and the reduction of such fractures. As such, surgeons have heretofore preferred to open the soft tissue surrounding the bone to be treated in order to completely expose the surgical site.

As a result of such continued use of "open" procedures, soft tissue surrounding the bone continues to be compromised thereby impairing normal blood circulation to the treated bone, potentially delaying fracture healing, and potentially increasing the risk of infection. Indeed, although the majority of patients treated with such procedures heal without complication, there are certain occasions in which complications such as infection or non-union occur thereby prolonging healing rates and, in certain cases, increasing the rates of secondary revisions.

As a result of the aforedescribed shortcomings associated with traditional orthopaedic surgeries, along with the promise associated with minimally invasive techniques, a number of attempts have been made to provide certain of the advantages associated with minimally invasive techniques to a limited number of orthopaedic procedures. For example, plate fixation assemblies have heretofore been developed for use in fracture repair of femurs. However, such assemblies suffer from a number of drawbacks. For example, such assemblies rely heavily on the use of fluoroscopy as the manner by which the surgeon "visualizes" the surgical site. In addition to the fundamental limitations relating to the resolution associated with fluoroscopy, many surgeons may also be reluctant to embrace the use of large amounts of fluoroscopy in order to minimize radiation exposure to themselves, the other members of the surgical staff, and the patient.

SUMMARY OF THE DISCLOSURE

The concepts of the present disclosure provide apparatus and methods for use in the performance of minimally invasive orthopaedic procedures. The concepts of the present disclosure also provide apparatus and methods for use in the performance of such procedures under the visualization of an endoscope.

In accordance with one illustrative embodiment of the concepts of the present disclosure, there are provided apparatus and methods for use in the performance of a minimally invasive intramedullary nailing procedure. In accordance with a more specific implementation of this illustrative embodiment, there are provided apparatus and methods for use in the performance of an endoscopic minimally invasive intramedullary nailing procedure.

In accordance with another illustrative embodiment of the concepts of the present disclosure, there are provided apparatus and methods for use in the performance of a minimally invasive bone graft harvesting procedure. In accordance with a more specific implementation of this illustrative embodiment, there are provided apparatus and methods for use in the performance of an endoscopic minimally invasive bone graft harvesting procedure. There are also provided, in accordance with a more specific implementation of this illustrative embodiment, methods and apparatus for use in the performance of a minimally invasive, or even an endoscopic minimally invasive, bone graft material delivery procedure.

In accordance with another illustrative embodiment of the concepts of the present disclosure, there are provided apparatus and methods for use in the performance of a minimally invasive pelvic osteotomy procedure. In accordance with a more specific implementation of this illustrative embodiment, there are provided apparatus and methods for use in the performance of an endoscopic minimally invasive pelvic osteotomy procedure.

In accordance with another illustrative embodiment of the concepts of the present disclosure, there are provided apparatus and methods for use in the performance of an orthopaedic implant revision procedure. In accordance with a more specific implementation of this illustrative embodiment, there are provided apparatus and methods for use in the performance of an endoscopic orthopaedic implant revision procedure.

In accordance with another illustrative embodiment of the concepts of the present disclosure, there are provided apparatus and methods for use in the performance of a minimally invasive percutaneous bone plating procedure. In accordance with a more specific implementation of this illustrative embodiment, there are provided apparatus and methods for use in the performance of an endoscopic minimally invasive percutaneous bone plating procedure.

BRIEF DESCRIPTION OF THE DRAWINGS

FIG. 6 is a plan view of an intramedullary nail;

FIG. 7 is an exploded fragmentary perspective view which shows the nail of FIG. 6 being secured to a jig;

FIG. 21 is a fragmentary diagrammatic side elevational view of a plating instrument which shows a remotely controllable hole cover;

FIG. 22 is a plan view of a rotatable screw alignment device;

FIG. 23 is a fragmentary perspective view which shows a spoon having a leading edge which is configured to conform to the contour of a fractured bone;

FIG. 24 is a plan view of a spoon which has a slot defined therein;

FIG. 30 is a fragmentary cross sectional view of the spoon;

FIG. 31 is a fragmentary perspective view of the spoon which shows a seal covering the hole in the spoon;

DETAILED DESCRIPTION OF ILLUSTRATIVE EMBODIMENTS

Figure 1:
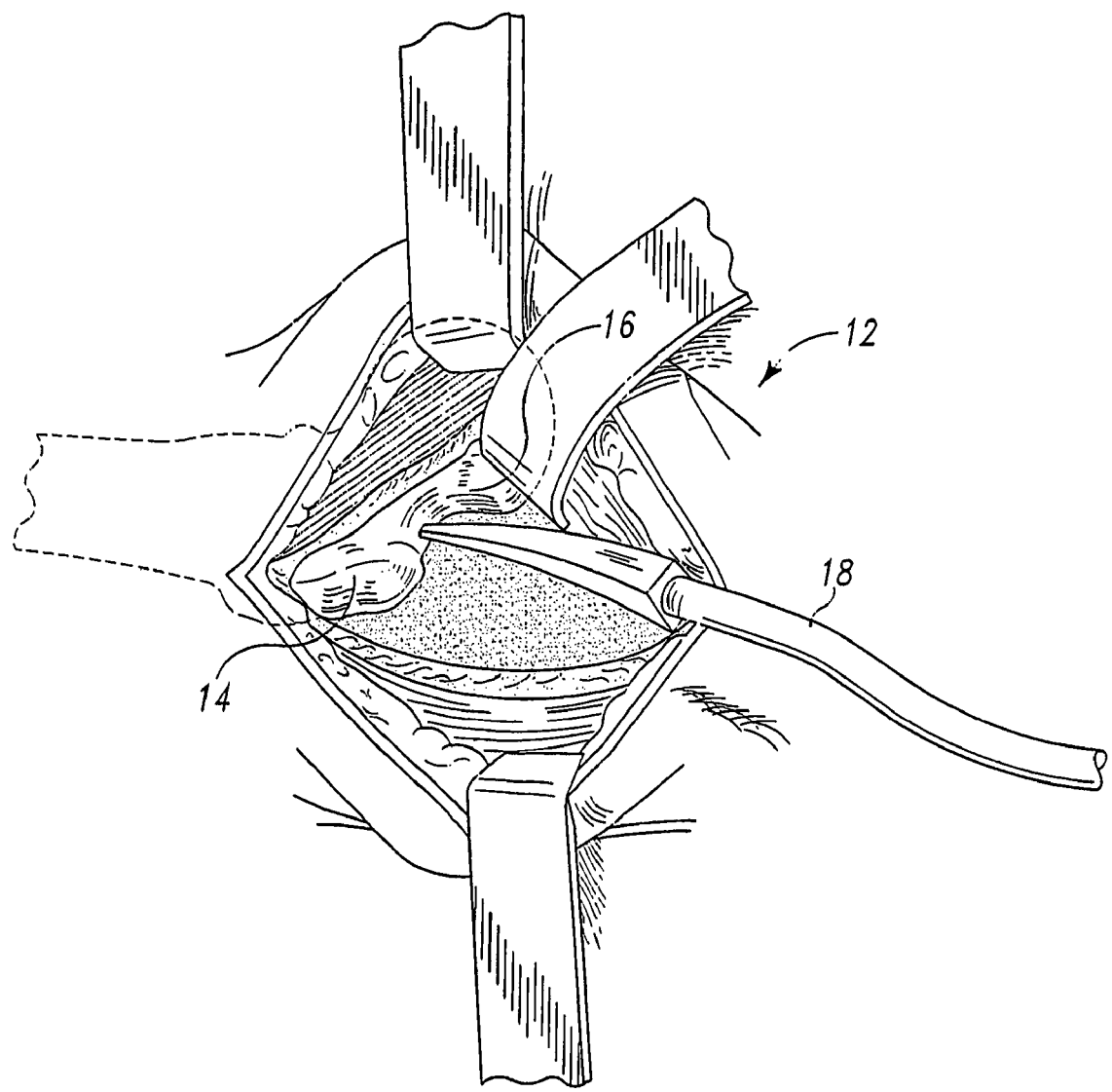
FIG. 1 is a perspective view of a surgical site utilizing a prior art intramedullary nailing technique.

While the concepts of the present disclosure are susceptible to various modifications and alternative forms, specific embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure.

Figure 53:
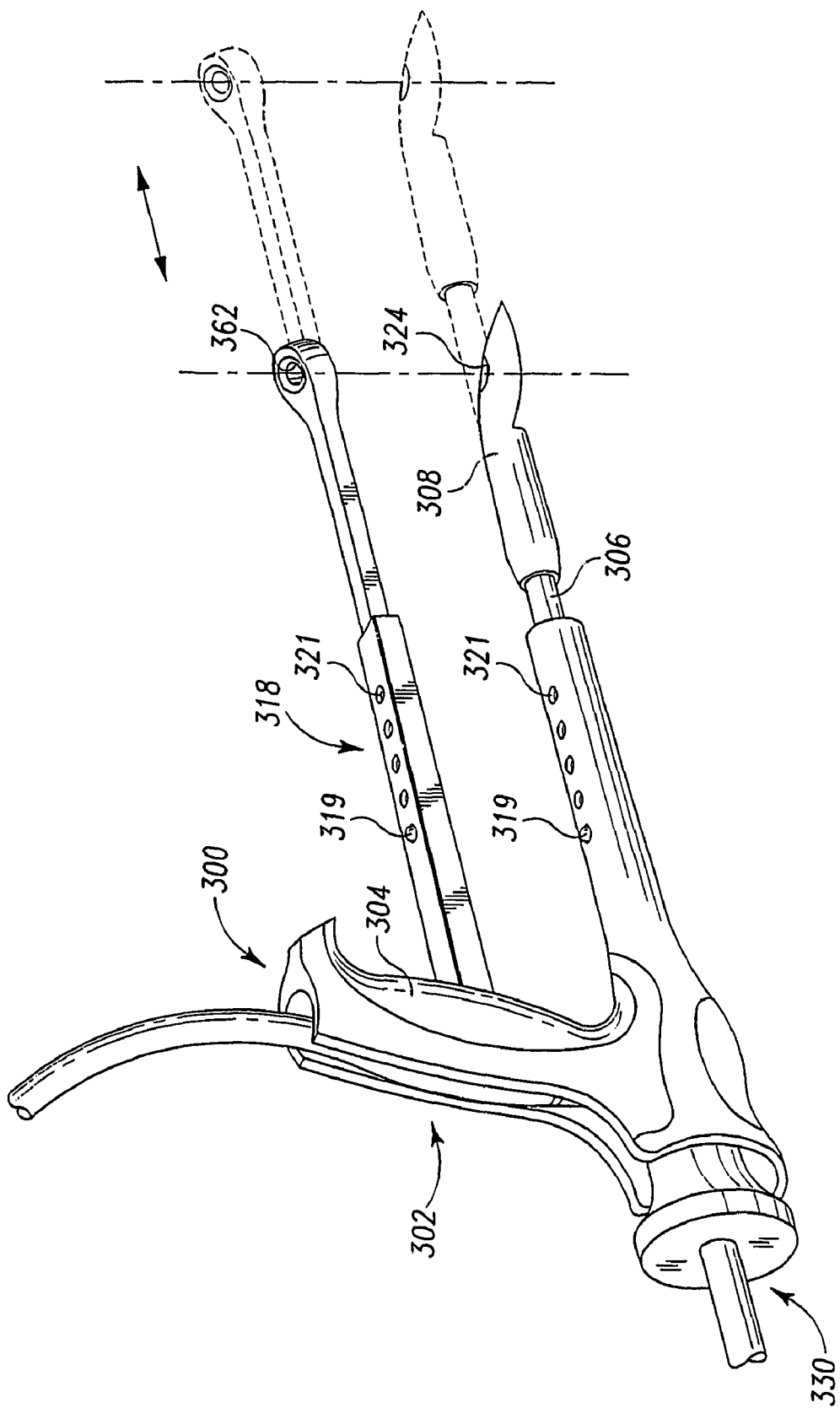
FIG. 53 is a perspective view of a plating instrument having a telescoping tissue expander and screw alignment device.

Referring now to FIGS. 1-53, there is shown a number of apparatus and methods which may be utilized to perform a minimally invasive orthopaedic surgical procedure. Common to many of the concepts disclosed herein is the notion of utilizing endoscopic instruments to provide the surgeon with enhanced viewing capabilities in the form of direct visualization of the surgical site. The concepts of the present disclosure may be utilized in a wide variety of orthopaedic procedures. Indeed, although the concepts of the present disclosure will be described in regard to specific orthopaedic procedures, it should be appreciated that such concepts are not limited to the specific exemplary embodiments described herein, but rather may be utilized in a wide variety of orthopaedic procedures.

Endoscopes

As utilized herein, the term "endoscope" is intended to mean any device which is capable of collecting images for display on a display device. As such, the endoscopes of the present disclosure may take the form of a conventional endoscopic "wand" which utilizes conventional endoscopic imaging techniques. Conventional endoscopes are constructed such that an objective lens and an eyepiece are disposed at opposite end portions of optical fibers for transmitting an image. The image of an article to be observed is made to focus at one end face of the optical fibers. A transmitted image of the article is transmitted through the optical fibers and appears on the other end face so as to be observed through the eyepiece.

More recently, endoscopes have been constructed in which an image sensor converts an optical image focused on the sensor into electrical signals. The image sensor typically includes an array of light detecting elements in which each element produces a signal corresponding to the intensity of light impinging on the element when an image is focused on the array. These signals may then be used, for example, to display a corresponding image on a monitor or otherwise used to provide information about the optical image. One common type of image sensor is a charged coupled device (CCD). CCDs have been improved greatly during the last several years, and, as a result, provide images with very good resolution.

Another type of image sensor is formed as an integrated circuit using a complementary metal oxide semiconductor (CMOS) process. In such a CMOS type image sensor, a photodiode or phototransistor (or other suitable device) is used as the light-detecting element in which the conductivity of the element corresponds to the intensity of light impinging on the element. The variable signal thus generated by the light-detecting element is an analog signal whose magnitude is approximately proportional (within a certain range) to the amount of light impinging on the element. Examples of medical devices using a CMOS chip are provided in U.S. Pat. No. 5,817,015 issued to Adair on Oct. 6, 1998 and U.S. Pat. No. 6,139,489 issued to Wampler et al. on Oct. 31, 2000, both of which are hereby incorporated herein by reference.

It is known to form these light-detecting elements in a two-dimensional core array that is addressable by row and column. Once a row of elements has been addressed, the analog signals from each of the light detecting elements in the row are coupled to the respective columns in the array. In some CMOS based systems, an analog-to-digital (A/D) converter may then be used to convert the analog signals on the columns to digital signals so as to provide only digital signals at the output of the image sensor chip. These signals may then be transmitted to a video display for viewing of the image. Examples of this type of video format include the PAL format commonly used for European televisions, and the high resolution S-video format used in, for example, surgical operating rooms. Indeed, most CCD based endoscopic systems also use the S-video format.

Other CMOS based systems send an analog signal to the video display. An example of this type of format is the NTSC format such as the format used for standard television signals in the United States. The latter is a very popular format, therefore, for CMOS based systems, due to the huge number of NTSC formatted televisions available.

CMOS image sensors are generally highly sensitive to light. As a result, the light intensity required to illuminate the image when using a CMOS system (typically less than or equal to one lux) is relatively low. In fact, a very low power light source, such as a tungsten filament, incandescent, penlight bulb, placed near the area being imaged, or used within a short distance of a light transmitting element such as an acrylic rod, is sufficient for the CMOS system to obtain a good image. The low power light source and transmitting element are small enough to be placed inside of a handheld, endoscopic medical instrument. Moreover, CMOS image sensors require very little electrical power and it is practical to use small (in the range of 6-9 VDC) batteries to operate them, although a CMOS image sensor can also be used with a conventional DC power supply connected to a wall outlet.

From the foregoing discussion, it is evident that a CMOS based visualization system may provide a disposable, low cost, high resolution, wireless system. Indeed, one or both the light source and the power source can be integrated into a handheld instrument to operate the CMOS image sensor constructed into the viewing end of the instrument. The output signal of the CMOS image sensor could then be connected to any one of a number of video displays, including conventional televisions or monitors, depending on the video format chosen. Alternatively, the output signal of the CMOS image sensor may be coupled to a "heads up" display such as a commercially available heads up display unit being offered by, amongst others, Sony Corporation.

In any of the above described cases, the image collecting unit (e.g., the camera) may be fixed in position or steerable. Moreover, illumination for operating any of the aforedescribed endoscopes may be provided by the use of commercially available LED's, tungsten bulbs, or a light pipe with an illumination source mounted in the handle or externally to the device. Illumination may also be provided in conventional manners. In the case of when a CMOS pinhole camera is used, the illumination source may be infrared LED's.

Moreover, in the case of utilizing an endoscope to visualize the advancement of an obturator of a trocar, a number of different configurations are available for use in regard to the concepts of the present disclosure. For example, a separate, independent endoscope may be utilized which peers through or even around the tip of the obturator. Alternatively, the endoscope may be integrated into the clear tip of the obturator itself. Examples of an integrated endoscope and obturator are shown in U.S. Pat. No. 5,797,944 which was issued to Nobles et al. on Aug. 25, 1998, and which is hereby incorporated herein by reference.

Intramedullary Nailing

In one exemplary embodiment of the concepts of the present disclosure, an apparatus and method are provided to allow a surgeon to perform an intramedullary nailing procedure. This concept will be described herein in regard to the nailing of a patient's femur, although it should be appreciated that the concepts of the present disclosure may be utilized in regard to the nailing of other bone structures. For example, the concepts described herein may also be utilized to install intramedullary nails in a tibia or a humerus or supracondylar nails in a distal femur. As will now be discussed in regard to the installation of an intramedullary nail into the intramedullary canal of a femur, the concepts of the present disclosure allow for such installation of intramedullary nails without the use of a large, open incision and without the use of fluoroscopy.

Heretofore utilized intramedullary femoral nailing techniques required the "filleting" of the patient's hip 12 to expose the greater trochanter 14 of the femur 16 (see FIG. 1). Such filleting of the patient's hip 12 provides the surgeon with direct visualization of the proximal end of the femur 16. Thereafter, such heretofore utilized techniques require that an awl 18 or other type of instrument be placed on the femur 16 at the approximate entry point for a guide pin (not shown) which is used in the installation of the intramedullary nail. To confirm that the awl 18 is at the proper entry point of the guide pin (i.e., a point on the femur 16 adjacent to the greater trochanter 14 at the lateral edge of the piriformis fossa), a number of intraoperative anterior-posterior and lateral radiographs are taken for use by the surgeon.

Figure 2:
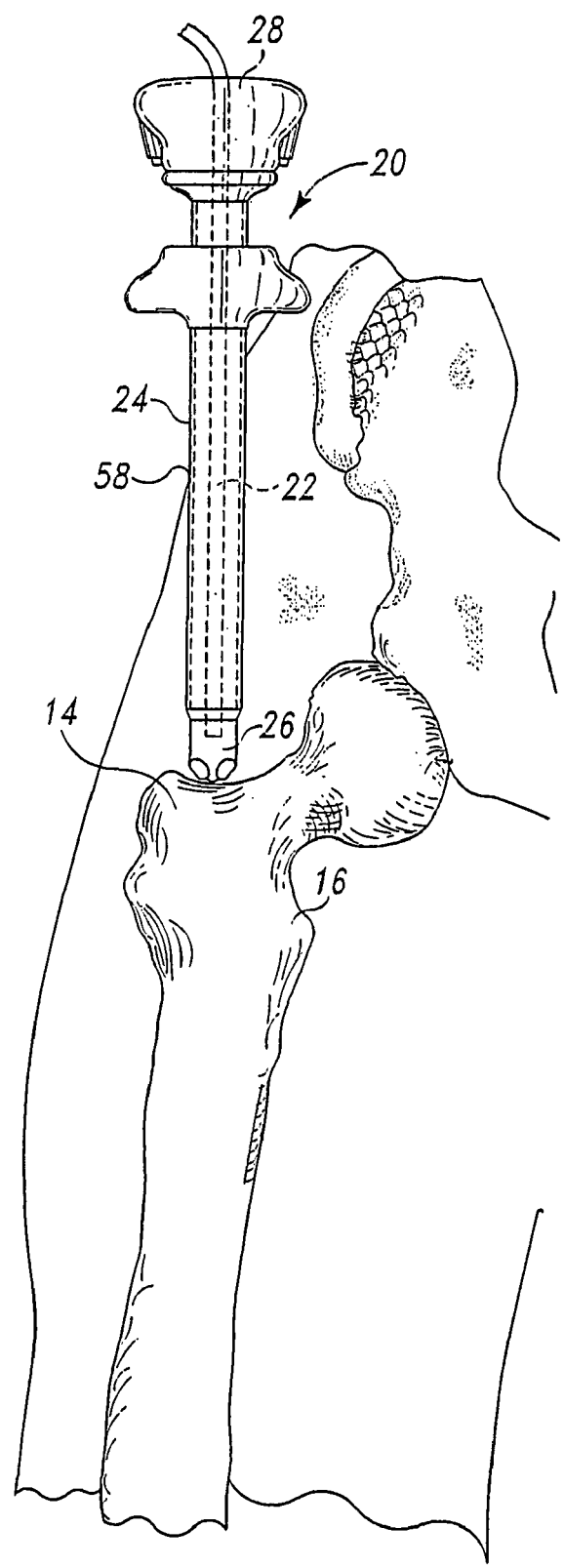
FIG. 2 is a diagrammatic view which shows a trocar being advanced to a nail entry point on the proximal femur.

However, procedures utilizing certain of the concepts of the present disclosure avoid such filleting of the hip 12 and the use of radiographs. In particular, according to one illustrative embodiment of this concept, an endoscopic instrument may be utilized by the surgeon to directly visualize the entry point for the guide pin. In a more specific illustrative embodiment, as shown in FIG. 2, a cannulated instrument such as a trocar 20 is inserted through a small stab incision 58 in the skin of the patient. The trocar 20 has an endoscope 22 associated therewith. In one exemplary embodiment, the endoscope 22 is positioned in the cannula 24. In such an arrangement, the endoscope 22 may be of conventional design and is positioned to visualize through a clear tip 26 of an obturator 28 associated with the trocar 20. However, it should be appreciated that other configurations of the endoscope 22 are also contemplated. For example, the endoscope 22 may be secured to an outer portion of the cannula 24 of the trocar 20 or may be integrated into the tip 26 of the obturator 28.

Under visualization, the tip 26 of the obturator 28 is advanced through the underlying tissue to a location on the proximal end of the femur 16 adjacent to the greater trochanter 14, as shown in FIG. 2. As such, the surgeon may utilize the images generated and returned from the endoscope 22 to position the tip 26 of the obturator 28 on the desired entry point for a guide pin. The surgeon may then remove the obturator 28 from the cannula 24 of the trocar 20.

Figure 3:
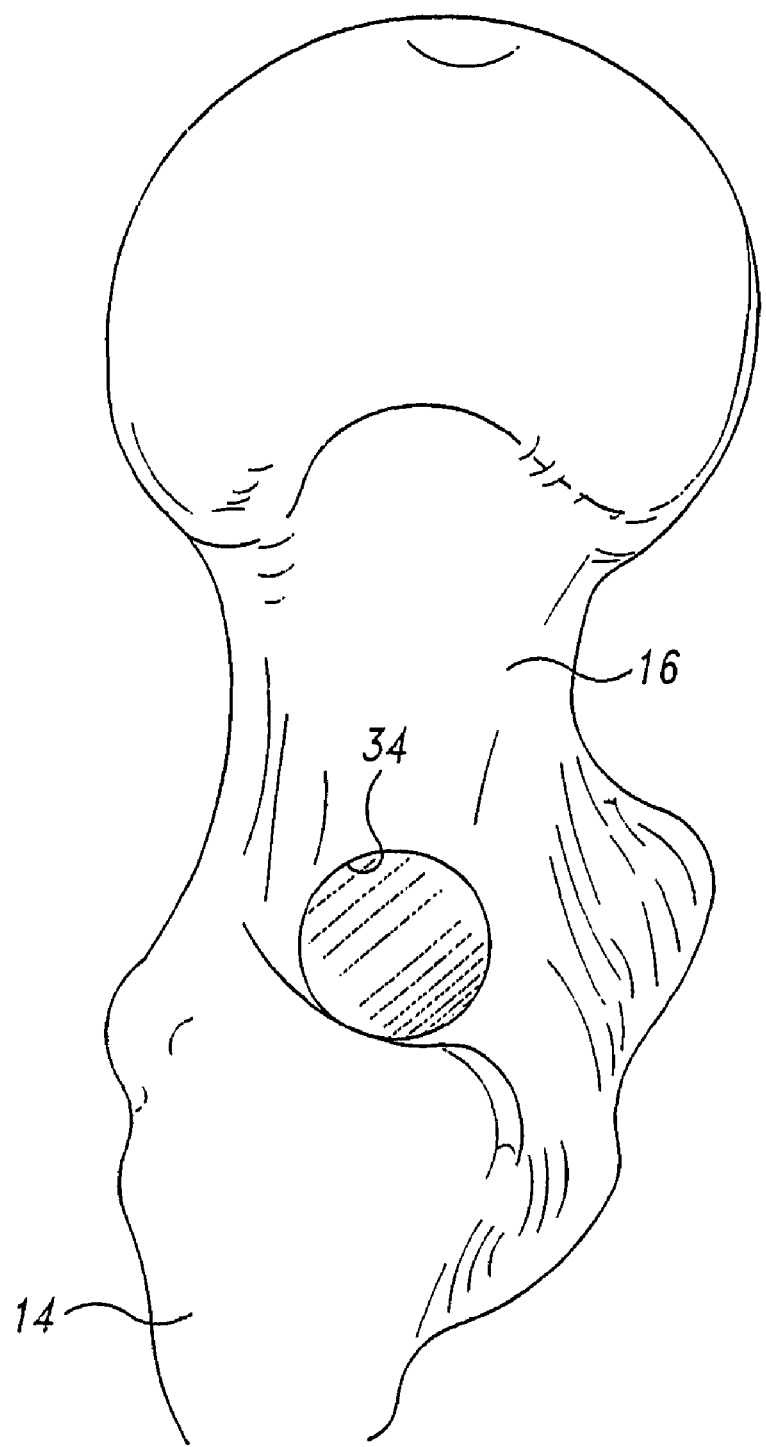
FIG. 3 is a proximal view of a prepared femur.
Figure 4:
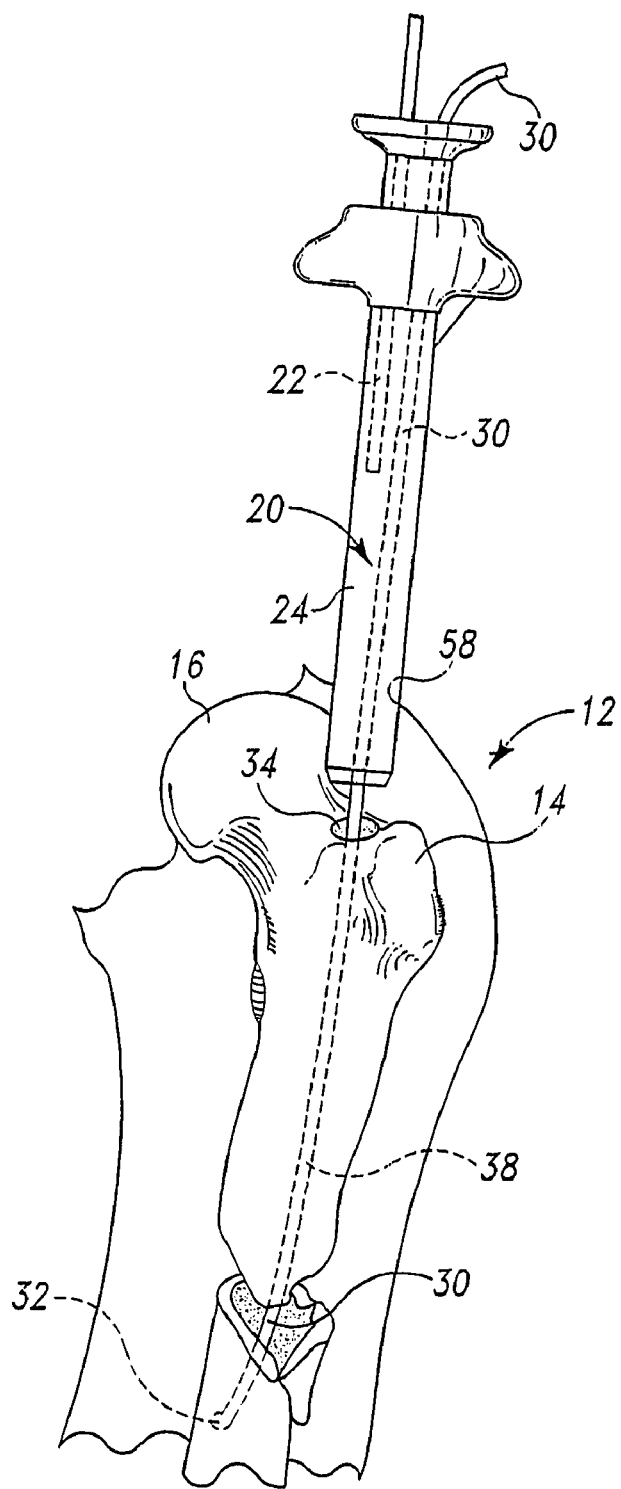
FIG. 4 is a diagrammatic perspective view which shows a guide pin being advanced into a prepared proximal femur.

Once the obturator 28 has been removed, the surgeon may then advance instruments through the cannula 24, such as an awl or step drill (not shown), to prepare the femur 16 for the introduction of a guide pin 30. The prepared femur 16 is shown in FIG. 3. Thereafter, as shown in FIG. 4, the guide pin 30 is advanced through the cannula 24 of the trocar 20 until the distal tip 32 thereof approaches the prepared hole 34 in the femur 16. The tip 32 of the guide pin 30 is then advanced under visualization provided by the endoscope 22. Specifically, the images of the prepared entry point (i.e., the hole 34) of the femur 16 collected by the endoscope 22 are utilized by the surgeon to aid the advancement of the distal tip 32 of the guide pin 30 into the hole 34 prepared in the femur 16.

Figure 5:
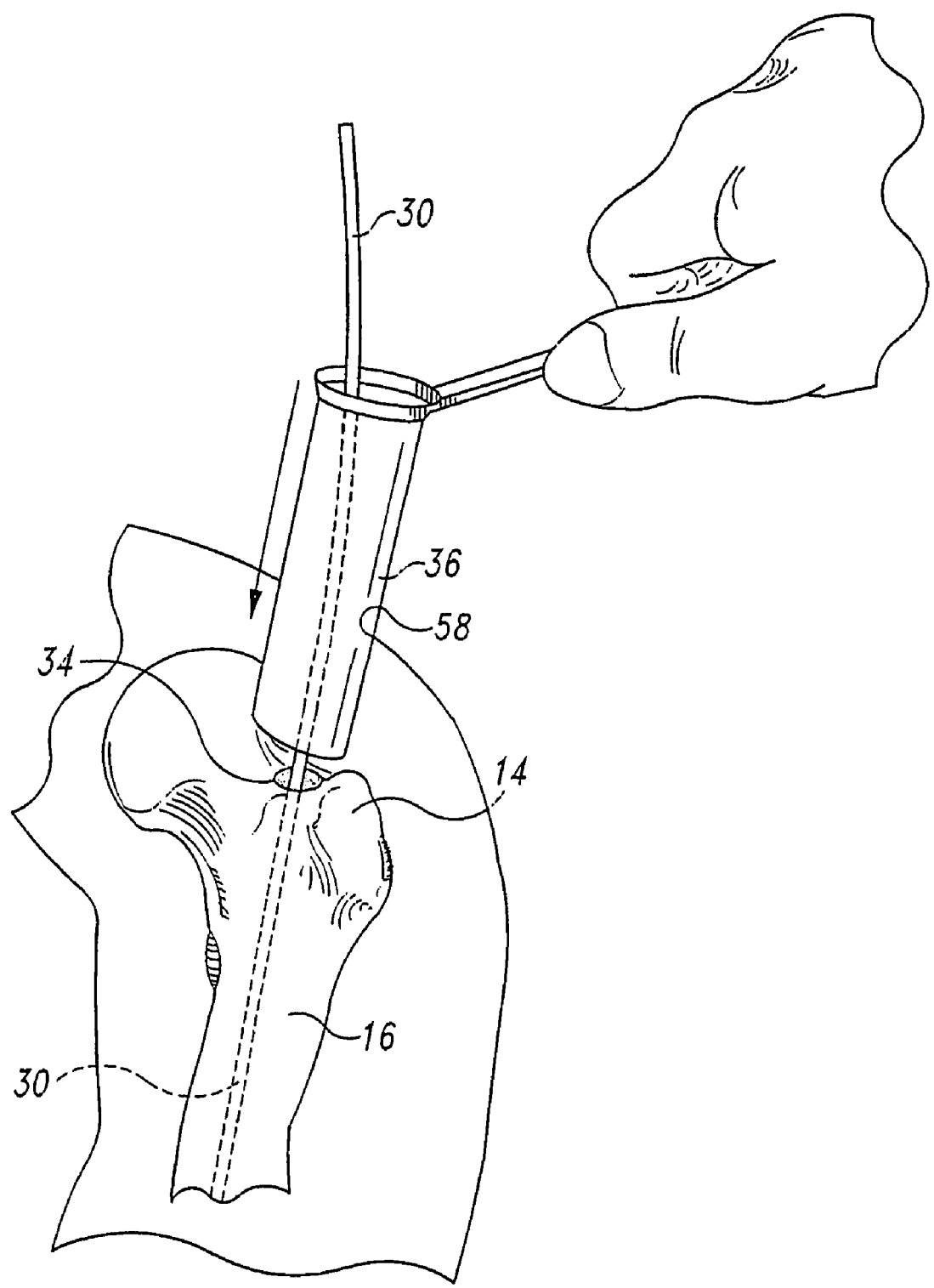
FIG. 5 is a diagrammatic perspective view which shows the installation of a tubular-shaped skin protector.

Once the guide pin 30 has been inserted into the femur 16, the nailing procedure may be completed. Specifically, the cannula 24 may be removed so that a tubular shaped skin protector 36 may be slipped over the guide pin 30 and thereafter inserted through the incision 58 in the skin. The skin protector 36 is then advanced through the underlying tissue to a position proximate to the entry point of the guide pin 30 into the femur 16, as shown in FIG. 5. During such advancement of skin protector 36, the skin, along with the underlying tissue, is spread slightly in order to protect the same during subsequent implantation of a cannulated intramedullary nail 38. Once the skin protector 36 is secured in place, the distal tip 46 of the nail 38 (see FIG. 6) may be advanced into the prepared hole 34 in the proximal end of the femur 16.

Figure 8:
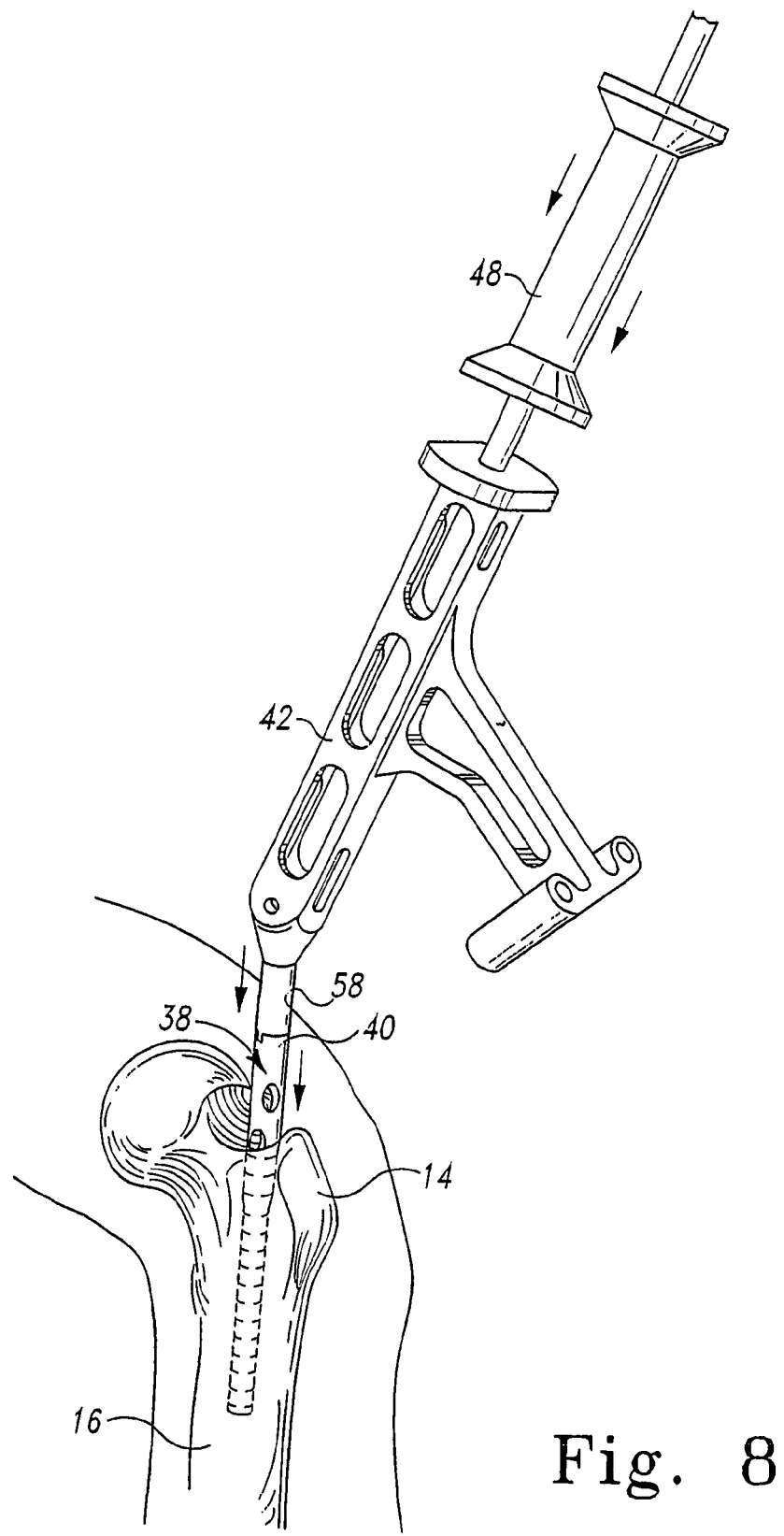
FIG. 8 is a diagrammatic perspective view which shows the nail being implanted into the proximal femur.

To do so, the nail 38 is first secured to a jig 42. Specifically, as shown in FIG. 7, a locking bolt 44 is utilized to threadingly engage a proximal end 40 of the nail 38. Once secured in such a manner, the distal tip 46 of the nail 38 is advanced into the prepared hole 34 in the proximal end of the femur 16. Thereafter, a sliding hammer 48 may be utilized to drive the nail 38 into the intramedullary canal of the femur 16 to a desired depth, as shown in FIG. 8.

Figure 9:
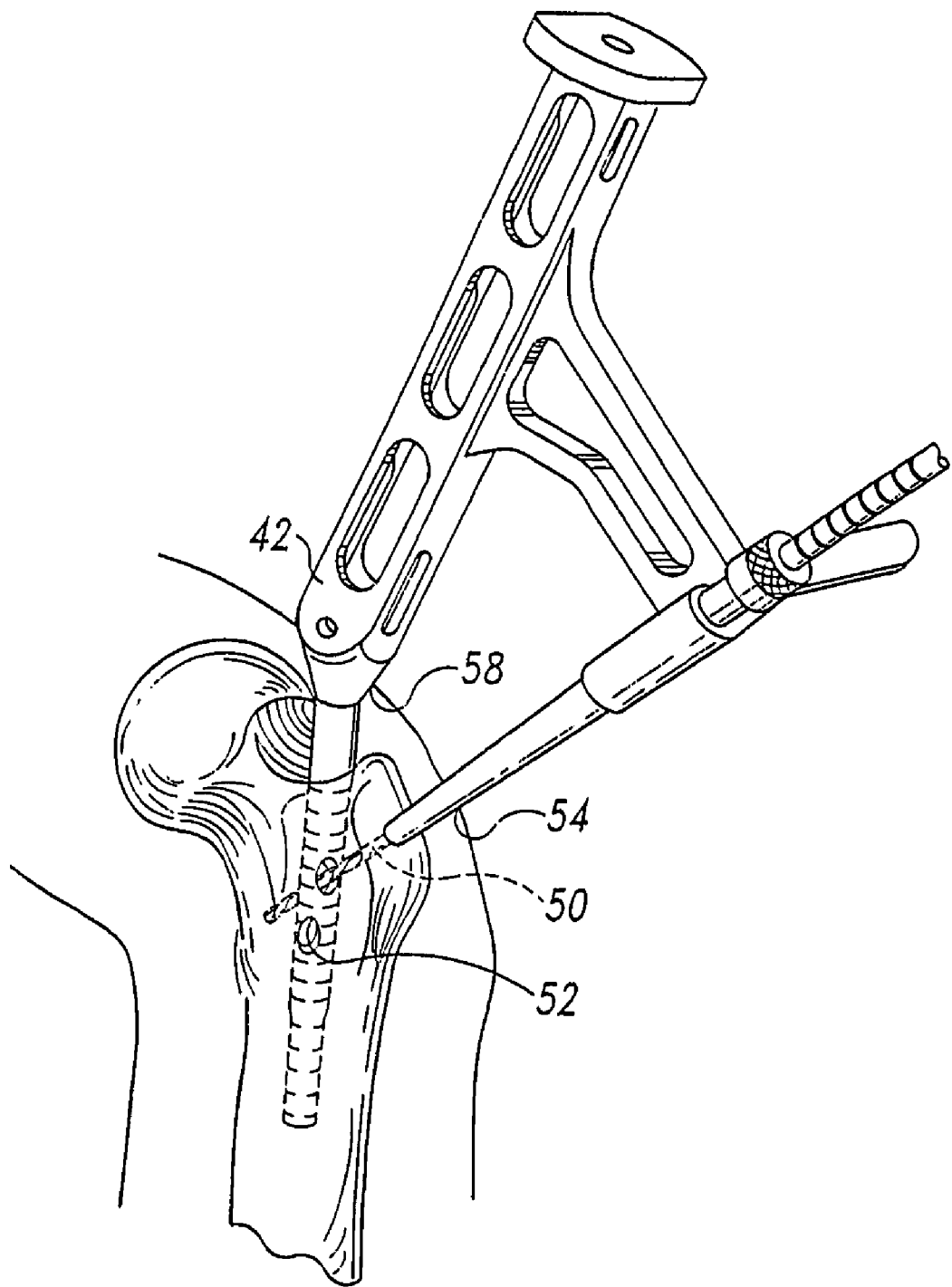
FIG. 9 is a diagrammatic perspective view which shows the installation of a number of cortical screws into the implanted nail.

As shown in FIG. 9, the jig 42 may then be utilized to guide the placement of a number of cortical screws 50 into a number of holes 52 defined in the proximal end 40 of the implanted nail 38. The screws 50 are advanced through a number of stab incisions 54 created in the skin of the patient. It should be appreciated that a number of such cortical screws may also be installed in similar holes located on the distal end of the implanted nail 38.

Figure 10:
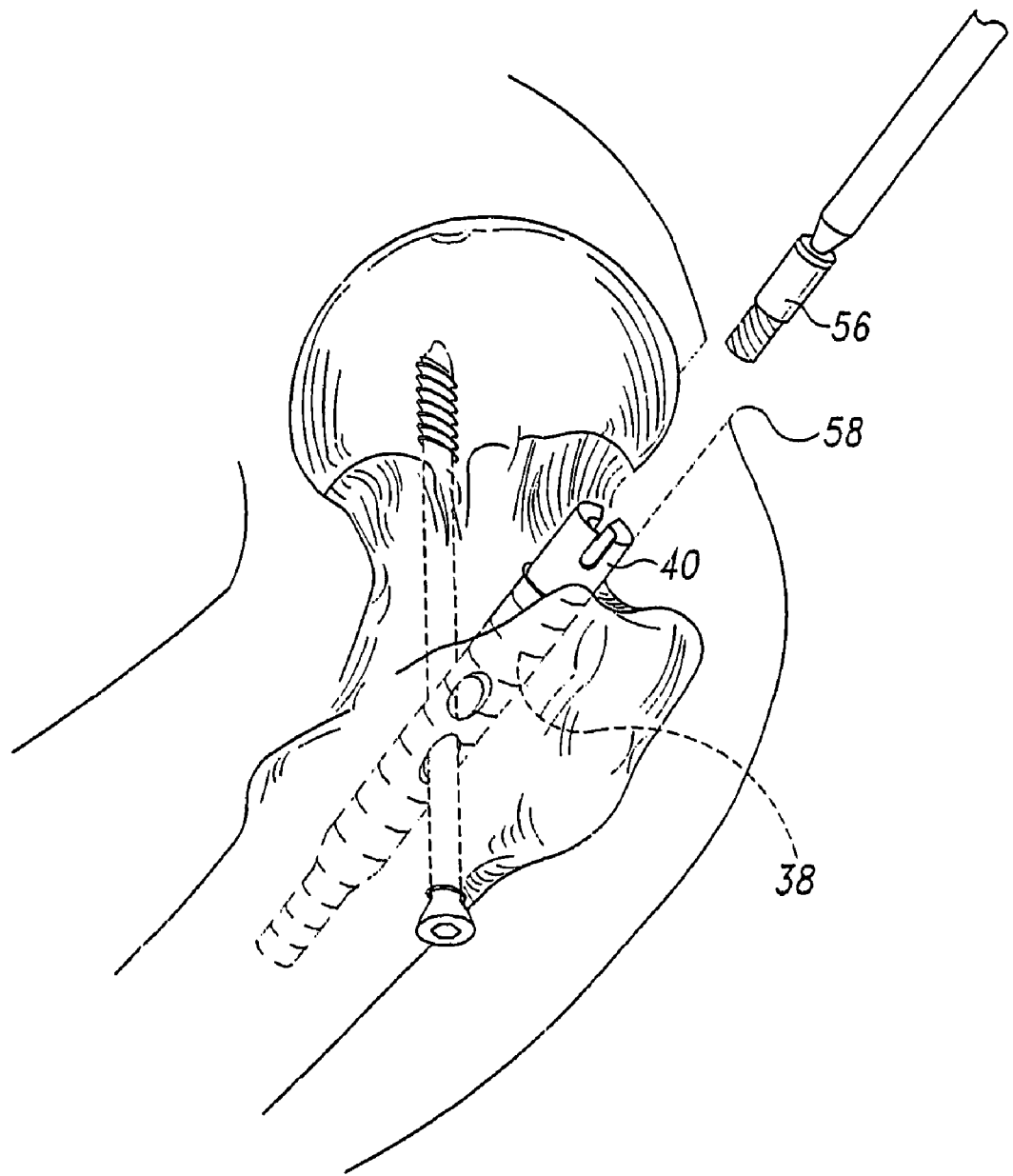
FIG. 10 is a diagrammatic perspective view which shows the installation of an end cap into the implanted nail.

As shown in FIG. 10, the jig 42 may then be removed by removal of the locking bolt 44. An end cap 56 may then be advanced through the incision 58 and thereafter screwed or otherwise secured to the proximal end 40 of the implanted nail 38. Installation of the end cap 56 prevents bony ingrowth into the threads of the proximal end 40 of the implanted nail thereby facilitating subsequent removal of the nail 38 after the femur 16 has healed.

Bone Harvesting and Delivery

In another exemplary embodiment of the concepts of the present disclosure, an apparatus and method are provided to allow a surgeon to harvest bone graft material along with the subsequent delivery of the same. This concept will be described herein in regard to the harvesting of bone graft material from the anterior surface of the patient's ilium, although it should be appreciated that the concepts of the present disclosure may be utilized in regard to the harvesting of bone graft material from other bone structures. For example, the concepts described herein may also be utilized to harvest bone graft material from the posteriorsuperior iliac spine of the ilium, a bicortical graft from the anterior aspect of the ilium, the styloid of the radius, the olecranon, the anterior aspect of the greater trochanter, the distal femoral condyle, the proximal tibia, and the distal tibia.

In regard to the specific exemplary embodiment of harvesting of bone graft material from the anterior surface of the patient's ilium, the concepts of the present disclosure allow for such bone harvesting without the use of a large, painful, open incision. In particular, heretofore utilized iliac harvesting techniques have required the filleting of the patient. Specifically, the surgeon cuts a large curvilinear incision along a path that is parallel to the iliac crest. Thereafter, the surgeon must subperiosteally dissect the abdominal musculature and, subsequently, the iliacus from the inner wall of the ilium. The bone graft material is then harvested from the ilium. Once the harvest is complete, the surgical site is closed and sutured.

An improvement to such a technique has been a long felt need. In particular, it has been noted that many patients observe significantly greater amounts of postoperative discomfort (i.e., pain), and are subjected to a significantly longer recovery period, as a result of the harvesting procedure than is generally attributable to the underlying ailment for which the patient is treated (i.e., the ailment at the site of the bone graft delivery).

Figure 11:
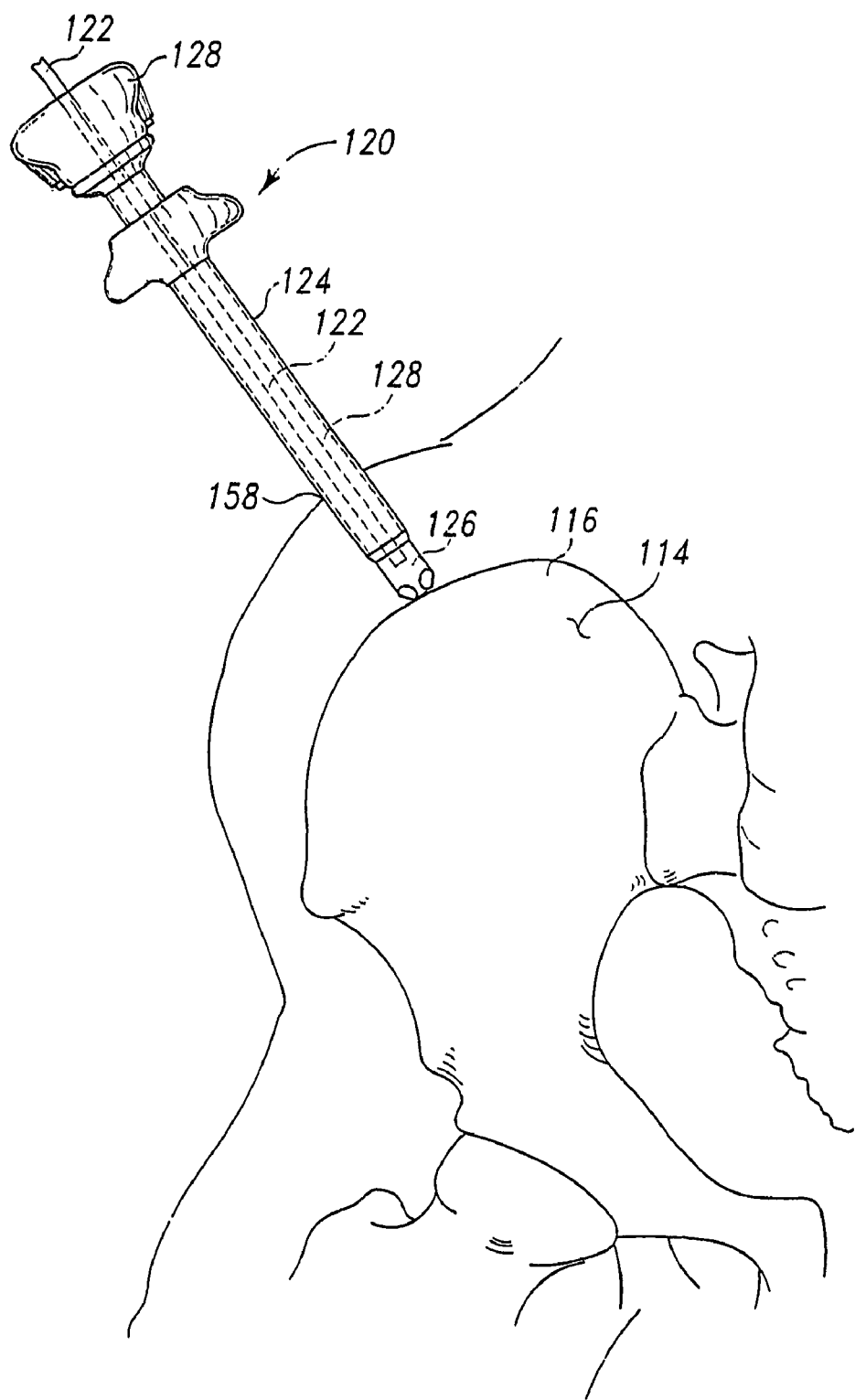
FIG. 11 is a diagrammatic perspective view which shows a trocar being advanced to a bone graft harvesting location on the ilium.

In one illustrative embodiment of the concepts of the present disclosure, an endoscopic instrument may be utilized by the surgeon to directly visualize the harvest location of the anterior surface 114 of the ilium 116. In a more specific illustrative embodiment, as shown in FIG. 11, a cannulated instrument such as a trocar 120 is inserted through a small stab incision 158 in the skin of the patient. The trocar 120 has an endoscope 122 associated therewith. In one exemplary embodiment, the endoscope 122 is positioned in the cannula 124 of the trocar 120. In such an arrangement, the endoscope 122 may be of conventional design and is positioned to visualize through a clear tip 126 of an obturator 128 associated with the trocar 120. However, it should be appreciated that other configurations of the endoscope 122 are also contemplated. For example, the endoscope 122 may be secured to an outer portion of the cannula 124 of the trocar 120, or, alternatively, may be integrated into the tip 126 of the obturator 128.

Under visualization, the tip 126 of the trocar 120 is advanced through the underlying tissue to a location proximate to the anterior surface 114 of the ilium 116, as shown in FIG. 11. As such, the surgeon may utilize the images generated and returned from the endoscope 122 to position the tip 126 of the obturator 128 proximate to the desired harvesting location of the ilium 116. The surgeon may then remove the obturator 128 from the cannula 124 of the trocar 120.

Figure 12:
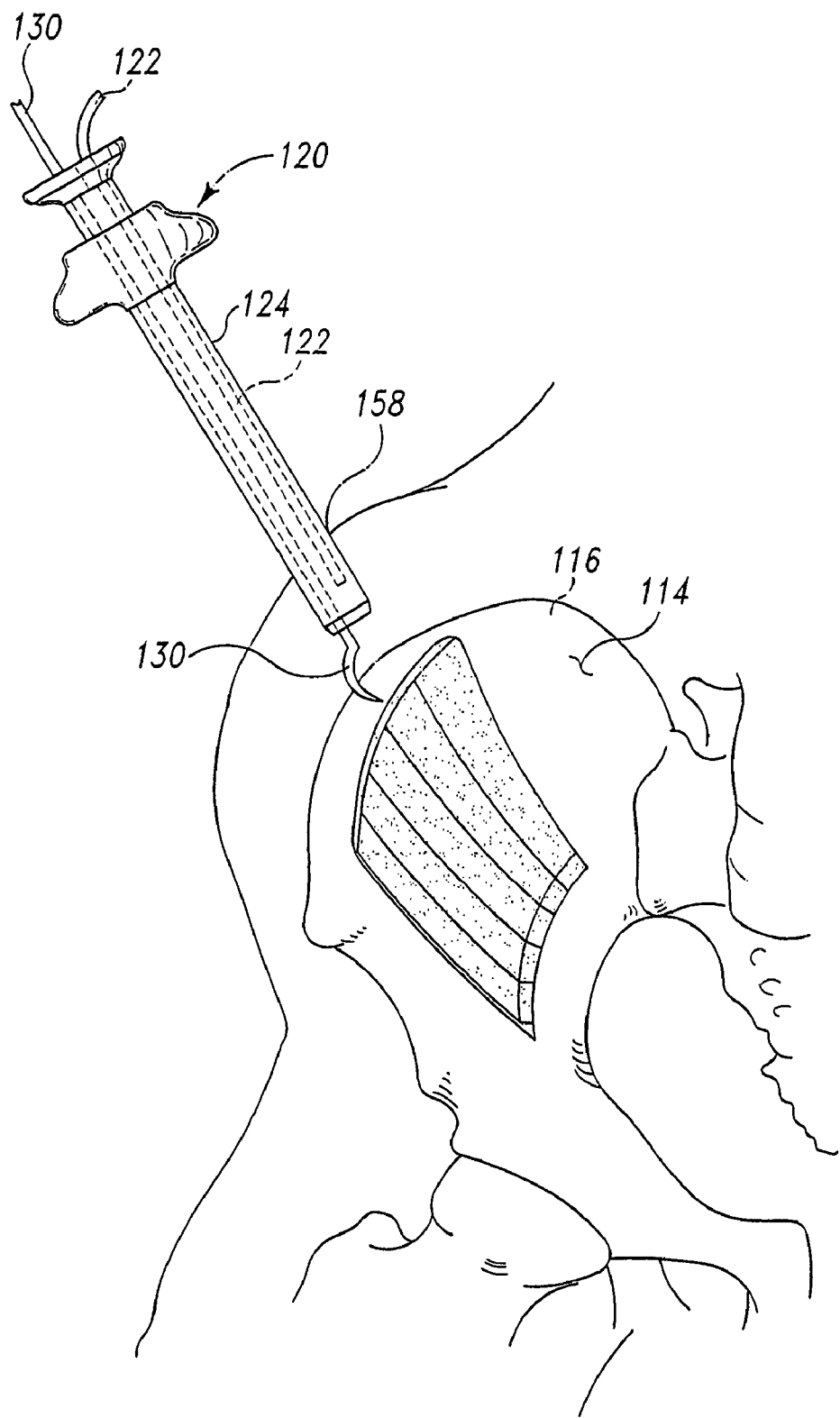
FIG. 12 is a diagrammatic perspective view which shows the harvest area of the ilium being outlined with an osteotome.

Once the obturator 128 has been removed, the surgeon may then advance a number of instruments through the cannula 124 of the trocar 120 in order to perform the harvesting operation. For example, as shown in FIG. 12, a number of straight and/or curved osteotomes 130 are advanced through the cannula 124 of the trocar 120 and thereafter manipulated or otherwise operated by the surgeon to form an outline of the area to be harvested in the ilium 116 of the patient. Such outlining of the anterior ilium prevents splitting of the ilium 116 into the sciatic notch. It should be appreciated that the surgeon performs such outlining of the ilium 116 under the visualization provided by the endoscope 122. Specifically, along with the osteotome 130, the endoscope 122 is present in the cannula 124 of the trocar 120 to provide direct visualization of the harvest site during use of the osteotome 130.

Figure 13:
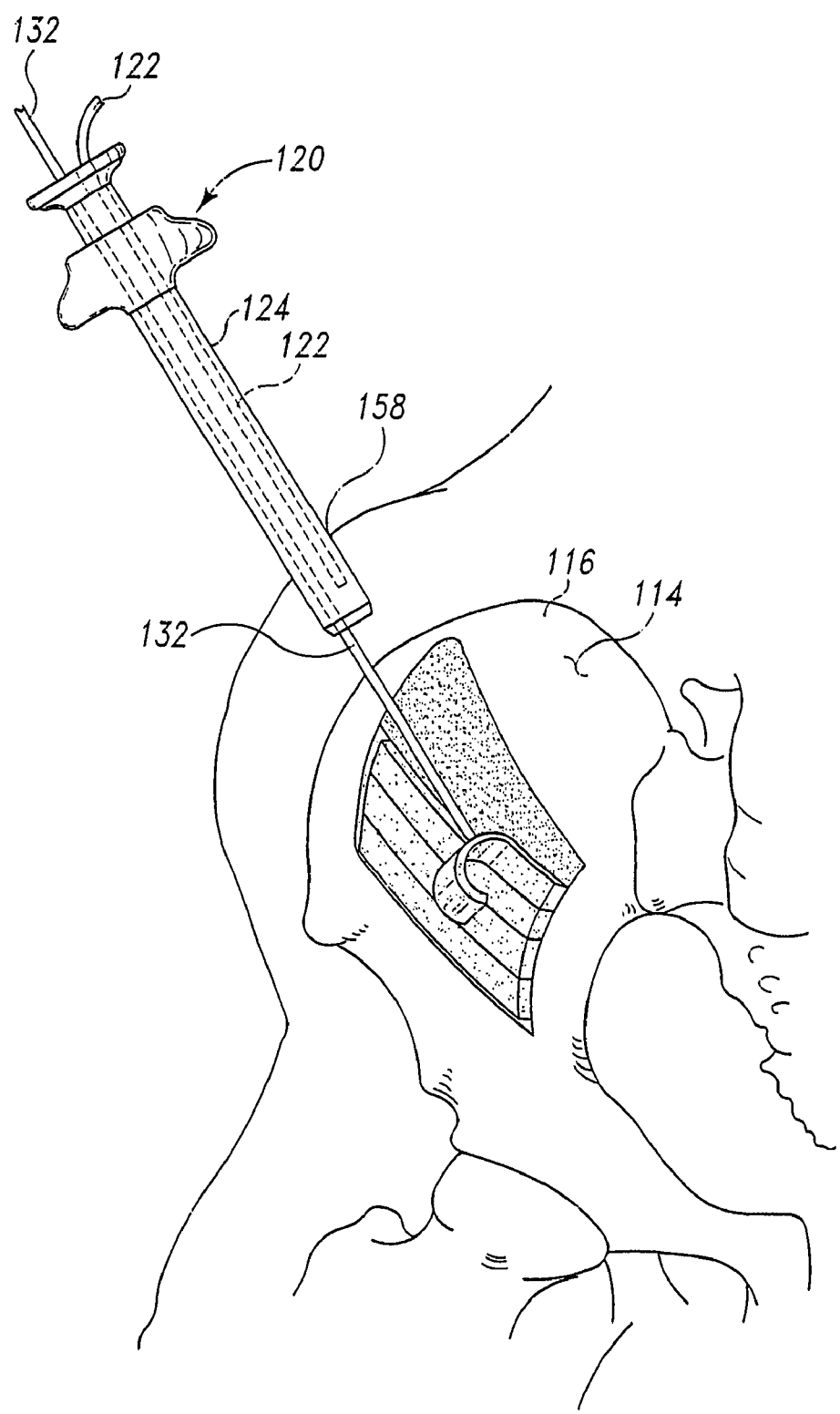
FIG. 13 is a diagrammatic perspective view which shows the bone graft material being harvested from the ilium.

Once outlined in such a manner, corticocancellous strips or other portions of the ilium 116 may then be removed. In particular, as shown in FIG. 13, a material removal instrument such as a curette or a gouge 132 may be advanced through the cannula 124 of the trocar 120 and thereafter manipulated by the surgeon in order to harvest bone graft material from the ilium 116. Such harvesting of the anterior ilium 116 is also performed under the visualization provided by the endoscope 122. Specifically, along with the material removal instrument (e.g., the gouge 132), the endoscope 122 is also positioned in the cannula 124 of the trocar 120 during the harvesting operation. As such, the images collected by the endoscope 122 are utilized by the surgeon to visualize the surgical site (i.e. the anterior ilium 116) during use of the gouge 132.

It should be appreciated that other types of instruments may also be utilized to remove the bone graft material from the patient's ilium 116. For example, an auger (not shown) may be advanced through the cannula 124 of the trocar 120 and thereafter into the cortex of the ilium 116. In such an arrangement, rotation of the auger causes removed bone material to be advanced through the cannula 124 via the helical band of the auger.

It should also be appreciated that the concepts of the present disclosure may also be utilized during delivery of the bone graft material to a delivery site such as a spinal location. For instance, a trocar 120 having an endoscope 122 associated therewith may be utilized to access the delivery site. Use of a minimally invasive device such as the trocar 120 prevents the need for elongated incisions and dissection at the delivery site. Moreover, by utilizing the endoscope 122, the delivery operation may be performed under direct visualization thereby allowing the surgeon to implant the graft material without inadvertently contacting other anatomical structures proximate to the delivery site.

It should also be appreciated that other surgical configurations may also be utilized during bone harvesting/delivery. For example, if the number or configuration of the surgical instruments required to harvest or deliver the bone graft material utilizes substantially all of the area within the cannula 124 of the trocar 120, a second trocar 120 may be utilized. For example, a first trocar 120 may be utilized to permit visualization of the surgical site with the endoscope 122, whereas a second trocar 120 may be utilized to permit access to the surgical site by providing for advancement of the necessary harvesting instruments (e.g., an osteotome, gouge, or auger).

Pelvic Osteotomies

In another exemplary embodiment of the concepts of the present disclosure, an apparatus and method are provided to allow a surgeon to perform a pelvic osteotomy. As will now be discussed in greater detail, the concepts of the present disclosure allow for the performance of a pelvic osteotomy without requiring a large, open incision. In particular, heretofore utilized techniques for performing a pelvic osteotomy generally require the use of a number of relatively long incisions, along with extensive muscle stripping and tendon division. As a result, patients often suffered from heavy blood loss, lengthy hospitalization stays, and relatively long recovery periods. Moreover, even despite the relatively extensive exposure of the hip during such a procedure, certain portions of the peri-acetabular osteotomy may still be difficult for the surgeon to visualize.

Figure 14:
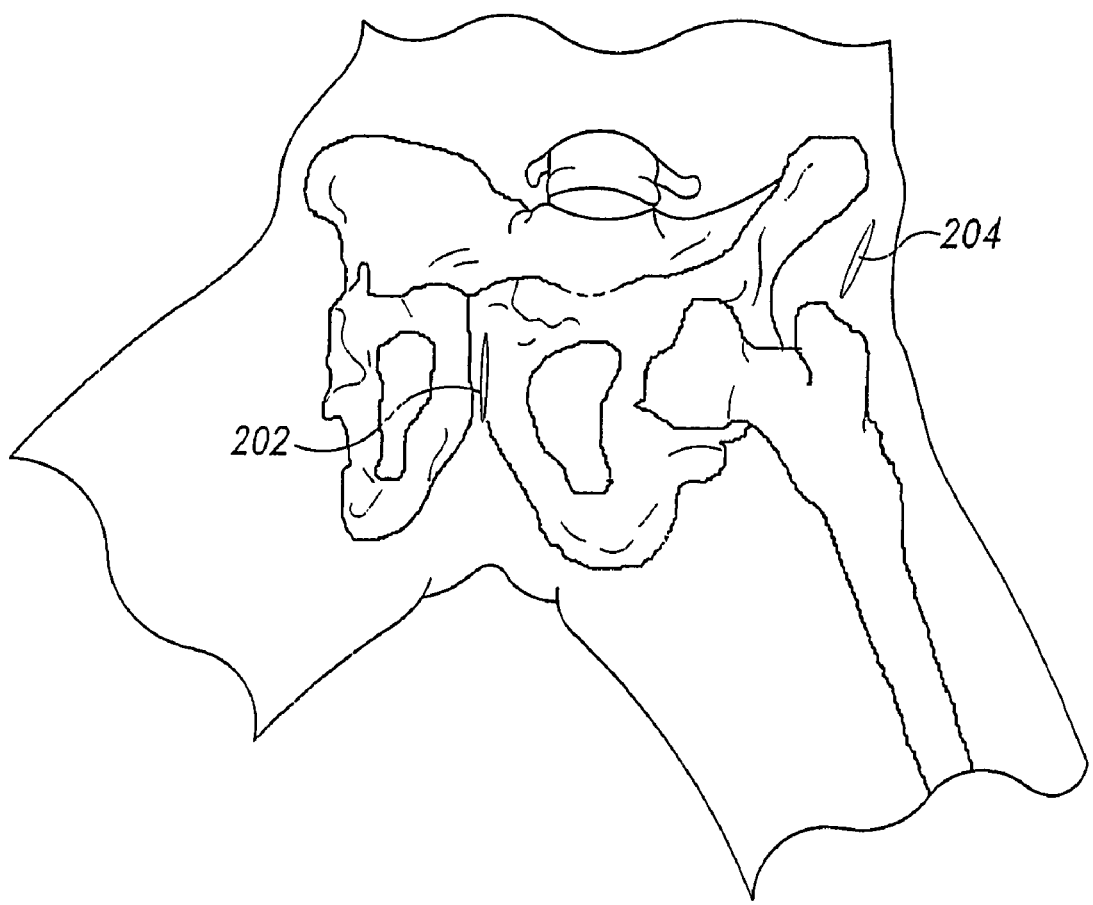
FIG. 14 is a diagrammatic perspective view which shows the entry points for a pair of trocars utilized to perform a pelvic osteotomy.

However, procedures utilizing concepts of the present disclosure avoid such drawbacks of heretofore utilized techniques. In particular, according to one illustrative embodiment of the present disclosure, a pelvic osteotomy may be performed by the surgeon while directly visualizing the bone during sawing thereof. In a more particular illustrative embodiment, a number of trocars, similar in nature to the trocars hereinbefore described (i.e., the trocar 20 and the trocar 120) are inserted through small stab incisions in the skin of the patient to visualize the surgical site. Specifically, as shown in FIG. 14, a first trocar (not shown) may be inserted at a groin insertion location 202, whereas a second trocar (not shown) may be inserted at an iliac insertion location 204.

One or both of the inserted trocars have an endoscope associated therewith. In one exemplary embodiment, the endoscope is positioned in the cannula of the trocar. In such an arrangement, the endoscope may be of conventional design and is positioned to visualize through a clear tip of an obturator associated with the trocar much in the same way the endoscopes were utilized to visualize the approach to the surgical site in the aforedescribed procedures. It should be appreciated that other configurations of the endoscope are also contemplated for use during performance of a pelvic osteotomy. For example, the endoscope may be secured to an outer portion of the cannula of the trocar, or, alternatively, may be integrated into the tip of the obturator.

Under visualization, the tip of the trocar may be advanced through the underlying tissue to a desired location near the hip bone structures to be treated. As such, the surgeon may utilize the images generated and returned from the endoscope to position the tip of the obturator proximate to the hip bone structures which are to be treated. The surgeon may then remove the obturator from the cannula of the trocar.

Once the obturator has been removed, the surgeon may then advance a number of surgical instruments through the cannulae of the trocars in order to perform the pelvic osteotomy. For example, a number of micro sawing instruments may be advanced through the cannulae and thereafter utilized to saw one or more of the structures of the hip bone in a desired location. It should be appreciated that such sawing of the hip bone is performed under the direct visualization of the endoscopes positioned in one or both of the trocars. As such, the surgeon maintains a direct view of the bone being sawed.

In addition to providing visualization of the bone which is being sawed, use of the endoscopes positioned in the trocars provides a number of other distinct advantages. For example, by directly visualizing the surgical site, inadvertent severing of certain anatomic structures may be avoided. For example, such visualization of the surgical site will prevent the inadvertent severing of the obturator neurovascular bundle or the sciatic nerve.

Implant Revision Procedures

In another exemplary embodiment of the concepts of the present disclosure, an apparatus and method are provided to allow a surgeon to visualize the surgical site during performance of an orthopaedic implant revision procedure. In particular, as will now be discussed in greater detail, the concepts of the present disclosure allow the surgeon to visualize the intramedullary canal of a bone during an orthopaedic implant revision procedure. Such capability is a significant improvement over heretofore utilized techniques in which the surgeon did not possess the ability to "see" into the intramedullary canal beyond his or her ability to "peer" into the canal. The ability to visualize the intramedullary canal has been improved somewhat by the use of illumination instruments which are lowered into the canal, but the surgeon remains constrained by the limitation that he or she can only observe the canal from "outside" the bone.

Figure 15:
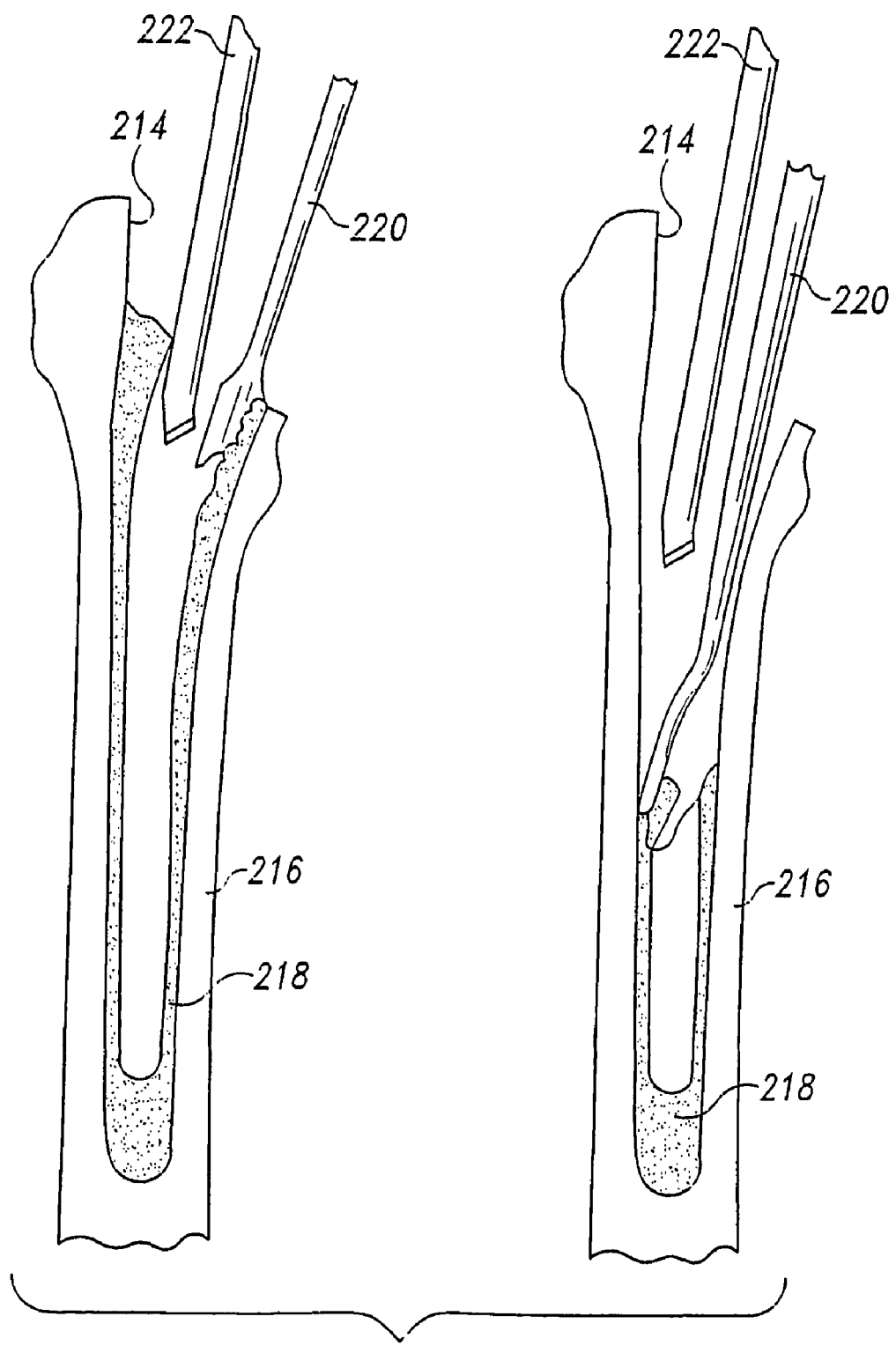
FIG. 15 is a pair of diagrammatic cross sectional views which show the performance of an endoscopic implant revision procedure.

However, procedures utilizing concepts of the present disclosure avoid such drawbacks of heretofore utilized techniques. In particular, as shown in FIG. 15, according to one illustrative embodiment of the present disclosure, an endoscope 222 is lowered into the intramedullary canal 214 of the bone 216 to directly visualize the bone during the implant revision procedure. In particular, as shown in FIG. 15, a number of cutting instruments 220 may be utilized to scrape or otherwise remove any residual bone cement 218 (i.e., the cement 218 that was utilized to retain the previously removed prosthesis). During such a procedure, the endoscope 222 may be lowered into the intramedullary canal 214 such that the images generated by the endoscope 222 may be utilized to inspect the intramedullary canal 214 during the implant revision procedure. Such an inspection may be utilized to confirm, amongst other things, adequate bone cement removal and the lack of any spiral fractures in the bone.

In such an arrangement, the endoscope 222 may be of conventional design and may be positioned to visualize the canal 214 continuously during the procedure. Alternatively, the endoscope 222 may be lowered into the canal 214 only periodically during the procedure.

In a more specific exemplary embodiment, the endoscope 222 may be provided as part of a "combination" instrument. For example, instruments for use in implant revision procedures have heretofore been designed which provide for irrigation of the canal 214, suction of removed material or debris, illumination (i.e., lighting) of the canal 214, and cutting of the residual cement 218. As such, these irrigation-suction-illumination-cutting instruments have become a useful tool for surgeons since they perform multiple functions within the confines of a single instrument. In order to render such instruments even further useful to a surgeon, the concepts of the present disclosure provide for the bundling of the endoscope 222 with such a combination instrument.

The resultant instrument would provide for all of the functions described above (i.e., irrigation, suction, illumination, and cutting) while also providing for visualization of the intramedullary canal 214. Specifically, the integration of the endoscope 222 into the device would provide for a device which allows the surgeon to visualize the inner surfaces of the intramedullary canal 214, including the residual bone cement 218 present therein, while also performing one or more of the other associated functions of the instrument (i.e., irrigation, suction, illumination, and cutting).

Percutaneous Plating

In another exemplary embodiment of the concepts of the present disclosure, an apparatus and method are provided to allow a surgeon to perform a bone plating procedure in a percutaneous manner. As will now be discussed in greater detail, the concepts of the present disclosure allow for the performance of a minimally invasive, percutaneous bone plating procedure without requiring a large, open incision. In particular, heretofore utilized techniques for performing such a plating procedure generally require the use of a number of relatively long incisions, along with the associated extensive muscle stripping and tendon division. As a result, patients often suffered from heavy blood loss, lengthy hospitalization stays, and relatively long recovery periods.

However, procedures utilizing concepts of the present disclosure overcome such drawbacks of heretofore utilized techniques. In particular, according to one illustrative embodiment of the present disclosure, an apparatus and method are provided for inserting a bone plate into a relatively small incision and thereafter securing the plate to a desired position on a bone. In doing so, the plate is inserted under visualization provided by an endoscope associated with the apparatus.

Figure 16:
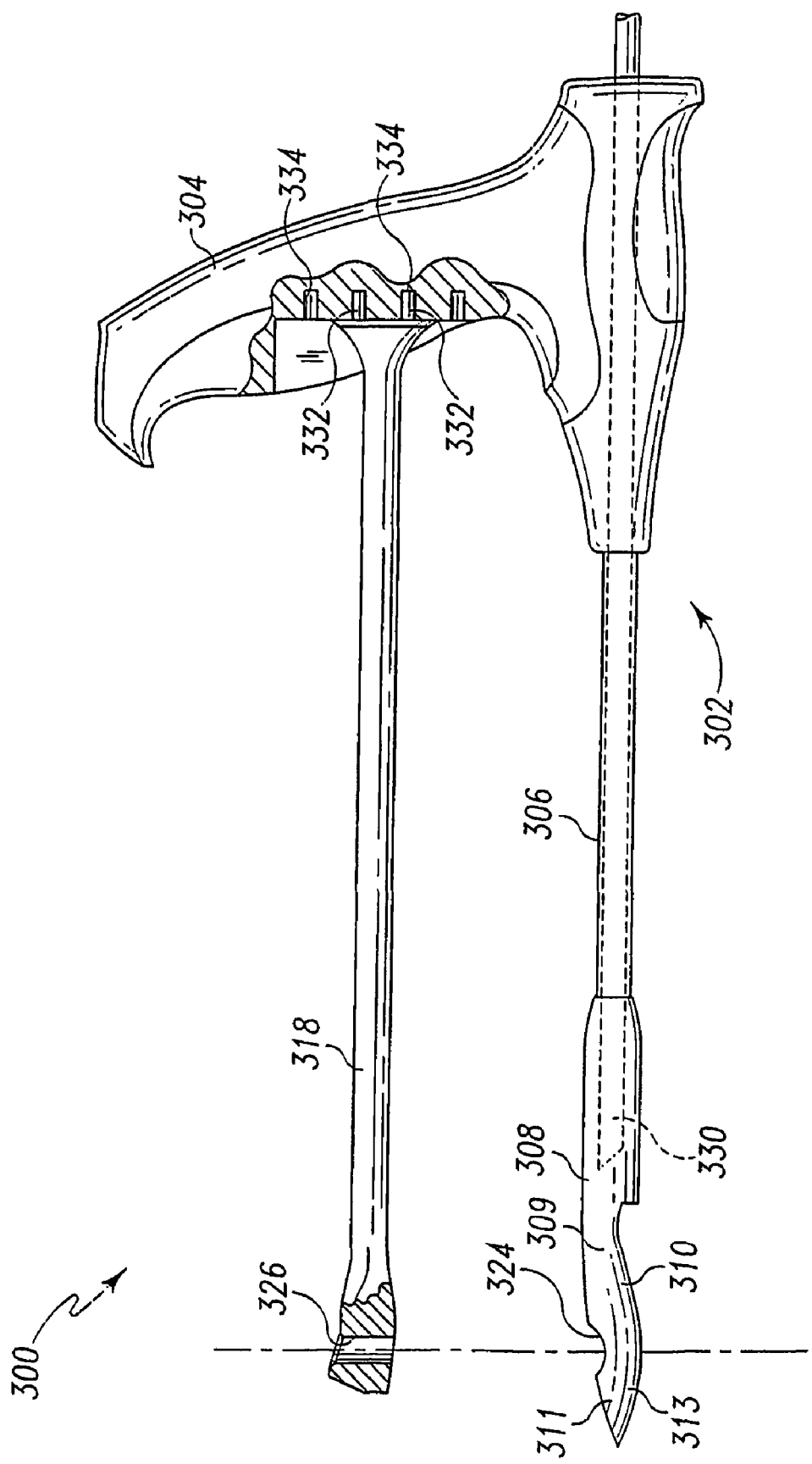
FIG. 16 is a side elevational view of an exemplary embodiment of a bone plating instrument.

Referring now to FIGS. 16-53, there is shown a number of exemplary embodiments of a bone plating instrument 300. The plating instrument 300 includes a housing 302 (which, in the exemplary embodiment described herein, includes a handle 304), an elongated cannulated shaft 306, and a tissue expander 308. As shown in FIG. 16, in one exemplary embodiment, the tissue expander 308 may be embodied as a spoon-shaped member 310 (referred to hereinafter simply as spoon 310), whereas in other embodiments, the tissue expander 308 is embodied as a tunnel-shaped member 312 (referred to hereinafter simply as tunnel 312). It should be appreciated that the tissue expander 308 is utilized to expand the tissue around the bone 314 to be treated to provide access to the bone 314 for both a bone plate 316 and the instruments necessary for installation of the same. As such, the tissue expander 308 provides a subcutaneous working space for the positioning and securing (with bone screws) of a bone plate 316 onto a fractured bone 314.

Figure 17:
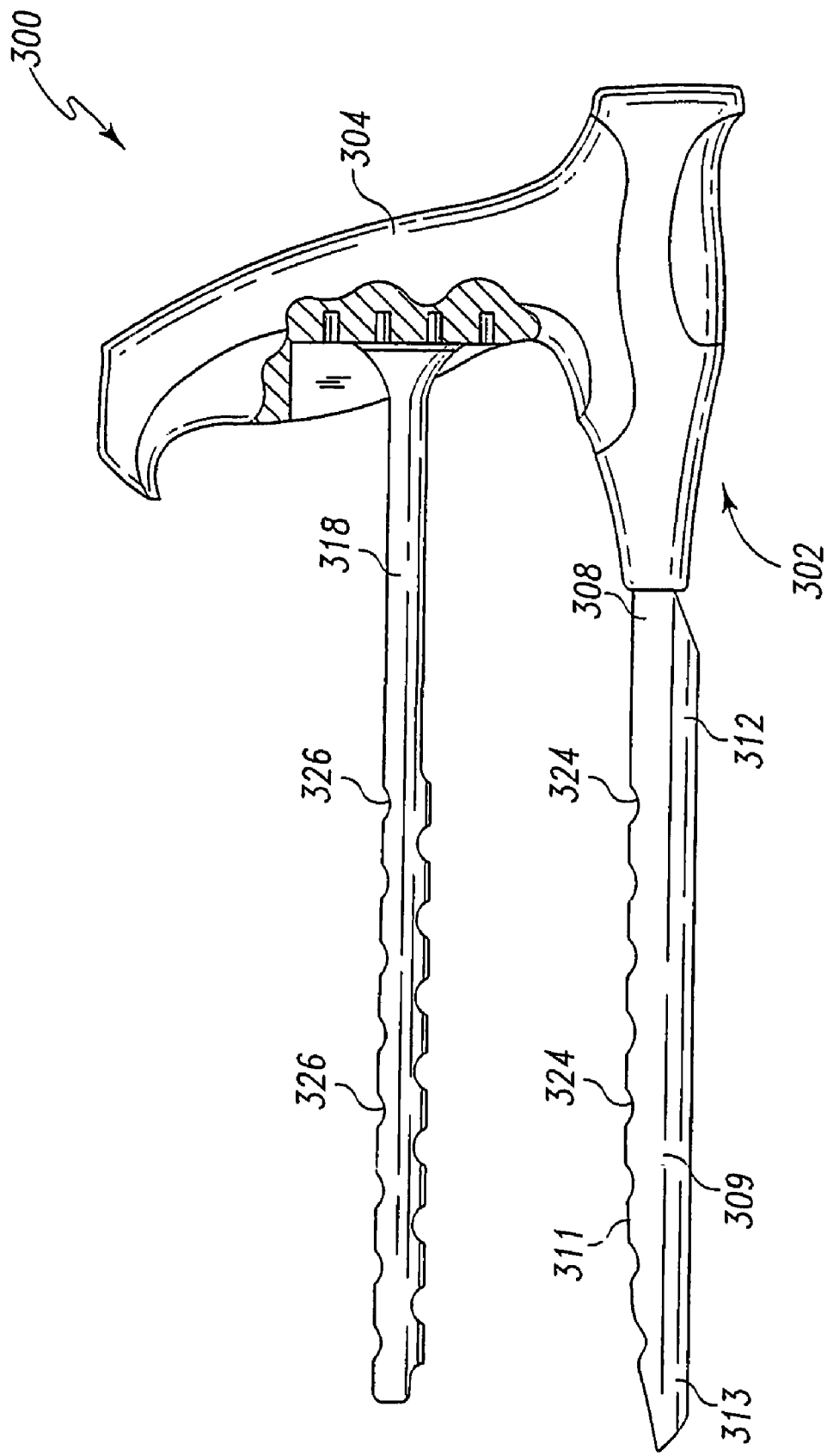
FIG. 17 is a side elevational view of another exemplary embodiment of a bone plating instrument.

As shown in, for example, FIGS. 16, 17, and 23, the tissue expanders 308 of the present disclosure include a body 309 having a top wall 311 and a pair of downwardly extending side walls 313. It should be appreciated that although the body 309 of the tissue expanders 308 are herein described as being generally semi-tubular or otherwise arcuate shaped in cross section, other configurations of the body 309 are also contemplated for use. For example, the cross sectional shape of the body 309 of the tissue expanders 308 (i.e., either the spoon 310 or tunnel 312) may be non-arcuate in shape such as in the case of two longitudinal rails spaced apart and coupled by a number of cross elements.

The aforedescribed embodiments of the tissue expanders 308 provide for a relatively large degree of flexibility in regard to the design of the plating instrument 300. Additional flexibility may be achieved by the use of removable tissue expanders 308. In particular, the spoon 310 may be configured to be removably secured to the elongated cannulated shaft 306, whereas the tunnel 312 may be configured to be removably secured to the handle 304. In such an arrangement, different sizes, shapes, or types of spoons and tunnels may be utilized on a common shaft 306/handle 304 assembly thereby allowing the plating instrument 300 to be adapted to fit the needs of a given patient's anatomy or surgical procedure.

Figure 19:
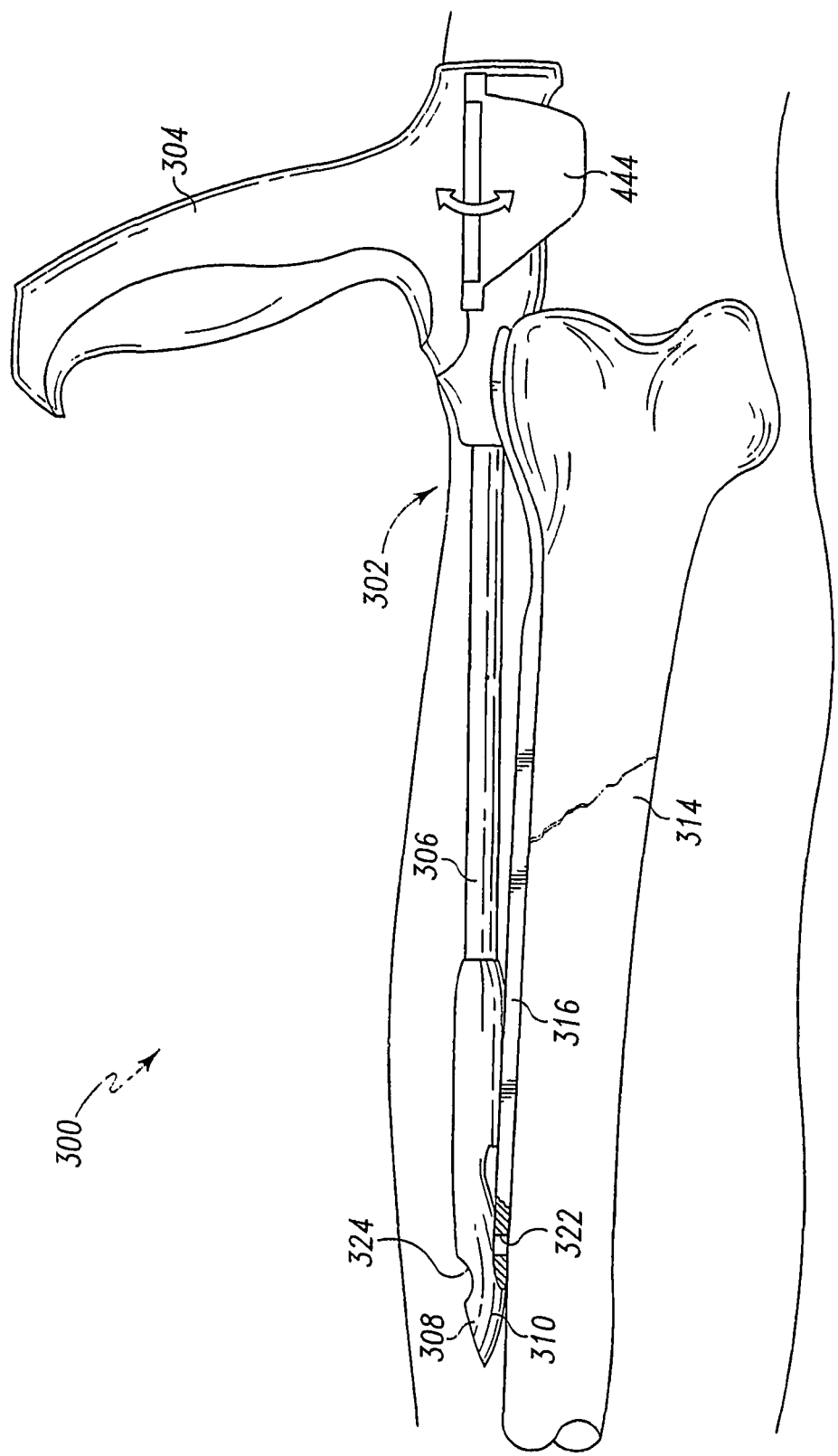
FIG. 19 is a diagrammatic side elevational view of a bone plating instrument positioned in the body of a patient.
Figure 25:
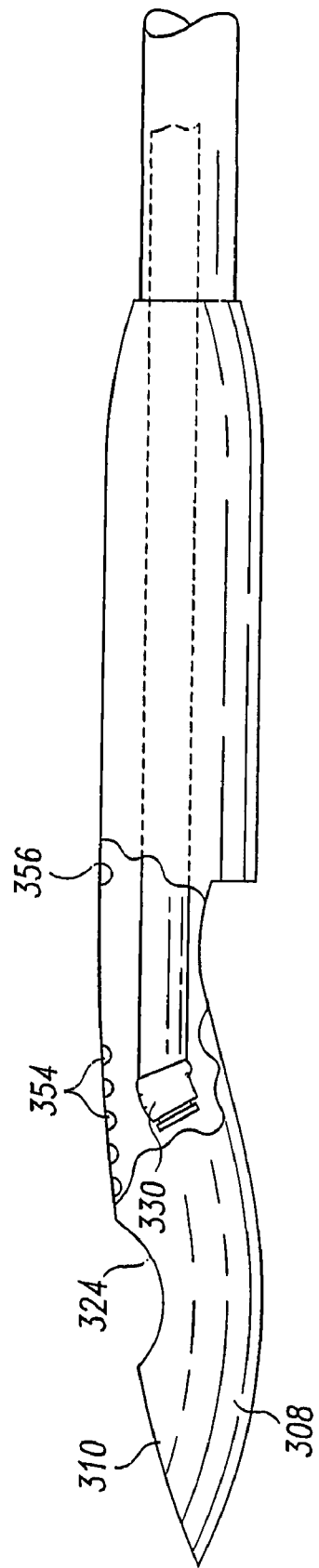
FIG. 25 is a diagrammatic side elevational view which shows a number of LED's positioned with the spoon.

The plating instrument 300 has an endoscope 330 associated therewith (see, e.g., FIG. 25). The endoscope 330 is provided to allow the surgeon to visualize the bone 314 along with the plate 316 being secured thereto. Specifically, as shown in FIG. 19, during installation of the bone plate 316, the images generated by the endoscope 330 are utilized by the surgeon to visualize the surgical site.

The plating instrument 300 also includes a screw alignment device or jig 318. The screw alignment device 318 is provided to align bone screws 320 with a number of holes 322 defined in the bone plate 316 (see, e.g., FIG. 39). Specifically, the screw alignment device 318, when secured to the housing 302 of the plating instrument 300, may be utilized to guide the screws 320 during percutaneous advancement thereof into the holes 322 of the bone plate 316. To do so, the surgeon visualizes the location of the individual holes 322 of the bone plate 316 by use of the endoscope 330. Under such visualization, the surgeon may then align one of the holes 322 of the plate 316 with an access hole 324 defined in the tissue expander 308. As shown in FIG. 16, the spoon 310 has a single hole 324 defined therein. As such, the surgeon, under visualization, aligns the hole 324 of the spoon 310 with one of the holes 322 of the bone plate 316.

Once the holes 324, 322 are aligned with one another, a screw 320 may be inserted through a stab incision in the skin of a patient by use of the screw alignment device 318. Specifically, when the screw alignment device 318 is secured to the housing 302 of the plating instrument 300, a guide hole 326 defined therein is aligned with both the hole 324 in the tissue expander 308 and the hole 322 in the bone plate 316. As such, a cannulated guide 342 may be advanced through the hole 326 in the alignment device 318, the stab incision and underlying tissue, and through the hole 324 in the tissue expander 308 (see, e.g., FIG. 39). A bone screw 320 may then be advanced through the cannulated guide 342, the hole 324 in the tissue expander 308, and one of the holes 322 in the bone plate 316 and thereafter threadingly engage the fractured bone 314

It should be appreciated that the stab incision through which the screw 320 is advanced may be created in a number of different manners. For example, an obturator (not shown) may first be advanced through the cannulated guide 342 and into the skin and underlying tissue of the patient. The obturator may be advanced to the point at which the obturator enters the hole 324 of the tissue expander 308. The obturator may then be removed from the cannulated guide 342 such that the screw 320 may thereafter be advanced through the guide 342. It should be appreciated that an elongated screw driver (not shown) may be advanced through the cannulated guide 342 (and hence the incision) to drive the screw 320 into the bone 314.

Figure 18:
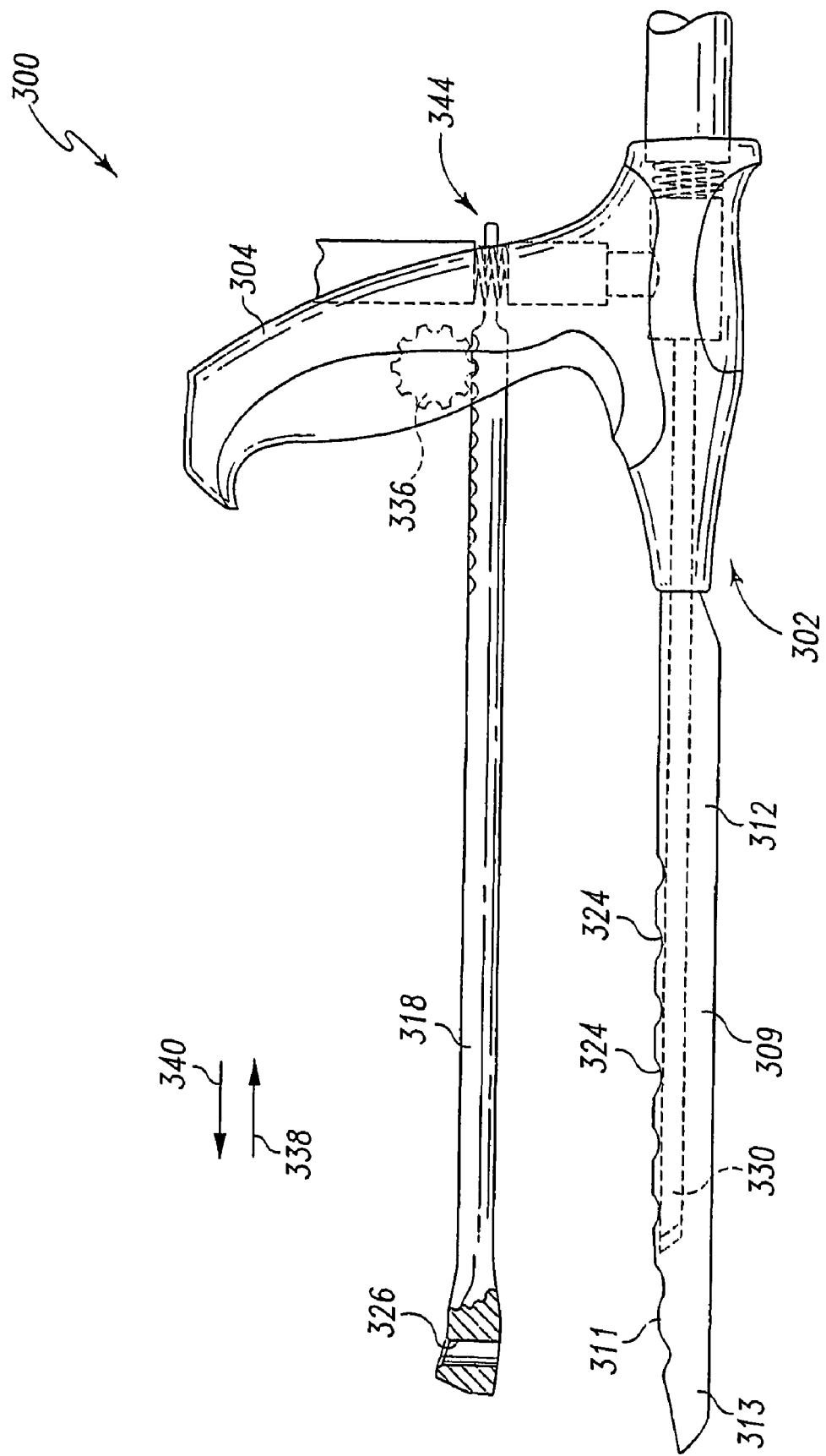
FIG. 18 is a side elevational view of another exemplary embodiment of a bone plating instrument.

As shown in FIGS. 16-18, the screw alignment device 318 may take on many different forms. Specifically, the design of the screw alignment device 318 may be modified to, for example, cooperate with a given design of the tissue expander 308. For example, as shown in FIG. 16, the screw alignment device 308 may take the form of an elongated member with only a single hole 326. In such an embodiment, the hole 326 of the alignment device 308 is aligned with the hole 324 in the spoon 310. In use, the surgeon utilizes the handle 304 to pull the instrument 300 along the length of the implanted plate 316 in order to successively align the hole 324 of the spoon 310 (and hence the hole 326 of the alignment device 318) with the individual holes 322 of the implanted plate 316.

However, in the case of the instrument 300 being configured with the tunnel 312, the alignment device 318 may be configured with a plurality of the holes 326, each of which aligns with one of the plurality of holes 324 defined in the tunnel 312. In such an arrangement, the position of the holes 324 (and hence the holes 326) may be predetermined in order to align with the holes 322 defined in the plate 316. In this manner, the instrument 300 need not be moved in order to drive successive screws 320.

As shown in FIG. 16, the screw alignment device 318 has an attachment member such as a number of pins 332 defined in the inner end thereof. The pins 332 may be positioned in any adjacent pair of holes 334 defined in the housing 302 (specifically, the handle 304) in order to secure the alignment device 318 to the housing 302. As shown in FIG. 16, the handle 304 may be configured with a plurality of holes 334. In doing so, the height at which the alignment device 318 is secured to the handle 304 may be adjusted thereby allowing for variations in the thickness of the tissue surrounding the fracture bone 314.

Numerous other manners for adjusting the height of the screw alignment device 318 are also contemplated for use. For example, the plating instrument 300 may be configured to include a gear assembly which, upon rotation of a knob or the like, causes the screw alignment device 318 to be moved upwardly and downwardly. For instance, a rack and pinion gear assembly, similar to the type utilized in the construction of conventional microscopes for moving the specimen tray relative to the lens, may be utilized to adjust the position of the screw alignment device 318.

The screw alignment device 318 may also be secured to the handle 304 in other manners. For example, the screw alignment device 318 may be pivotally secured to the handle 304 to allow the surgeon to pivot the device 318 out of the way when, for example, operating on tissue. Moreover, as shown in FIG. 22, the screw alignment device 318 may be arcuate or curved in shape to conform to the arcuate or curved shape of the bone plate 316 being implanted (which in turn conforms to the bone to which it is being secured). In such an arrangement, the alignment device 318 may be rotatably secured to the handle 304 (or removable for rotation) thereby allowing the device 318 to conform to a plate 316 with either a right-hand or left-hand curvature (see FIG. 22). Moreover, the locations of the holes 326 of the screw alignment device 318 may be configured to allow for the use of a single design of the alignment device 318 with a number of different bone plate designs.

Figure 33:
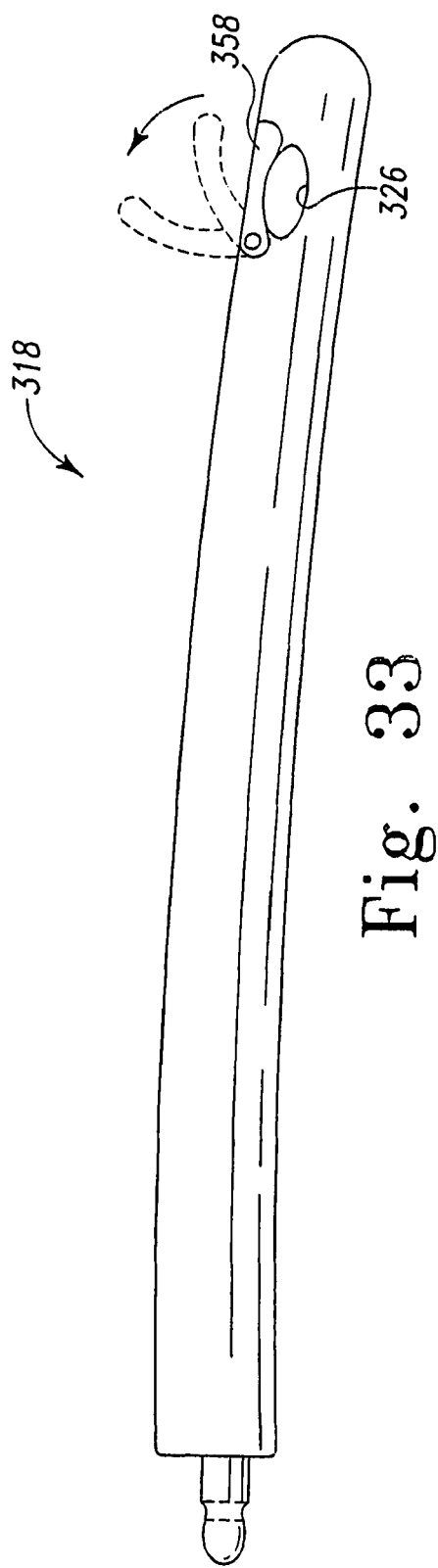
FIG. 33 is a plan view of a screw alignment device having a latch mechanism.

A further alternative feature for use in the design of the screw alignment device 318 is shown in FIG. 33. In this embodiment, the screw alignment device 318 has a single hole 326. The alignment device 318 of this embodiment includes a pivotal latch 358 which may be utilized to allow the surgeon to leave an instrument or the like in the stab incision. For example, an instrument, such as the trocar/obturator assembly utilized to create the stab incision for screw insertion, is only removable from the hole 326 of the alignment device 318 when the distal tip thereof is external to the body of the patient. However, use of the latch 358 allows an implanted instrument (i.e., an instrument having a distal end present in the tissue of the patient) to be removed from the hole 326 thereby allowing the instrument to remain in the body of the patient for subsequent use during the procedure.

Figure 38:
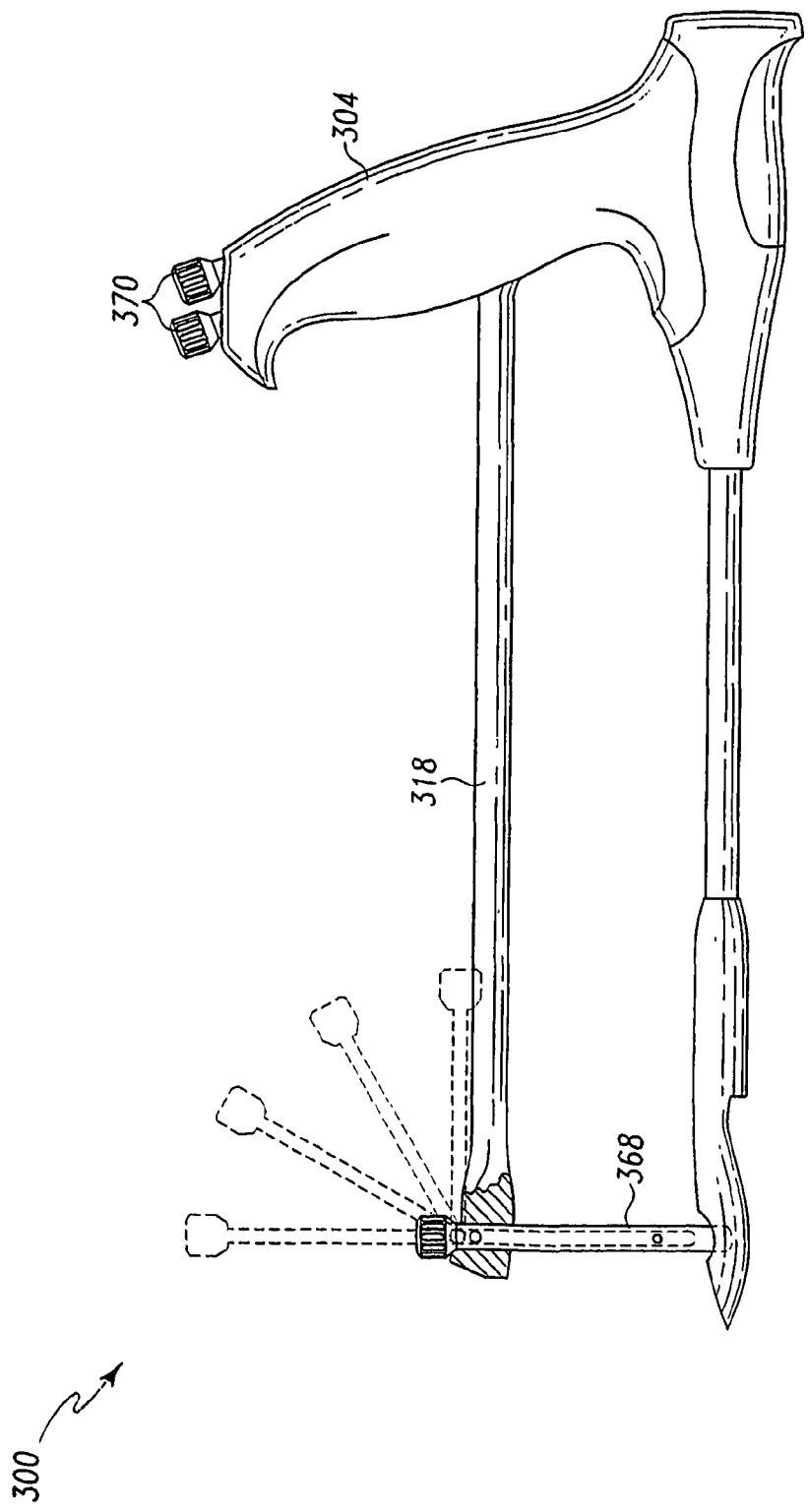
FIG. 38 is a perspective view of a bone plating instrument having an integrated cannulated sleeve.
Figure 39:
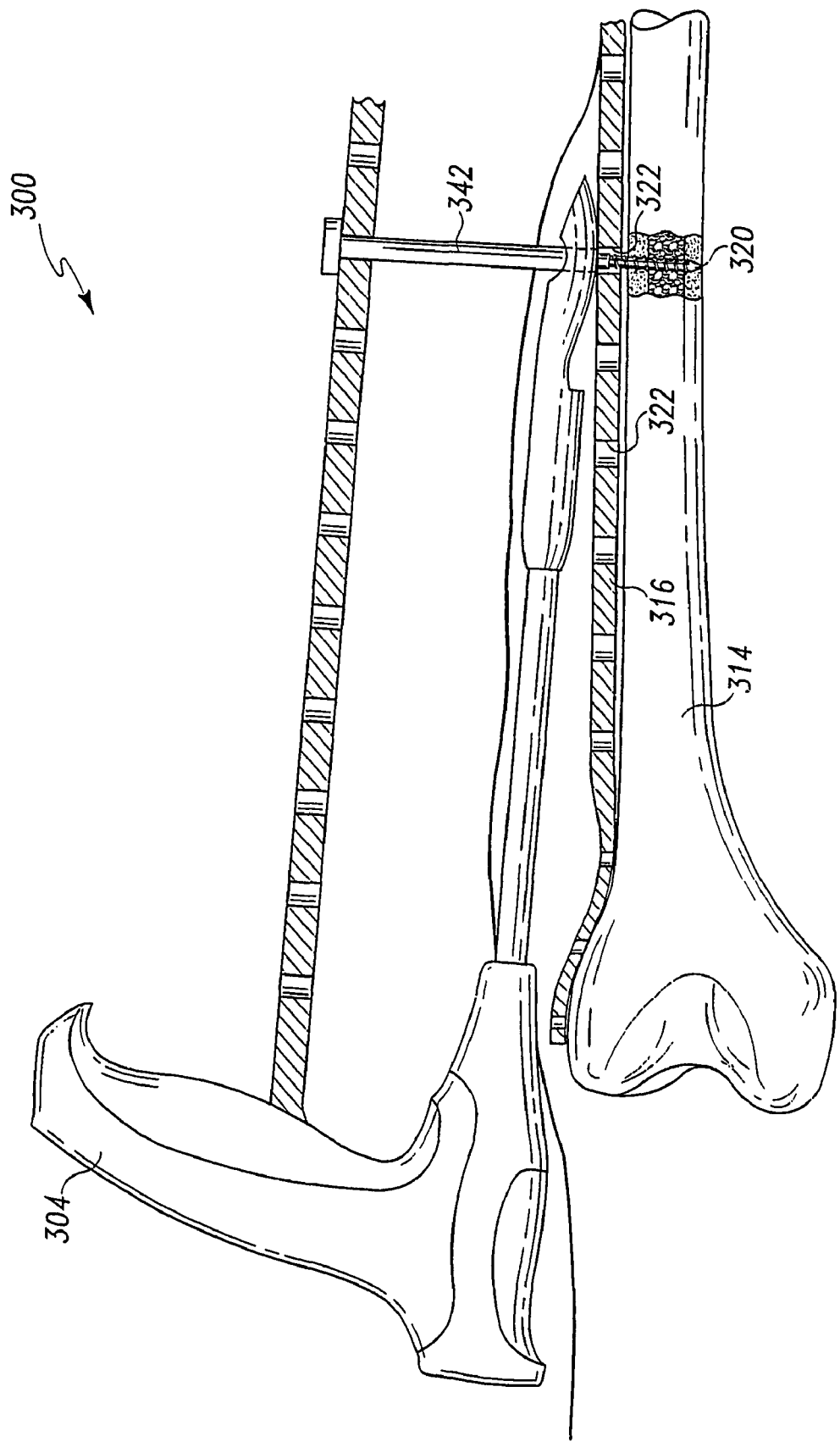
FIG. 39 is a fragmentary elevational view which shows a bone plating instrument being utilized to secure a bone plate to a bone, note that the bone plate is shown in cross section for clarity of description.

As shown in FIG. 38, in an alternate configuration of the plating instrument 300, an integrated handle 304/screw alignment device 318 includes a cannulated sleeve 368 that is pivotally and slidably secured to the alignment device 318. In such an arrangement, a number of instruments 370 may be advanced through the sleeve 368 in order to perform a desired function. For example, one of the removable instruments 370 may be an obturator which is advanced through the cannulated sleeve 368 to create the stab incision. The removable instrument 370 could also be a drill or tap which is advanced through the sleeve 368 and thereafter utilized to create a hole in the fracture bone into which a screw will be driven. As shown in phantom lines in FIG. 38, when not in use, the cannulated sleeve 368 may be slid and pivoted to a substantially horizontal storage position on the upper surface of the alignment device 318.

Figure 40:
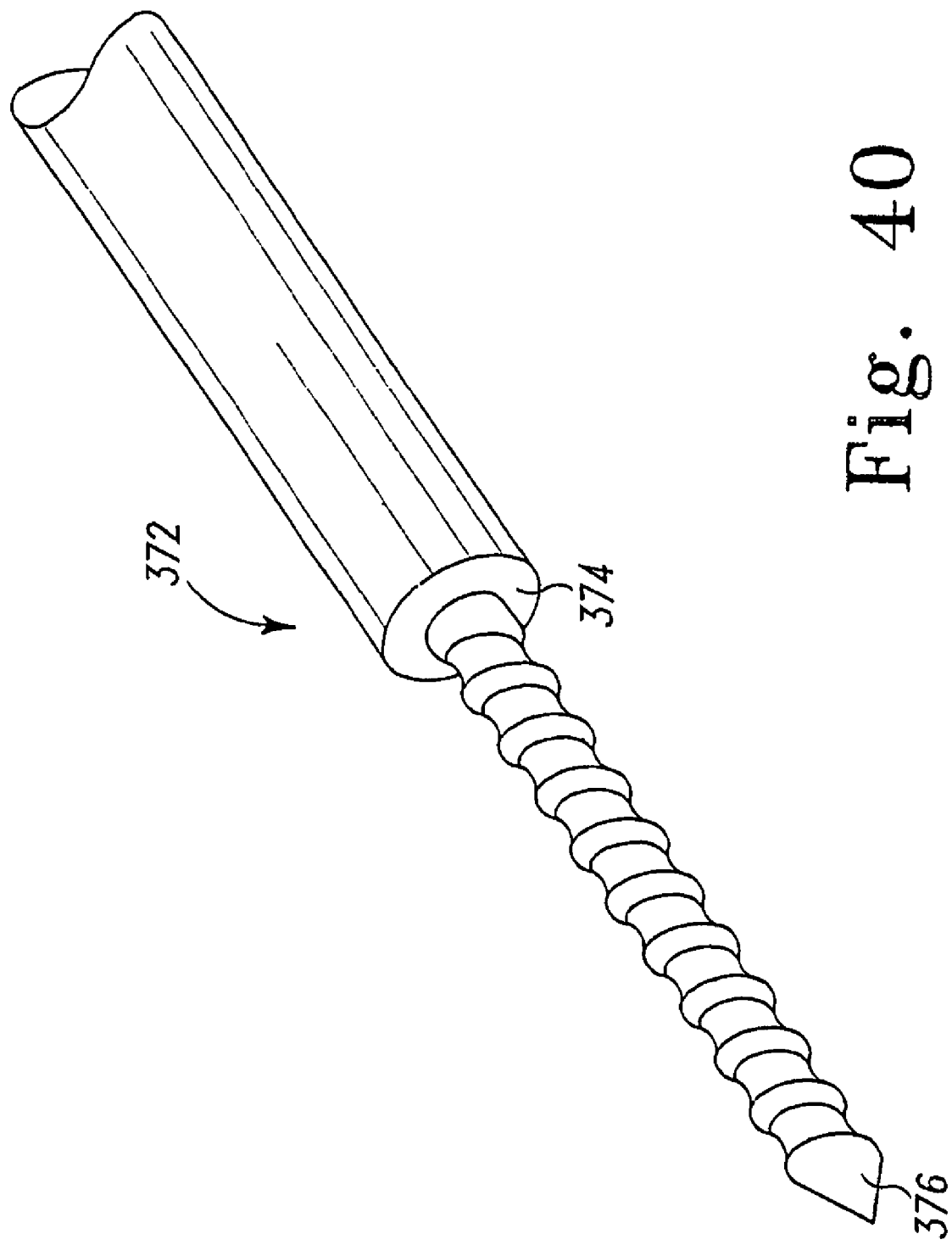
FIG. 40 is a fragmentary perspective view of a tap which may be used with the instrument of FIG. 38.

Use of a cannulated sleeve which is integral to the instrument (i.e., the integrated cannulated sleeve 368) allows for the elimination of certain instruments which are commonly utilized in plating procedures. For example, as shown in FIG. 40, a tap instrument 372 having a shoulder portion 374 and a tap portion 376 may be utilized in conjunction with the cannulated sleeve 368. A similarly configured (i.e., shouldered) drill (not shown) could also be utilized in conjunction with the cannulated sleeve 368. By doing so (i.e., utilizing the cannulated sleeve 368 for operation of both instruments), the need for separate tap and drill guides is eliminated.

The cannulated sleeve 368 may be transparent in design and thus allow for the instruments advancing therethrough (e.g., the obturator) to be endoscopically viewed. Alternatively, the cannulated sleeve 368 may have a number of longitudinal slots defined therein for such endoscopic viewing of the passage of an instrument therethrough.

Other embodiments of the screw alignment device 318 are also contemplated for use. For example, as shown in FIG. 18, the screw alignment device 318 may be movable relative to the housing 302 of the instrument 300. Specifically, a ratchet mechanism 336 may be utilized to ratchet or otherwise move the screw alignment device in the general direction of arrows 338 and 340 of FIG. 18. In such an arrangement, the screw alignment device 318 need only be embodied with a single hole 326 since the movement of the device 318 provided by the ratcheting mechanism 336 is utilized to position the hole 326 in the appropriate location relative to the holes 324 in the tunnel 312. It should be appreciated that the ratchet mechanism 336 may be configured such that each incremental movement of the alignment device 318 generated by the ratchet mechanism 336 coincides with the placement of the hole 326 into alignment with one of the holes 324 of the tunnel 312.

The embodiment of the instrument 300 shown in FIG. 18 also includes a coupler 344 which coordinates the movement of the endoscope 330 with that of the screw alignment device 318. Specifically, the coupler 344 may be utilized to mechanically couple the endoscope 330 to the screw alignment device 318. As such, as the surgeon operates the ratchet mechanism 336 to position hole 326 of the alignment device 318 over one of the holes 324 in the tunnel 312, the endoscope 330 is likewise moved in the direction of arrows 338, 340 to a position which allows the endoscope 330 to collect the desired images of the screw driving operation. Hence, when the surgeon positions the screw alignment device 318 in a desired location, the endoscope 330 is likewise positioned in a desired location to observe the associated procedure (e.g., screw insertion).

Referring now to FIG. 53, there is shown another exemplary embodiment of the bone plating instrument 300. In lieu of a gear mechanism for re-positioning the tissue expander 308 and the alignment device 318, the plating instrument 300 of FIG. 53 includes a telescoping shaft 306 and an alignment device 318 with a telescoping body. A spring loaded detent 319 is positionable in any one of a number of locator holes 321 to position the shaft (and hence the tissue expander 308) and the alignment device 318 in a desired position.

Figure 20:
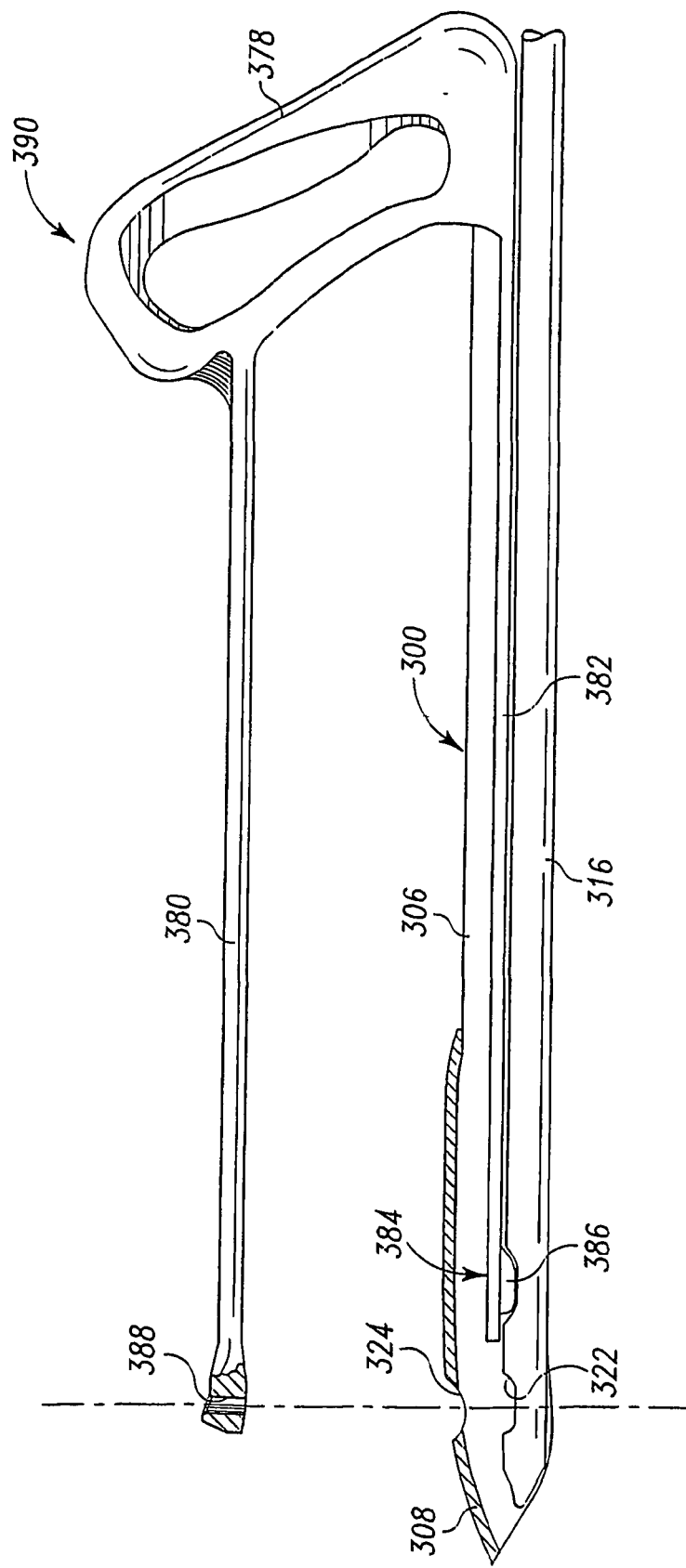
FIG. 20 is a side elevational view of a screw locating device.

Referring now to FIG. 20, there is shown another exemplary embodiment of a bone plating instrument. In this case, an alignment instrument 390 provides the screw alignment function and is intended to be utilized in conjunction with the instrument 300. The alignment instrument 390 includes a handle 378 having a pair of parallel arms 380, 382 extending therefrom. The upper arm 380 has a hole 388 defined in that functions essentially the same as the hole 326 of the screw alignment device 318 (i.e., aligns with the hole 324 of the tissue expander 308). The lower arm 382 includes a location feature 384 in the form of a tab 386 which aligns with one of the holes 322 defined in the implanted bone plate 316. The dimensions of the alignment instrument 390 are selected such that when the tab 386 is positioned in one of the holes 322, one of the other holes 322 (e.g., the adjacent hole 322) is aligned with both the hole 324 of the tissue expander 308 and the hole 388 of the upper arm 380. As such, the precise location for the stab incisions associated with screw insertion can be enhanced.

It should be appreciated that similar concepts may be incorporated into the design of the tissue expander 308. For example, the spoon 310 or the tunnel 312 may be configured to include a locating tab similar to the tab 386 such that when the tab is positioned in one of the holes 322 of the bone plate 316, one of the other holes 322 (e.g., the adjacent hole 322) is aligned with the hole 324 in the spoon or tunnel (and hence the hole 326 of the screw alignment device 318).

Figure 28:
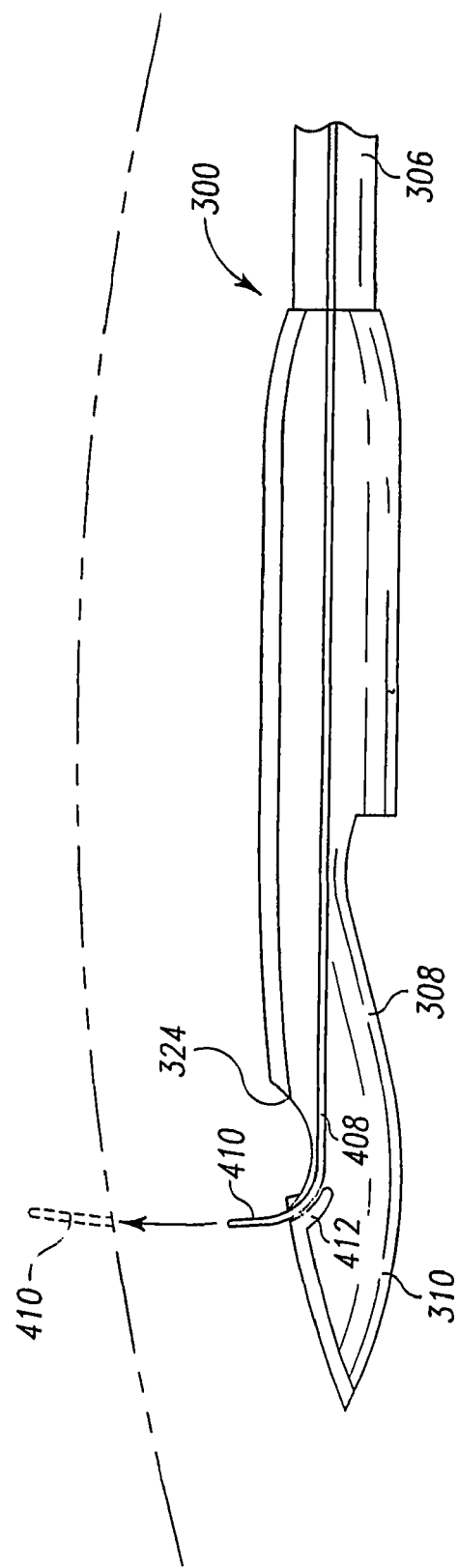
FIG. 28 is a diagrammatic side elevational view which shows a guide wire for use in determining hole location of the spoon.

It should be appreciated that there are numerous other manners for aligning the hole 324 (or holes 324) of the tissue expander 308 (and hence the hole 326 of the screw alignment device 318) with the holes 322 of the bone plate 316. For example, as shown in FIG. 28, a flexible, remotely operable, guide wire 408 may be extendable and retractable through the cannulated shaft 306 of the plating instrument 300. Once the spoon 310 (or tunnel 312) is located precisely over the plate hole 322 of interest (as determined by use a locating feature on the spoon or tunnel, or the use of the endoscope 330), the surgeon may advance the wire 408 distally. During such distal movement of the wire 408, the tip 410 of the wire is guided by a ramp 412 which guides the wire tip 410 vertically out of the hole 324 of the spoon 310 (or tunnel 312). Continued vertical advancement of the wire tip 410 causes it to penetrate through the underlying tissue and eventually puncture the skin (as shown in phantom in FIG. 28). The point at which the tip 410 of the wire exits the skin may be utilized as an indicator for the location of a stab incision for subsequent screw insertion.

It should be appreciated that the tissue expander 308 itself may provide the necessary alignment features for screw insertion. For example, the outer surfaces of the spoon 310 or the tunnel 312 may have alignment features defined therein which allow the surgeon to tactilely locate the position of the hole 324 (or holes 324) in the spoon or tunnel through the tissue of the patient. Alternatively, a pointer laser may be mounted on the cannulated shaft 306, with an associated mirror positioned on the inside surface of the spoon 310 or tunnel 312, so that a laser beam may be reflected or otherwise directed outwardly and upwardly through the hole 324 (or holes 324) of the spoon or tunnel. In this manner, the directed beam would illuminate the location of the stab incision to be utilized to drive a screw 320 through the hole 324 in the spoon 310 or tunnel 312 and hence the hole 322 in the plate 316 positioned thereunder.

Figure 26:
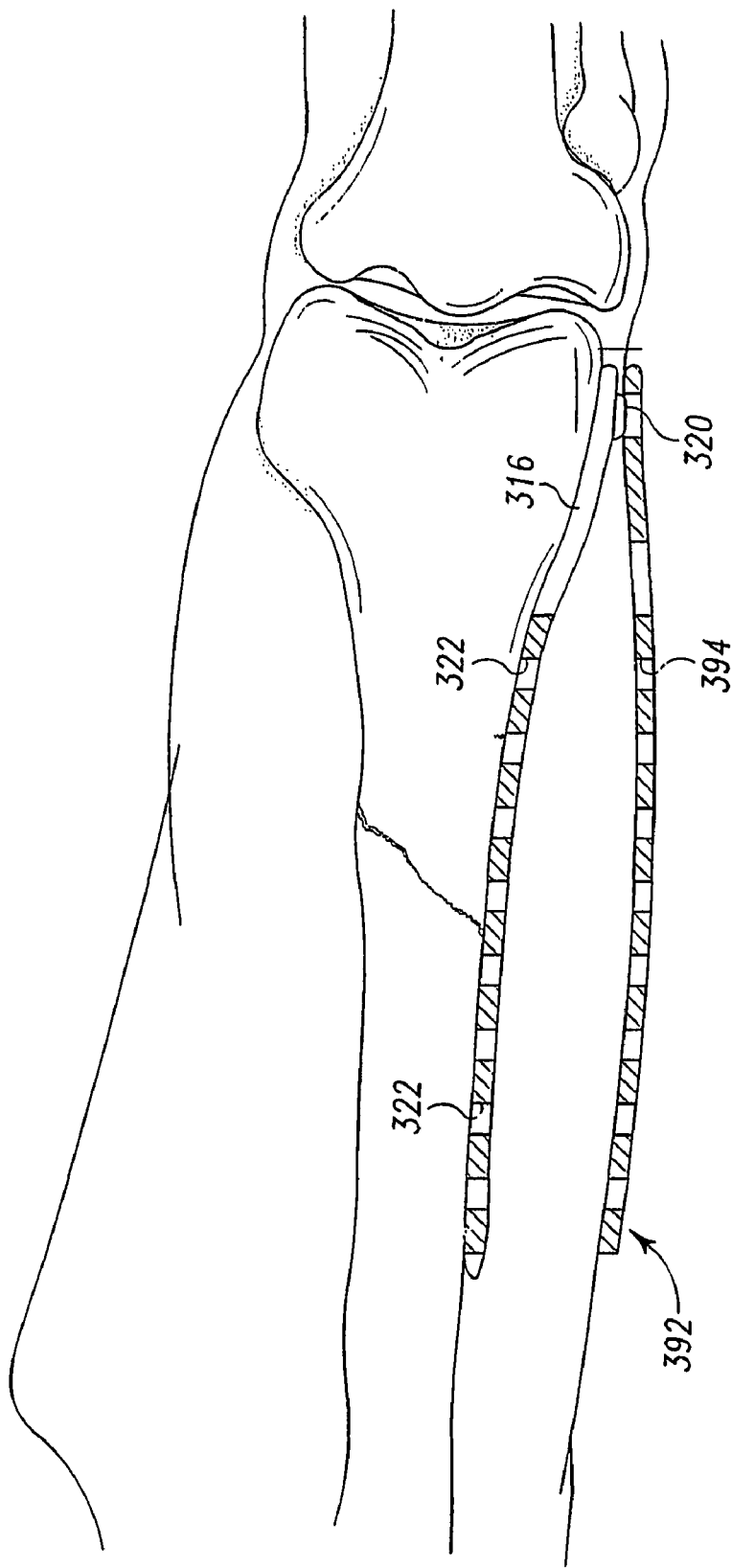
FIG. 26 is a diagrammatic plan view which shows a template for use during screw insertion, note that the template and the bone plate are shown in cross section for clarity of description.

Another device 392 which utilizes certain features of the present disclosure is shown in FIG. 26. This screw alignment device 392 is embodied as a flexible guide which may be secured or "keyed" off of one of the bone screws 320 which has been installed in the bone plate 316. In doing so, a number of holes 394 defined in the alignment device 392 are aligned with the remaining holes 322 defined in the bone plate 316.

Figure 36:
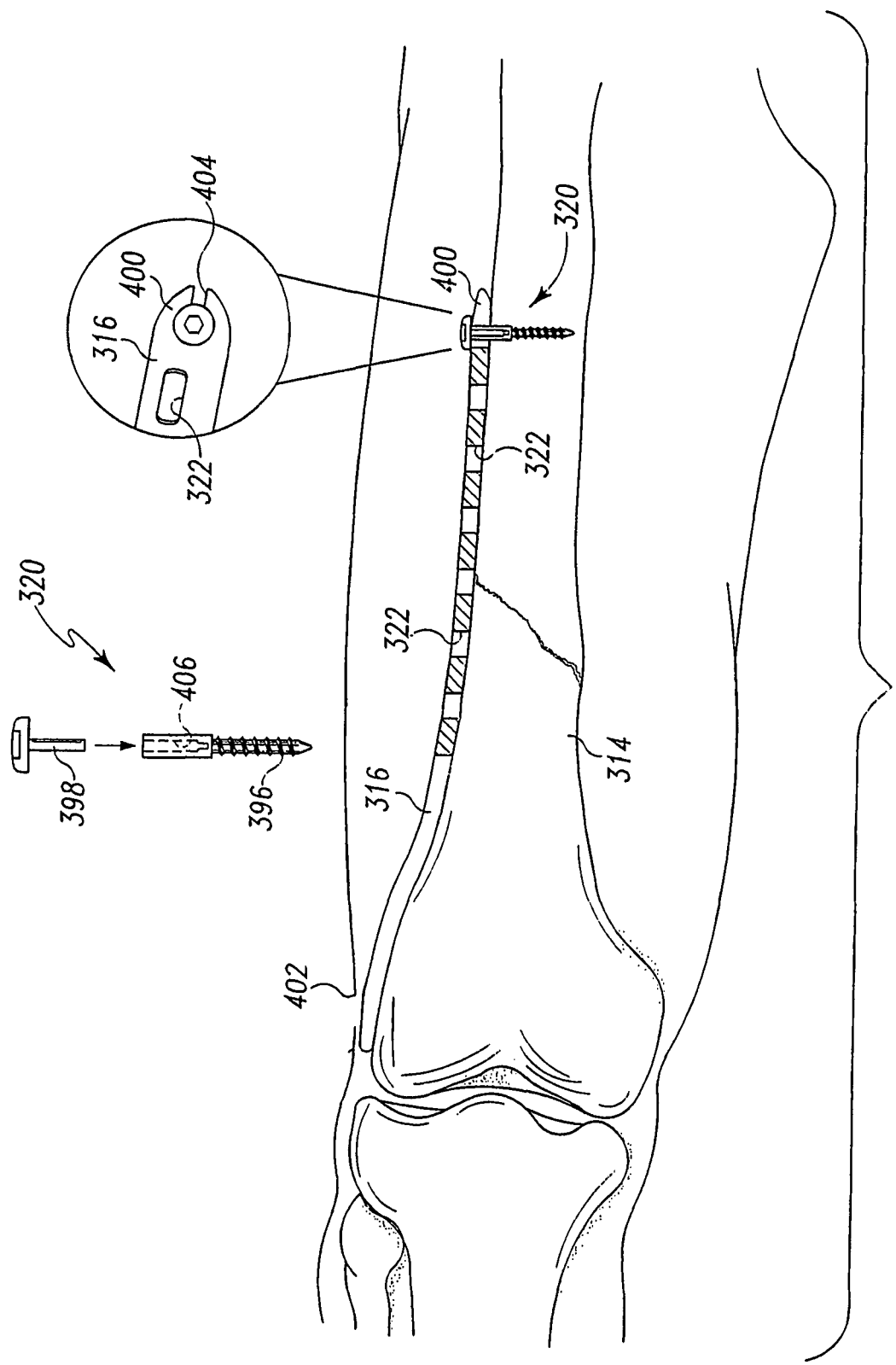
FIG. 36 is an exploded diagrammatic view which shows a locating assembly being utilized to position a bone plate in a desired implant location.

One manner of providing a bone screw 320 for such a "keying" function is shown in FIG. 36 in which the bone screw 320 is provided as an assembly having a threaded component 396 and a compression component 398. The threaded component 396 is first threadingly implanted into the fractured bone 314 via a stab incision as described above. The threaded component 396 is implanted at a location which corresponds to a desired location of the distal tip 400 of the bone plate 316. In particular, the distal tip of the plate 316 is slid or otherwise advanced through a small incision 402 and advanced along the bone 314 to a point in which the threaded component 396 of the bone screw 320 is captured or otherwise received into a slot 404 defined in the bone plate 316. Once the threaded component 396 is positioned in the slot 404, the compression component 398 may be advanced through the hole 324 in the tissue expander 308 and into a bore 406 defined in the head of the implanted threaded component 396. Advancement of the compression component 398 into the bore 406 of the threaded component 396 forces the distal tip 400 of the bone plate 316 downwardly into contact with the surface of the bone 314 thereby vertically aligning the plate 316. It should be appreciated that the alignment bone screw 320 may be left in the bone 314 or removed after the remaining bone screws 320 have been secured within the holes 322 of the plate 316 in one of the numerous manners described herein.

Referring now to FIG. 30, there is shown one of the holes 324 of the tissue expander 308 in greater detail. Although the hole 324 is shown in FIG. 30 in the context of the spoon 310, it should be appreciated that the holes 324 of the tunnel 312 may be constructed in a similar manner. As shown in FIG. 30, the hole 324 defined in the tissue expander 308 has a chamfered portion 346. Such a feature functions as a "lead-in" which facilitates the advancement of instruments (e.g., drills, taps, or even the screws 320) through the hole 324. Moreover, the hole 324 extends through a boss 348 which, for example, may be integrally molded with the tissue expander 308 (i.e., either the spoon 310 or the tunnel 312). Use of the boss 348 provides a structure of sufficient length and rigidity to allow proper alignment of instruments (e.g., drills, taps, or even the screws 320) during advancement of the same through the hole 324.

As shown in FIG. 21, a remotely controllable (i.e., from a control mechanism (not shown) associated with the handle 304) cover 350 may translate within the elongated cannulated shaft 306 (which, in this case has a plurality of holes 324 defined therein). The cover 350 prevents fat or other types of tissue from entering the workspace inside the tissue expander 308. In the specific exemplary embodiment shown in FIG. 21, the remotely controlled cover 350 is secured to the movable endoscope 330.

Such protection from the entry of unwanted tissue may also be provided by other structures. For example, as shown in FIG. 31, a flexible seal 352 constructed of, for example, silicon may cover the entrance to the hole 324. The seal 352 prevents the entry of fat or other tissue into the hole, but yet may be relatively easily pierced by instruments during advancement thereof into the hole 324.

As shown in FIG. 25, the upper surface 356 of the tissue expander 308 may be configured to include a number of illumination devices such as light emitting diodes (LED's) 354. The LED's 354 may be utilized to illuminate portions of the workspace (e.g., the holes 322 in the bone plate 316 during screw insertion) during a procedure. Such use of the LED's 354 is particularly useful for use with an endoscope 330 constructed with a CMOS chipset (such as in the case of the CMOS-based design of the endoscope shown in FIG. 25). It should be appreciated that the upper surface 356 (or the other inner surfaces of the tissue expander 308) may be configured as optical lenses or other similar structures to intensify the light generated by the LED's 354 in a number of different directions. For example, in addition to directing light onto the workspace, the configuration of the inner surfaces of the tissue expander 308 may direct intensified light outwardly through the underlying tissue and skin of the patient to provide an external indication of the location of the tissue expander 308. Such "trans-illumination" may be useful to supplement or perhaps even replace the use of the screw alignment device 318 during screw insertion.

The concepts of the present disclosure also provide for the lateral and vertical alignment of the bone plate 316 prior to securing the plate 316 to the fractured bone 314. For example, as shown in FIG. 23, a leading edge 414 of the tissue expander 308 may be configured to conform to the contour of the fractured bone 314. Such a feature assists in the centering of the tissue expander 308 onto the fractured bone 314 when the plate 316 is secured thereto. As shown in FIG. 21, extended side wings 416 may also be utilized in the construction of the tissue expander 308 in order to provide similar functionality. It should be appreciated that although the spoon 310 is shown in FIGS. 21 and 23, similar features (i.e., a contoured leading edge 414 or the use of extended side wings 416) may be utilized in the design of the tunnel 312.

Other configurations of plate alignment features are also contemplated for use in the design of the tissue expanders 308. For example, the spoon 310 or tunnel 312 may be adapted to "grab" around the outer periphery of the fractured bone 314 to assist in aligning the instrument 300, and hence the plate 316 positioned thereunder, over the center axis of the bone 314. It should be appreciated that such engagement or "grabbing" of the bone would also allow the surgeon to selectively release the handle 304 thereby permitting a certain degree of "hands free" operation of the plating instrument 300.

As shown in FIG. 19, additional "hands free" operation may be achieved by use of features associated with the housing 302, specifically the handle 304. For example, a number of lateral extensions 444 may be provided to support the plating instrument 300 against, for example, the patient's leg, an operating table, or the like. Such extensions 444 may take on the form of wings, legs, or any other type of similar structure. During a procedure, the surgeon may utilize the lateral extensions 444 to engage a support structure thereby allowing the surgeon to release the handle 304 to perform other tasks.

Figure 49:
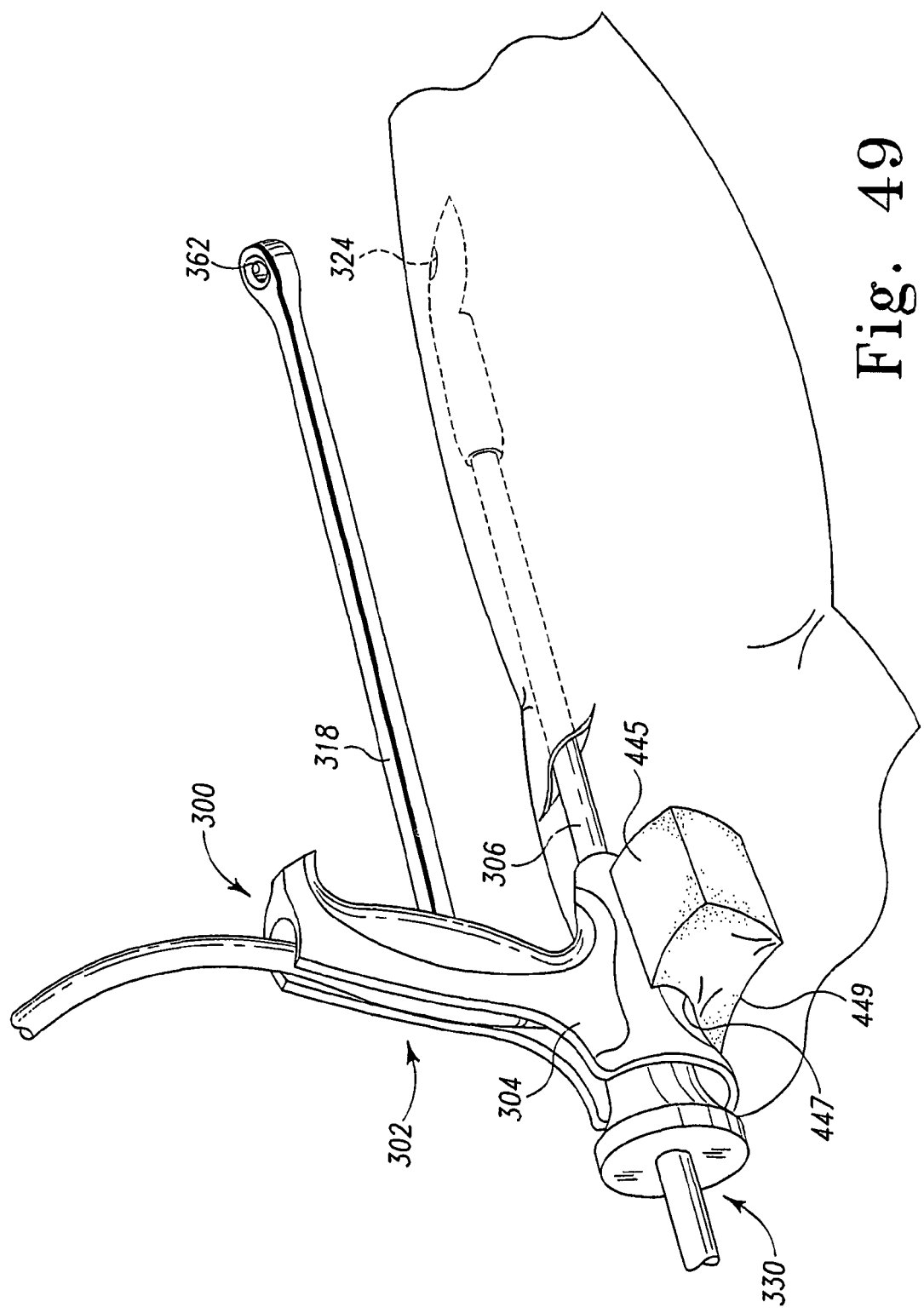
FIG. 49 is a perspective view showing the plating instrument being supported by a support block.

Other support mechanisms may also be utilized to support the plating instrument 300 during a procedure (e.g., to provide for "hands free" operation). For example, as shown in FIG. 49, a support block 445 may be secured to the an outer surface of the patient's body (e.g., the patient's leg). The plating instrument 300 may be supported by the support block 445 thereby eliminating the need for the surgeon (or other personnel) to support the plating instrument 300. In the exemplary embodiment shown in FIG. 49, the support block 445 is constructed from a deformable material (e.g., foam) with a channel 447 formed therein. The housing 302 of the plating instrument 300 is positionable in the channel 447. A lower surface 449 of the support block 445 is secured to the patient (or other surface, if desired) by the use of, for example, an adhesive. In such a way, use of the support block 445 allows the surgeon to release the handle 304 of the plating instrument 300 to perform other tasks.

As shown in FIG. 24, the tissue expander 308 may also have a slot 418 defined therein. The slot 418 extends from the hole 324 to the outer edge of the tissue expander 308. Use of the slot 418 allows the tissue expander 308 to be removed from the body of the patient while a K-wire, alignment screw, or the like that is being utilized to align the plate to the bone 314 is left secured to the bone 314. Specifically, the K-wire or alignment screw may be advanced through the hole 324 in the tissue expander 308 in the manner described above and thereafter left in place during subsequent movement of the tissue expander 308 by sliding the implanted K-wire or alignment screw through the slot 418.

Figure 32:
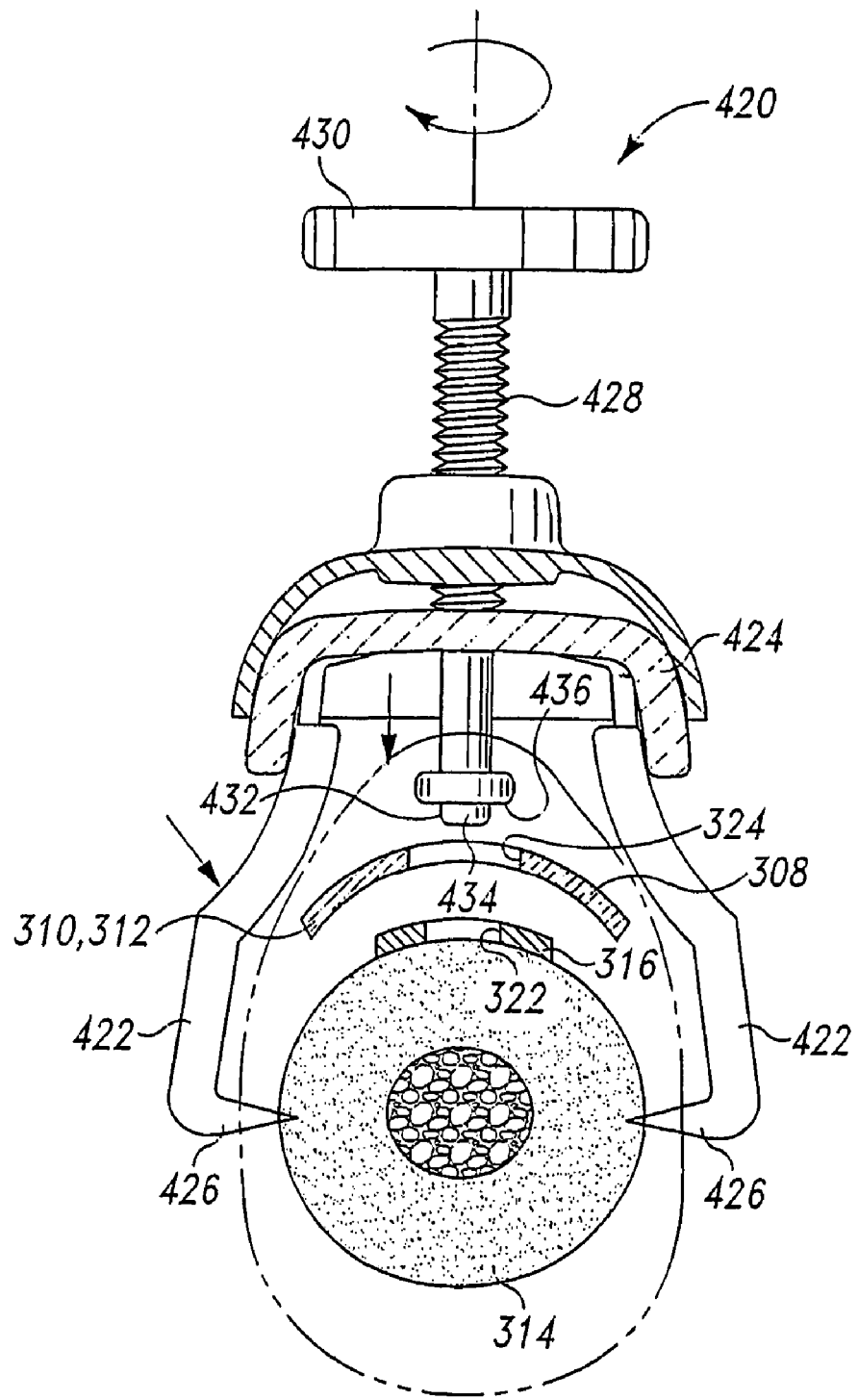
FIG. 32 is a diagrammatic elevational view of a bone clamping assembly.

As shown in FIG. 32, a separate bone clamp assembly 420 may be provided for use with the tissue expanders 308 (i.e., the spoon 310 or the tunnel 312). The clamp assembly 420 includes a pair of arms 422 pivotally coupled to a frame 424. The distal end of each arm 422 has a barb 426 defined therein which is capable of penetrating the skin, underlying tissue, and thereafter engaging the outer surfaces of the fractured bone 314. A biasing member 428 threadingly engages the frame 424 and, as a result, is movable upwardly and downwardly (as viewed in the orientation of FIG. 32) by rotation of a handle 430 in one direction or the other.

In order to center the bone plate 316 over the fractured bone 314, the surgeon positions the clamp assembly 420 externally over the bone 314 and thereafter advances the arms 422 inwardly toward one another. The surgeon continues advancement of the arms 422 such that the barbs 426 pierce the skin, penetrate the underlying tissue, and engage the outer surfaces of the bone 314. The surgeon may then turn the handle 430 so as to advance the biasing member 428 downwardly (as viewed in the orientation of FIG. 32) through the skin and underlying tissue via a previously created stab incision. The distal tip 432 of the biasing member 428 is advanced through the hole 324 in the tissue expander 308 and into the workspace created thereby. The distal tip 432 is then advanced into contact with the top of the plate 316 in order to bias the plate 316 firmly against the bone 314. In a specific exemplary embodiment, an extension portion 434 of the tip 432 of the biasing member 428 may be advanced into one of the holes 322 in the plate 316 with a shoulder portion 436 of the tip 432 engaging the upper surface of the plate 316.

Figure 37:
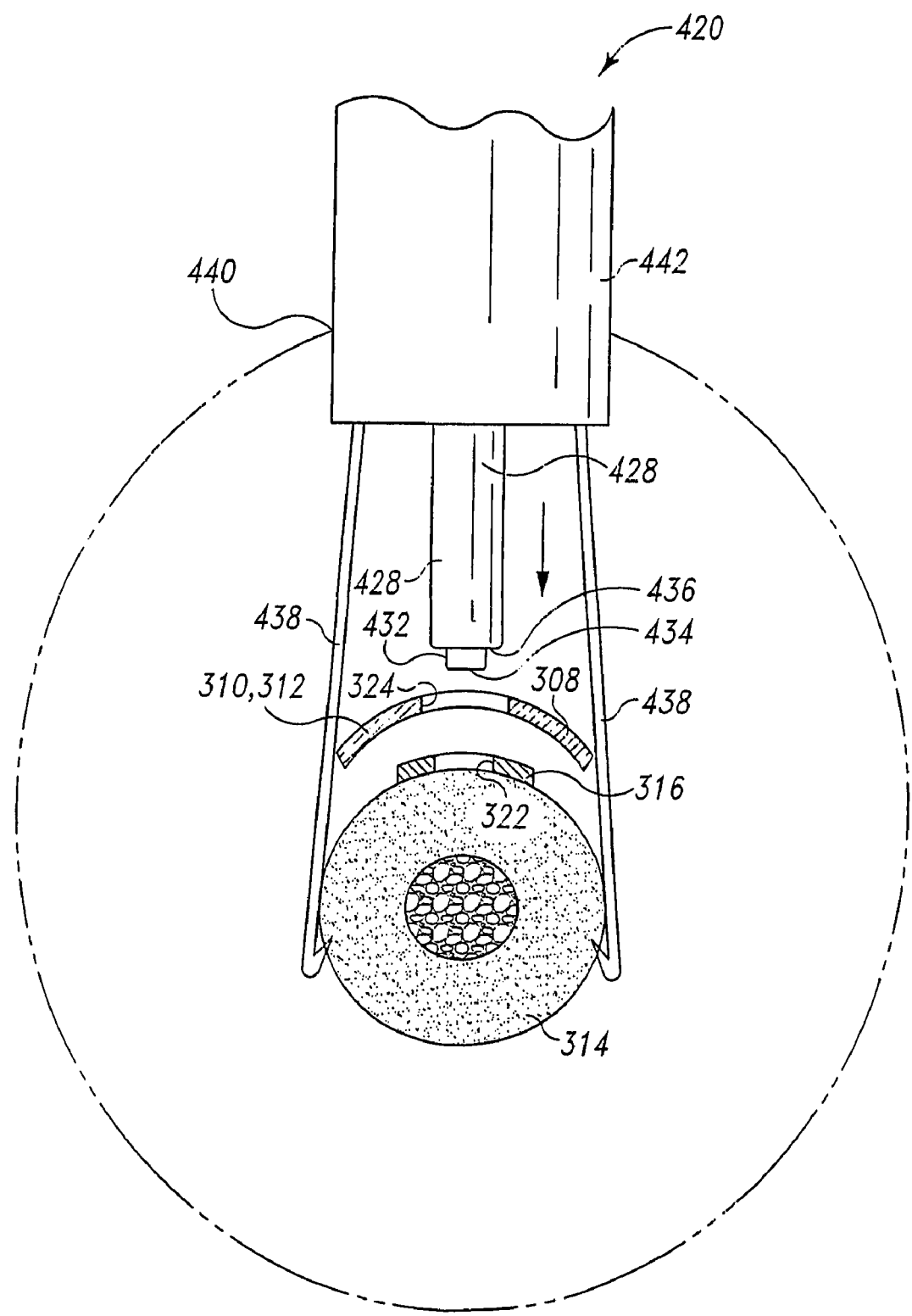
FIG. 37 is a view similar to FIG. 32, but showing a different embodiment of a bone clamping assembly.

As shown in FIG. 37, the design of the clamp assembly 420 may be modified to include a pair of flexible, spring biased arms 438 secured to a frame (not shown) within a tube 442. The flexible arms 438 may be brought together by use of the tube 442. Specifically, when the tube 442 is moved upwardly (as viewed in the orientation of FIG. 37), the arms 438 are spread outwardly in a direction away from one another. However, when the tube assembly 442 is advanced downwardly (as viewed in the orientation of FIG. 37), the arms 438 are urged toward one another and, as a result, may be inserted through a stab incision 440. The arms 438 may then be spread away from one another (i.e., by movement of the tube 442), advanced around the bone 314, and then moved toward one another (i.e., by movement of the tube 442 in the opposite direction) so as to engage the outer surfaces of the bone 314, as shown in FIG. 37.

A biasing member 428, similarly to as previously described in regard to the assembly 420 of FIG. 32, may then be utilized to bias the bone plate 316 downwardly into contact with the bone 314. Specifically, the distal tip 432 of the biasing member 428 may be advanced through the hole 324 in the tissue expander 308 and into the workspace created thereby. The distal tip 432 is then advanced into contact with the top of the plate 316 in order to bias the plate 316 firmly against the bone 314. In particular, the extension portion 434 of the tip 432 of the biasing member 428 may be advanced into one of the holes 322 in the plate 316 with the shoulder portion 436 of the tip 432 engaging the upper surface of the plate 316.

It should be appreciated that other mechanisms may also be utilized to exert a downward bias on the bone plate 316. For example, a number of inflatable bladders may be mounted on the anterior surface of the spoon 310 or tunnel 312. Such bladders are remotely inflatable with air, saline, or other fluids. As such, when the spoon 310 or tunnel 312 is positioned over the plate 316 and the fractured bone 314, the inflated bladders exert a bias against the plate 316 which urges the plate 316 into firm contact with the bone 314.

Figure 27:
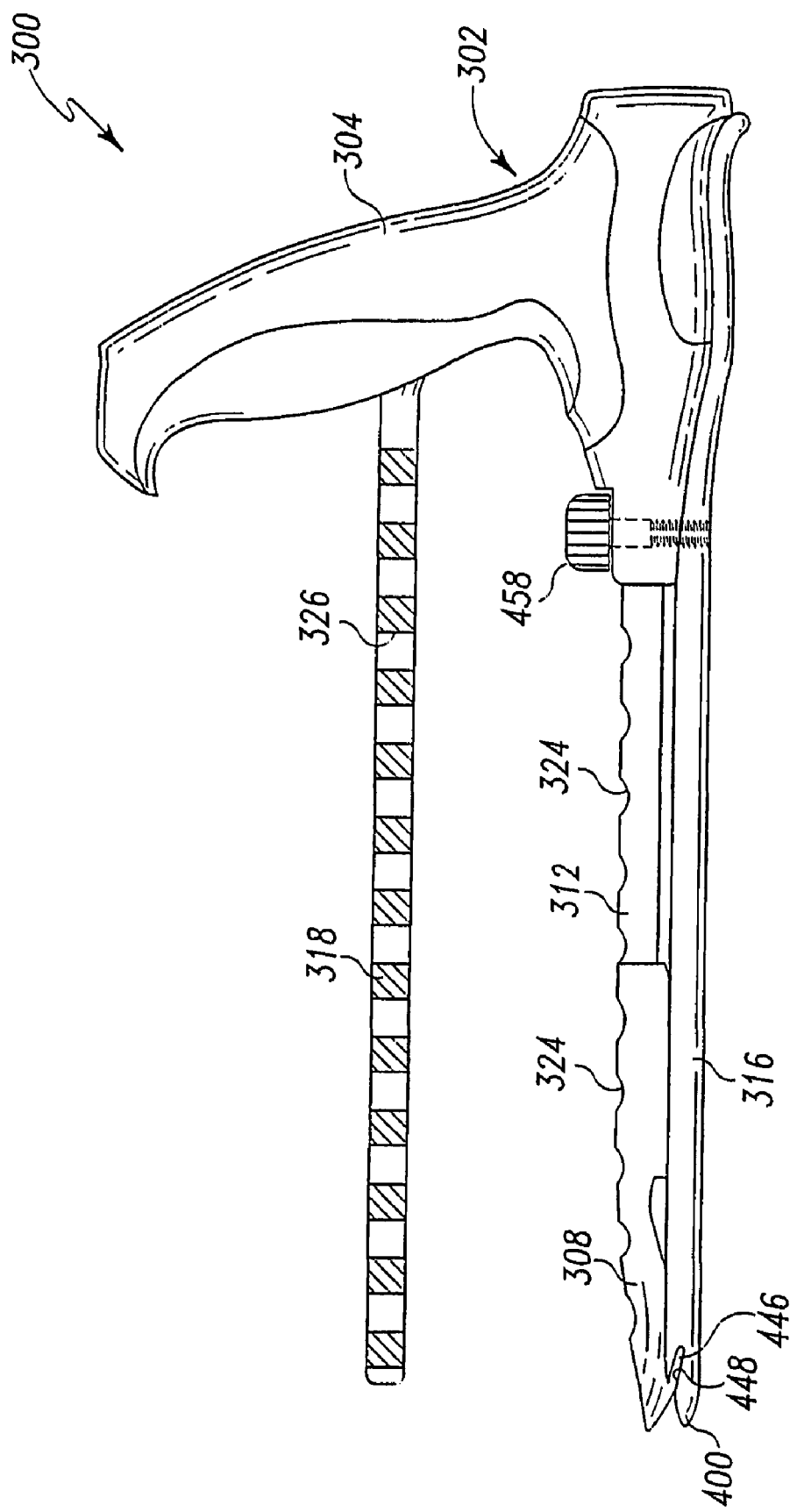
FIG. 27 is a side elevational view which shows a feature which may be utilized to secure the bone plate to the plating instrument.
Figure 29:
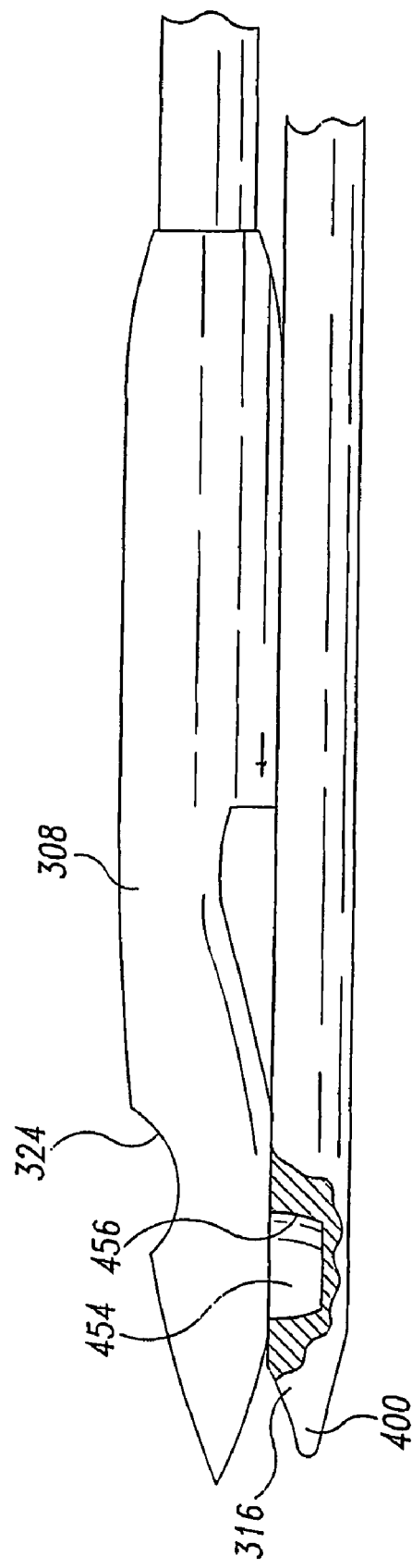
FIG. 29 is a fragmentary elevational view similar to FIG. 27, but showing another feature which may be utilized to secure the bone plate to the plating instrument.
Figure 35:
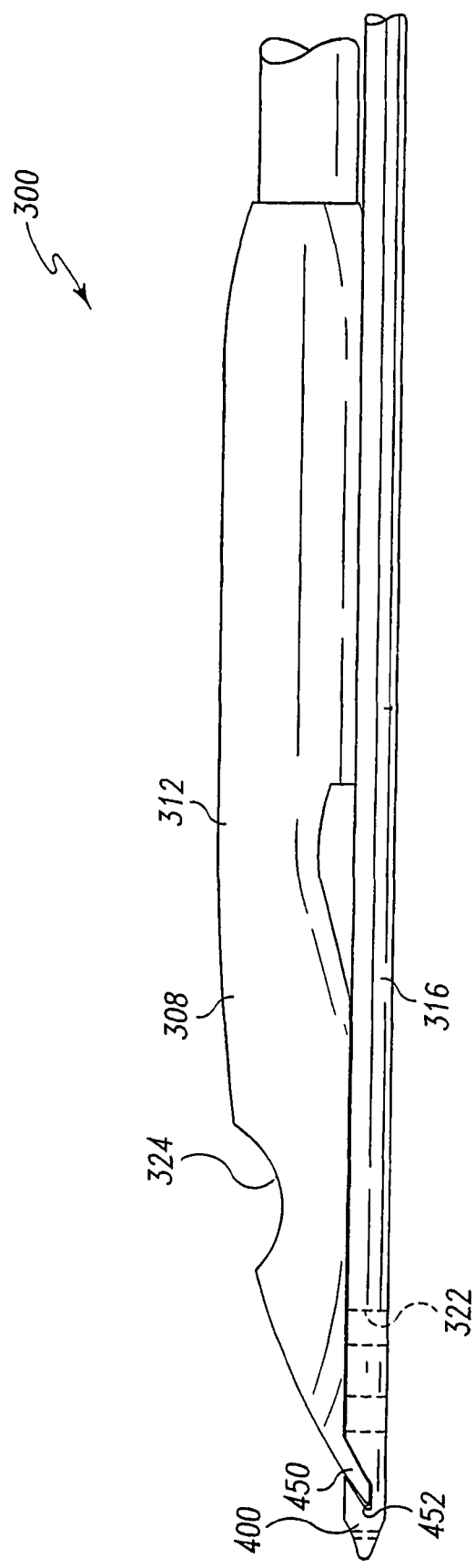
FIG. 35 is a fragmentary elevational view similar to FIG. 27, but showing another feature which may be utilized to secure the bone plate to the plating instrument.

The concepts of the present disclosure may also be utilized to "deliver" the bone plate 316 to a desired location along the bone 314. For example, as shown in FIGS. 27, 29, and 35, the tissue expanders 308 (either the spoon 310 or the tunnel 312) may have a feature defined therein which is utilized to engage the bone plate 316 near the distal tip 400 thereof. Such a feature may take the form of a rearwardly facing flange or lip 446 which is received into a corresponding slot 448 defined in the bone plate 316 (see FIG. 27). Such a feature may also take the form of a forwardly facing flange or lip 450 which is received into a corresponding slot 452 defined in the bone plate 316 (see FIG. 35). Alternatively, such a feature may take the form of a protrusion, detent, or tab 454 which is received into a corresponding recess 456 defined in the bone plate 316 (see FIG. 29).

As described, such features support the distal end of the plate 316. To support the other end of the plate 316 (i.e., the proximal end), a removable fastener 458 is provided (see FIG. 27). The fastener 458 is received through a bore defined in the housing 302 and thereafter threadingly engages the proximal end of the bone plate 316 thereby allowing the plate 316 to be removably secured to the plating instrument 300.

Once positioned in a desired position, one or more bone screws 320 may be inserted through the plate 316 and into the bone 314 to initially secure the plate 316 in the desired location. The surgeon may then remove the fastener 458 and thereafter manipulate the instrument 300 so as to release the distal tip 400 of the plate 316 (i.e., remove the lip from the associated slot or the tab from the associated recess). Once done, the surgeon may then insert the remaining bone screws 320 in the manner described above.

Figure 34:
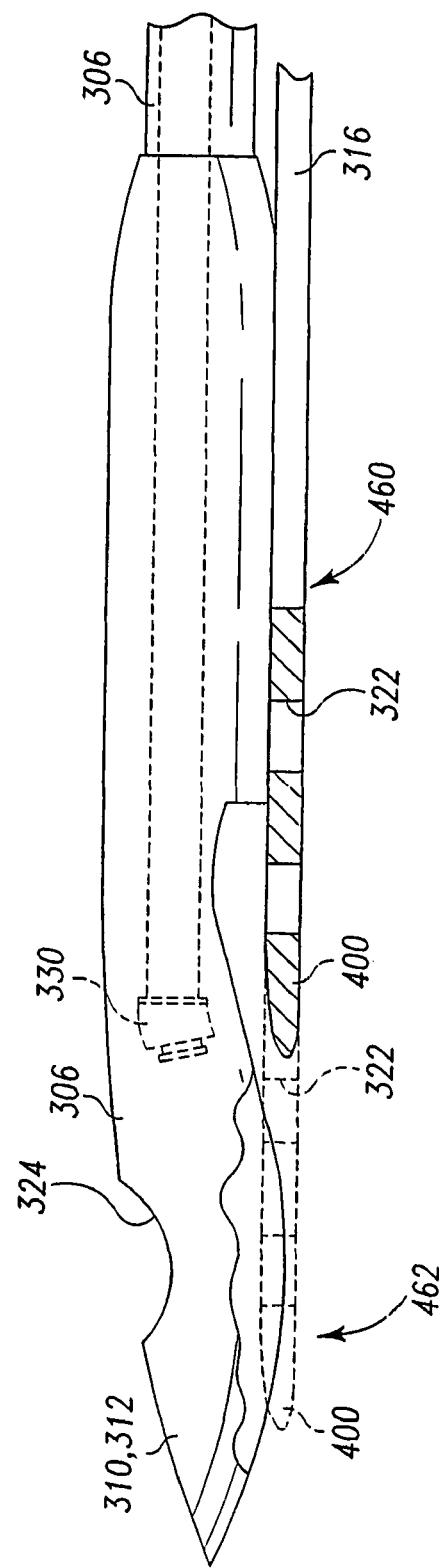
FIG. 34 is a diagrammatic side elevational view which shows the different positions in which the bone plate may be positioned during delivery thereof.
Figure 41:
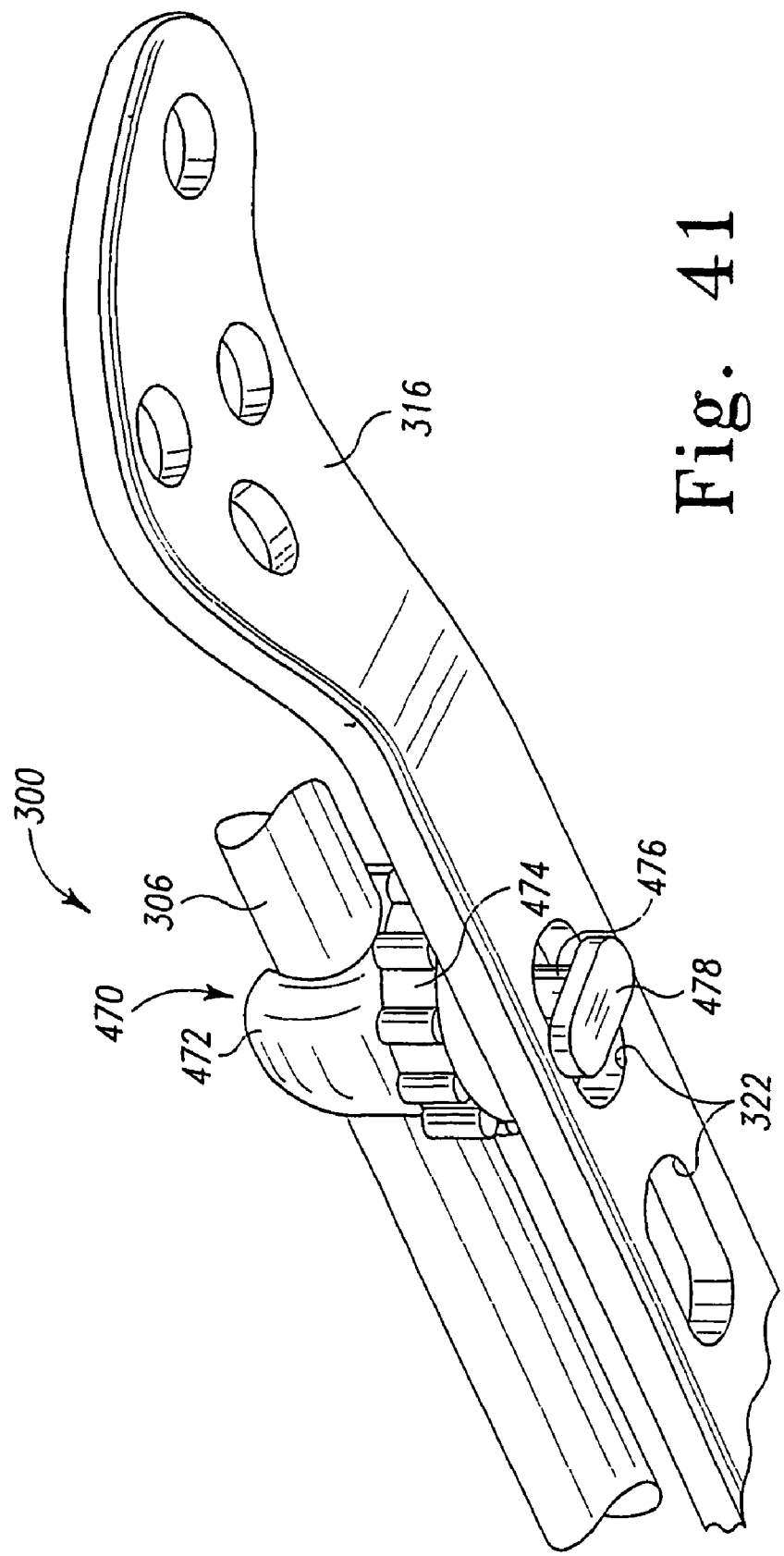
FIGS. 41-43 are fragmentary perspective views of plate attachment and delivery mechanisms for securing the bone plate to the plating instrument.

Other exemplary embodiments of plate attachment and delivery mechanisms are shown in FIGS. 41-48 and 50-52. As shown in FIG. 41, the plating instrument 300 may be embodied to include a plate attachment and delivery mechanism 470. The mechanism 470 includes a saddle 472 that is movably secured to the plating instrument 300. In the exemplary embodiment shown in FIGS. 41-43, the saddle 472 is slidable along the shaft 306 of the plating instrument 300. Such mobility (e.g., slidability) allows the position of the bone plate 316 to move relative to the plating instrument 300 during implantation thereof. In such a manner, the bone plate 316 may be positioned in a temporary delivery position during advancement of the plate 316 into the body. For example, as shown in FIG. 34, the plate 316 may be retained in a delivery position (indicated generally at 460 in FIG. 34) during insertion into the incision and advancement through the underlying tissue to the desired position along the fractured bone 314. Positioning the plate 316 in such a position prevents the plate 316 from obstructing the view of the endoscope 330 thereby allowing full use of the endoscope 330 during navigation of the instrument 300 to the delivery site.

The saddle 472 has a thumbwheel 474 rotatably secured thereto. A first end of a shaft 476 is secured to the thumbwheel 474 and extends downwardly therefrom. The other end of the shaft 476 has a flange 478 secured thereto. As such, rotation of the thumbwheel 474 causes rotation of the flange 478.

The mechanism 470 is operable to secure the bone plate 316 to the plating instrument 300. In particular, the flange 478 may be positioned in a release position which allows the flange 478 to be advanced through one of the holes 322 in the bone plate 316 (the release position of the flange 478 being approximately 90° from the position of the flange 478 shown in FIG. 41). Once the flange 478 is advanced through the hole 322 (i.e., the shaft 474 extends through the hole 322), the thumbwheel 474 may be rotated such that the flange 478 is positioned in a locked position (such as shown in FIG. 41) thereby causing the bone plate 316 to be secured to the plating instrument 300. In such a manner, the bone plate 316 may be delivered to a desired location proximate to the fractured bone 314, and thereafter released prior to, or during, bone screw insertion.

Figure 42:
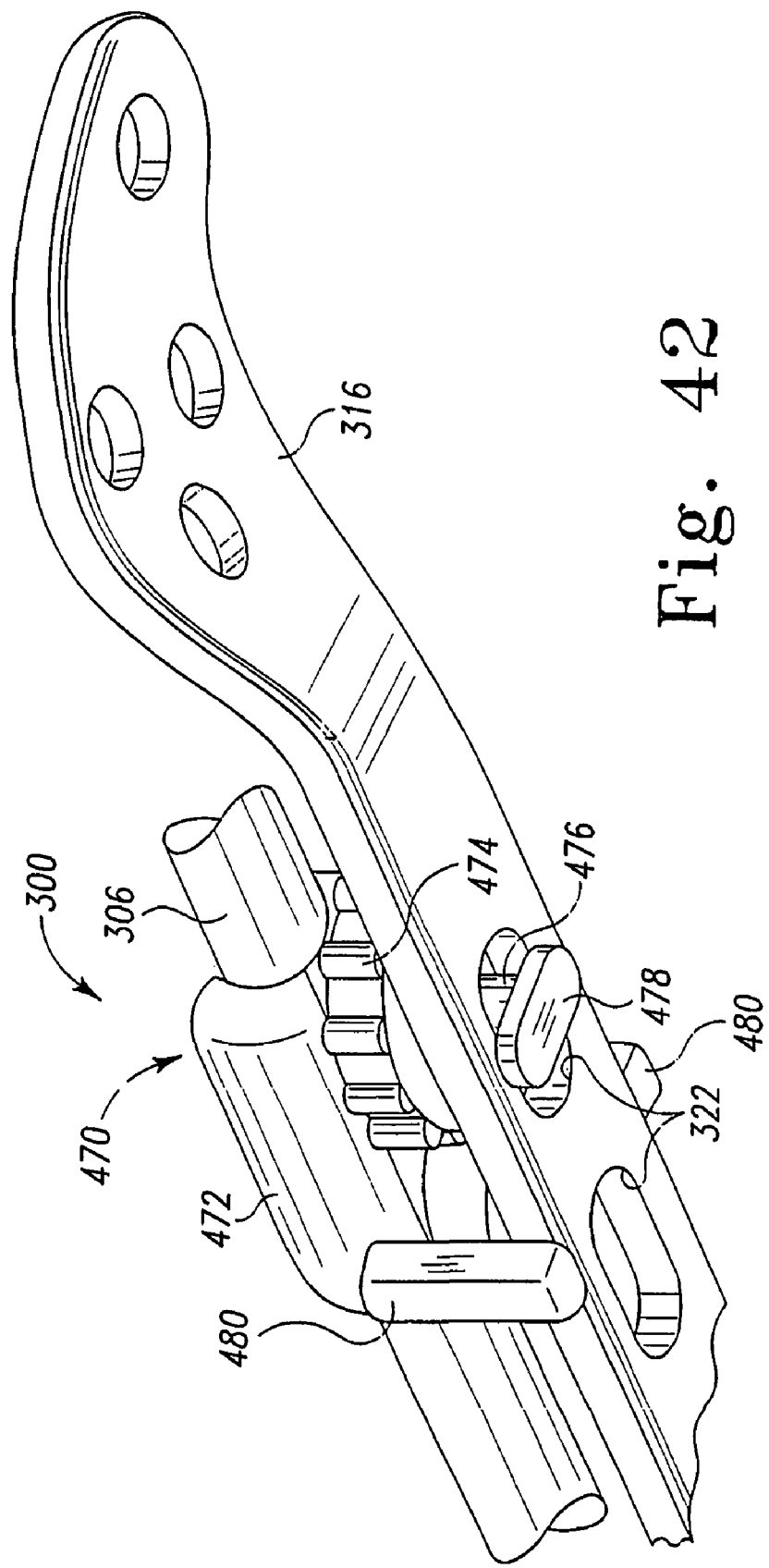
Figure 43:
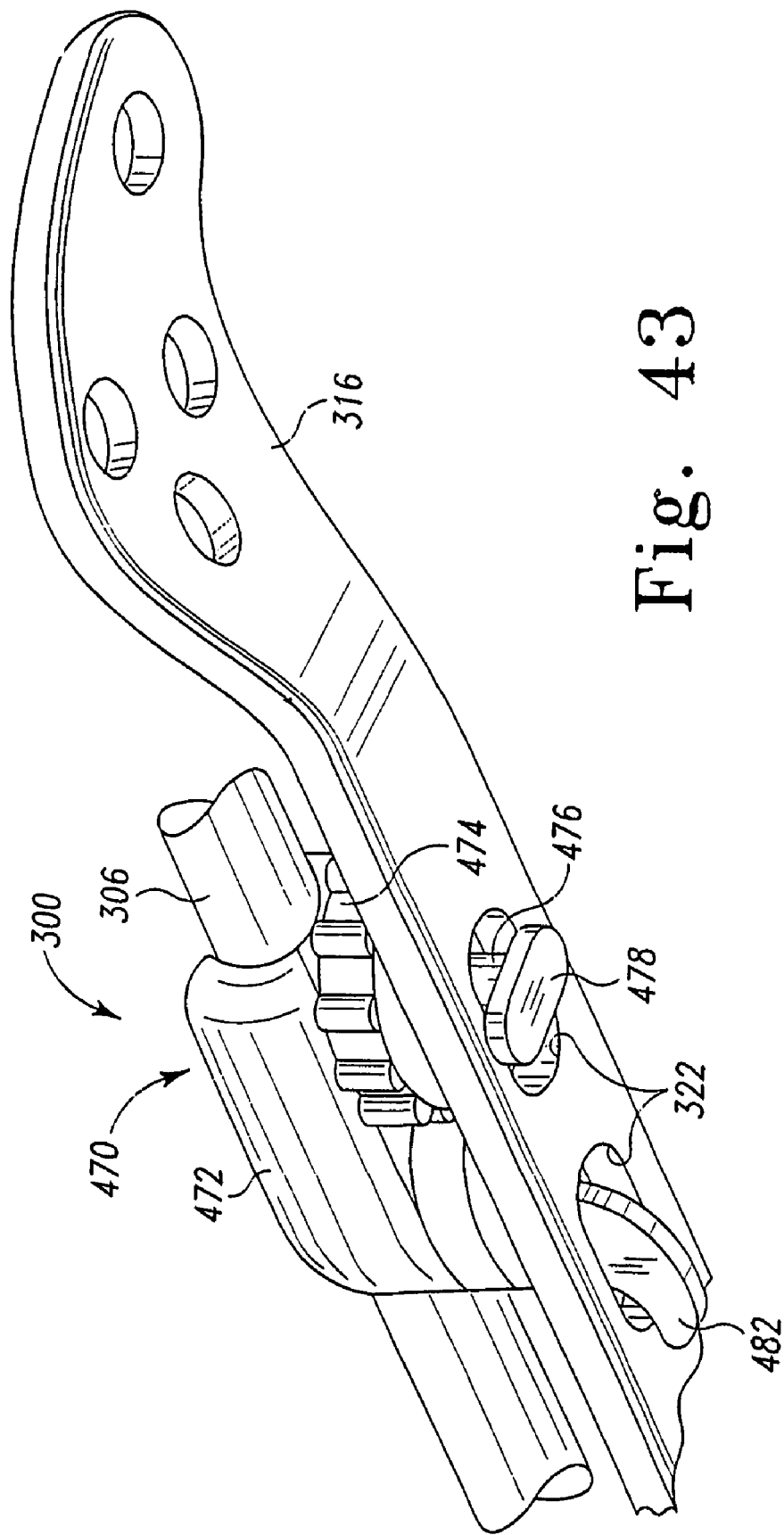

As shown in FIGS. 42 and 43, the mechanism 470 may also be configured to include a number of alignment features for aligning the bone plate 316 in a desired lateral and/or longitudinal orientation relative to the bone plating instrument 300. For example, as shown in FIG. 42, the attachment mechanism 470 may be embodied to include a pair of downwardly extending locator tabs 480. The plate 316 is positioned between the locator tabs 480 when the plate is secured to the plating instrument 300 thereby maintaining the plate 316 in a desired lateral orientation. The attachment mechanism 470 may also be configured to include a downwardly extending flange in the form of a hook 482 (see FIG. 43). The hook 482 is received through one of the holes 322 in the bone plate 316 when the bone plate 316 is secured to the plating instrument 300. In such a way, the bone plate 316 may be maintained in a desired longitudinal orientation. It should be appreciated that the design of the attachment mechanism 470 may be varied to include any one or more of the afore-described alignment features, or may alternatively, be configured without any of the alignment features (such as shown in FIG. 41).

It should be appreciated that other types of retention mechanisms may also be utilized to secure the plate 316 to the instrument 300 during delivery of the plate 316. For example, a remotely controllable clasping or gripping assembly may be utilized to engage the plate 316 during delivery thereof to a desired location. For example, as shown in FIGS. 44-49 and 50-52, the plating instrument 300 may be configured to include an attachment and delivery mechanism 490.

Figure 44:
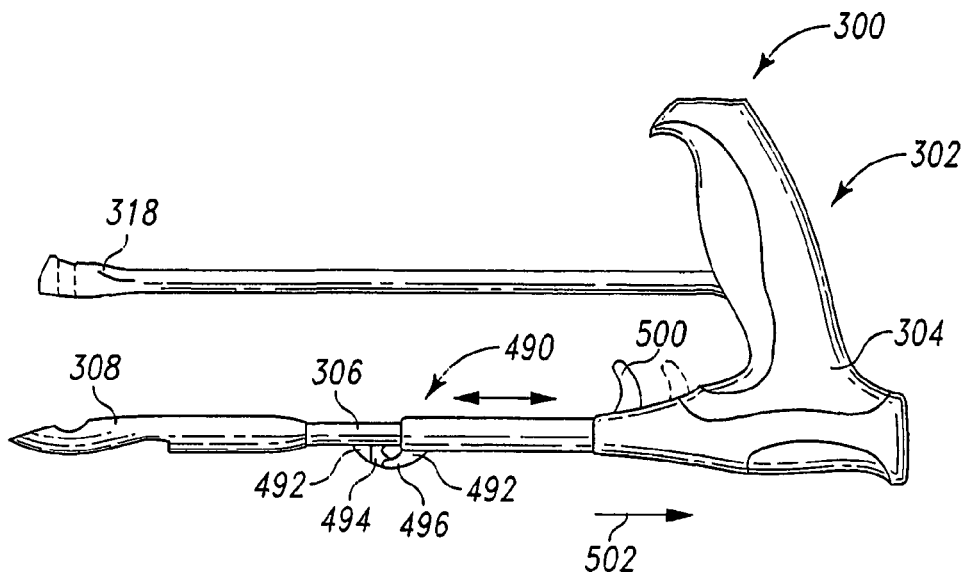
FIG. 44 is a side elevational view of a plating instrument having a plate attachment and delivery mechanism which utilizes two hooks to secure the bone plate to the plating instrument.
Figure 45:
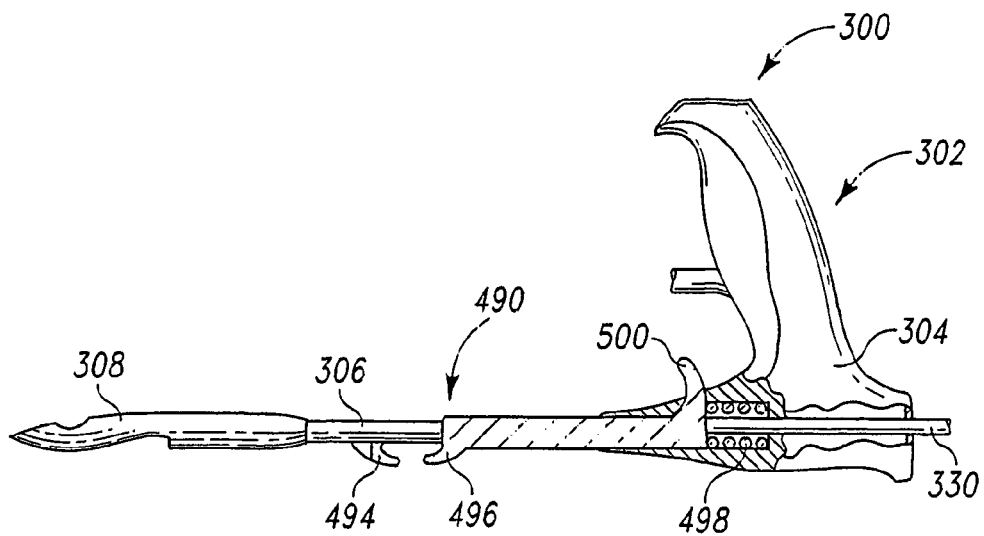
FIG. 45 is a side elevational view similar to FIG. 44, but showing the hooks in spaced apart relation relative to one another, note that a portion of the instrument is shown in cross section for clarity of description.

The mechanism 490 includes a number of downwardly extending flanges 492 which, in the case of the exemplary embodiments described herein, are embodied as a pair of hooks 494, 496. The hooks 494, 496 are movable relative to one another. In particular, as shown in FIGS. 44 and 45, the hooks 494, 496 may be slid or otherwise moved relative to one another. More specifically, as shown in FIG. 44, the hooks 494, 496 may be positioned at a relative close distance to one another, or may be spaced apart from one another as shown in FIG. 45. A spring 498 (see FIG. 45) biases the hooks 494, 496 toward one another (i.e., biases the hooks into the position shown in FIG. 44). When a user (e.g., a surgeon) urges a lever 500 in the general direction of arrow 502 of FIG. 44 (i.e., in the general direction of the handle 304), the bias of the spring 498 is overcome, thereby urging the hook 496 away from the hook 494 in the general direction of arrow 502.

Figure 48:
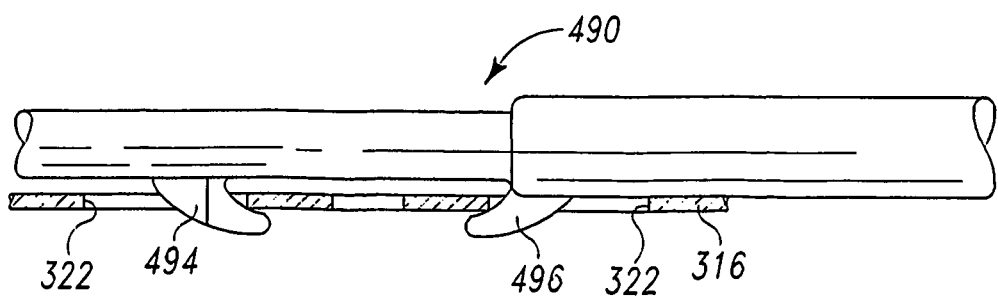
FIG. 48 is view similar to FIG. 46, but showing the hooks engaged with a bone plate, note that the bone plate is shown in cross section for clarity of description.

Such movement of the hooks 494, 496 relative to one another allows for attachment of the bone plate 316 to the plating instrument 300. In particular, as shown in FIG. 48, the surgeon may first urge the hooks 494 away from one another (i.e., to the position shown in FIG. 45) and thereafter advance the hooks 494, 496 into respective holes 322 of the bone plate 316. Thereafter, when the surgeon releases the lever 500, the bias of the spring 498 urges the hooks 494, 496 toward one another thereby causing the hooks to engage the bone plate 316 (as shown in FIG. 48) thereby securing the bone plate 316 to the plating instrument 300. The plate 316 may be released from the plating instrument 300 by again urging the lever 500 toward the handle 304 and advancing the hooks 494, 496 out of their respective holes 322.

Figure 46:
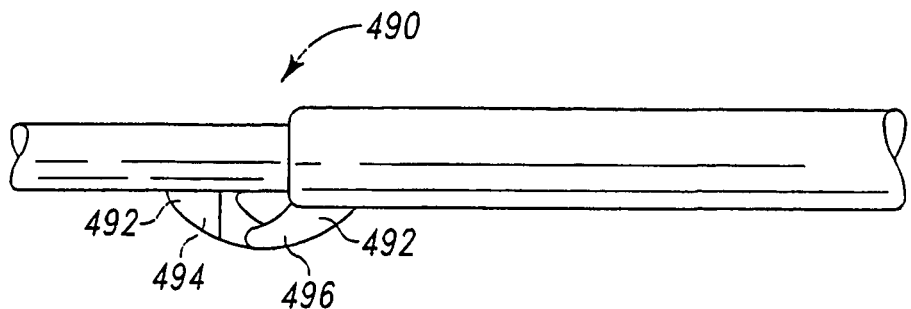
FIG. 46 is a fragmentary side elevational view of the plating instrument of FIGS. 44 and 50.
Figure 47:
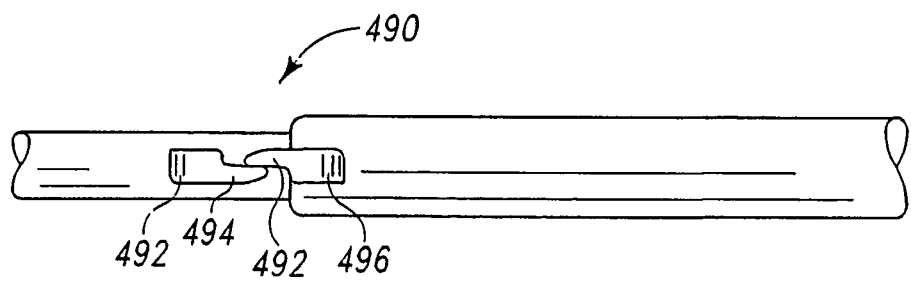
FIG. 47 is a fragmentary bottom elevational view of the plating instrument of FIGS. 44 and 50.

As shown in FIGS. 46 and 47, the hooks 494, 496 may be configured to "nest" with one another when positioned in the closed position of FIG. 44. In such a manner, the hooks 494, 496 are prevented from inadvertently engaging tissue (e.g., snagging) during manipulation of the instrument 300 in the body of the patient.

Figure 50:
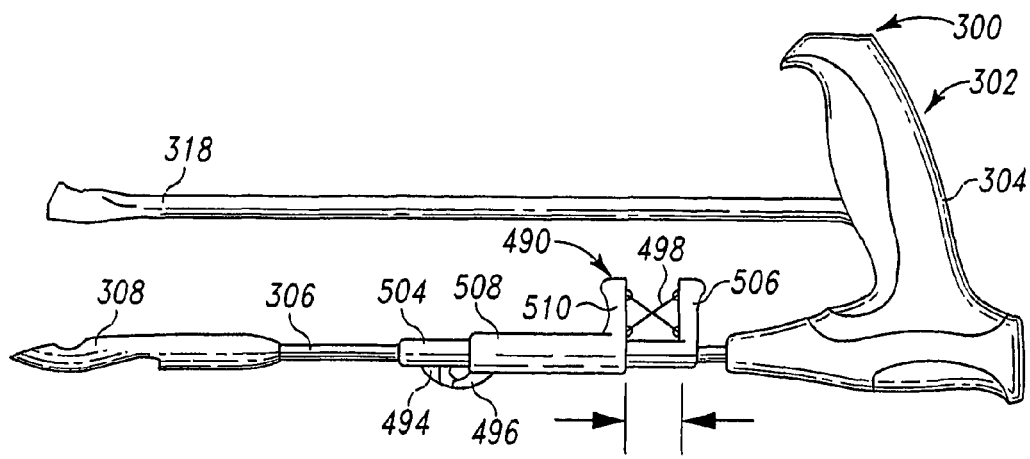
FIGS. 50-52 are views similar to FIG. 44, but showing a movable plate attachment and delivery mechanism.
Figure 51:
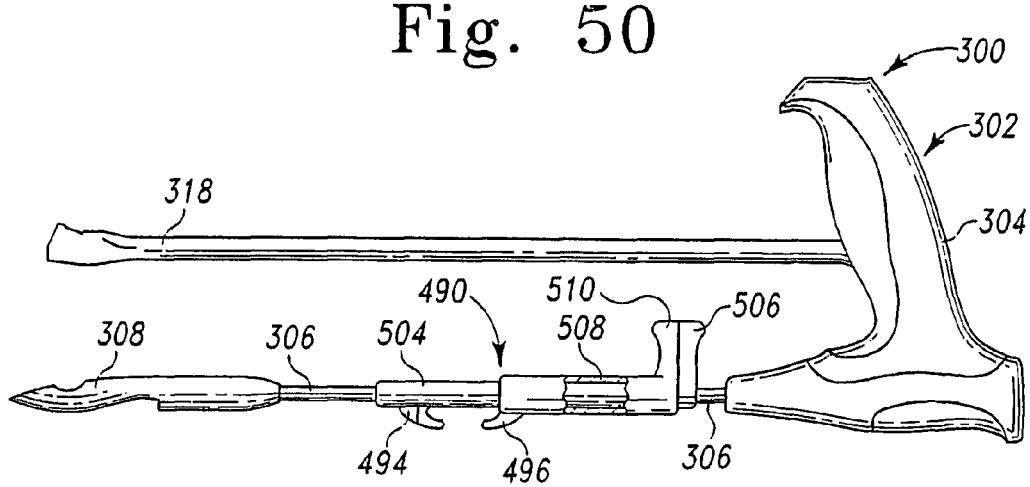
Figure 52:
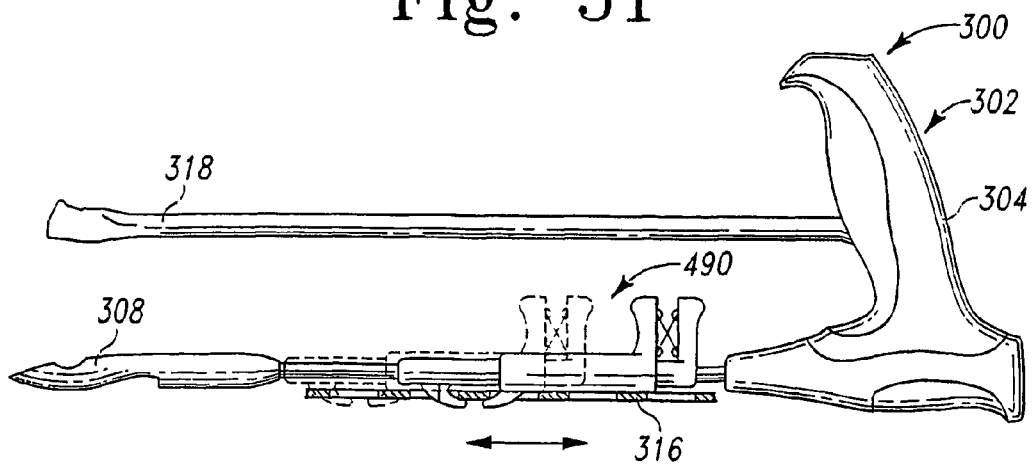

As shown in FIGS. 50-52, the attachment and delivery mechanism 490 may be configured such that the entire mechanism (including both hooks 494, 496) is movable (e.g., slidable) along the shaft 306. To do so, the hook 494 is defined in one end of an elongated, tubular shaped body 504 with a first lever 506 being defined in the opposite end of the body 504. The body 504 is cannulated and slides along the shaft 306 of the plating instrument 300. The hook 496, on the other hand, is defined in one end of an elongated, tubular body 508 with a second lever 510 being defined in the opposite end of the body 508. In a similar manner as the body 504, the body 508 is also cannulated. In such a manner, the body 508 slides along the body 504.

When the two levers 506, 510 are urged toward one another (as shown in FIG. 51), the hooks 494, 496 are urged away from one another. However, when the levers 506, 510 are released, the bias of the spring 498 urges the hooks 494, 496 toward one another (as shown in FIG. 50). As such the levers 506, 510 may be manipulated to allow the hooks 494, 496 to engage the bone plate 316 in a similar manner to as described above in regard to FIG. 48.

Moreover, the mobility of the attachment and delivery mechanism 490 of FIGS. 50-52 allows for the selective positioning of the plate 316 during implantation thereof in the manner previously described in regard to FIG. 34. By sliding the mechanism 490 along the shaft 306 (as shown in FIG. 52), the bone plate 316 may be positioned in a temporary delivery position during advancement of the plate 316 into the body. For example, as shown in FIG. 34, the plate 316 may be retained in a delivery position (indicated generally at 460 in FIG. 34) during insertion into the incision and advancement through the underlying tissue to the desired position along the fractured bone 314. Positioning the plate 316 in such a position prevents the plate 316 from obstructing the view of the endoscope 330 thereby allowing full use of the endoscope 330 during navigation of the instrument 300 to the delivery site.

Use of the aforedescribed components (e.g., the attachment and delivery mechanisms described in regard to FIGS. 27, 29, 35, 41-48, and 50-52) allows the surgeon to deliver the plate 316 during insertion of the instrument 300. Specifically, prior to insertion of the bone plating instrument 300 into the body of the patient, the bone plate 316 is secured to the instrument 300 in one of the manners described above. Thereafter, under visualization provided by the endoscope 330, the instrument 300, with the plate 316 secured thereto, is inserted through a relatively small incision and thereafter advanced beneath the underlying tissue along the length of the bone 314.

Once the instrument arrives at the location of the bone 314 to which the plate 316 is to be secured, the surgeon may remotely (e.g., by use of a control (not shown) positioned on the handle 304) advance the bone plate 316 distally to its final position against the fractured bone 314 (indicated generally at 462 in FIG. 34). It should be appreciated that the plate 316 may then be secured (e.g., screwed) to the bone 314 within full view of the endoscope 330 when positioned in its final position.

In operation, the bone plating instrument 300 may be utilized to secure the bone plate 316 to a fractured bone 314. To do so, a small incision is made in the skin overlying the fractured bone 314 to be repaired. A relatively small degree of dissection is performed which extends from the incision in the skin through the underlying incision down to the fractured bone 314.

The instrument 300 is then inserted into the incision and advanced under the visualization provided by the endoscope 330. It should be appreciated that, if so desired, the surgeon could insert the instrument 300 through a secondary incision proximate to the fractured bone 314 to be treated. In either case, the instrument 300 is then advanced along the surface of the fractured bone 314 to allow for imaging of fracture lines, fragments, surrounding tissue, or the like.

The bone plate 316 is inserted through the incision and positioned along the fractured bone 314. As described above, the bone plate 316 may be delivered to the desired location on the fracture bone 314 by the instrument 300. Alternatively, the bone plate 316 may be independently advanced to the desired location on the fractured bone once the instrument 300 is properly positioned. It should be appreciated that when so positioned, the plate 316 bridges the fracture or fractures in the bone 314.

Once the bone plate 316 has been positioned, instruments and implant devices may be advanced through the holes 322 in the bone plate 316 and thereafter into contact with the bone 314 under the visualization provided by the endoscope 330. For example, under the visualization provided by the endoscope 330, K-wires, soft tissue cannulated sleeves, drill guides and bits, tap guides and taps, screws and screw drivers may be advanced through the soft tissue and into the holes 322 of the plate 316 (and hence the portions of the bone 314 thereunder).

A number of external devices, such as the screw alignment device 318, may be utilized to guide the advancement of such instruments and implants. In addition, an integral or independent clamp assembly 420 may be utilized to further align the plate 316 prior to securing the same to the bone 314.

In such a fashion, a plurality of bone screws 320 may be installed on the bone plate 316. Once the last of such screws 320 has been installed, the plating instrument 300 may be removed. The incision may then be closed in a conventional manner.

Other Orthopaedic Procedures

The concepts of the present disclosure may also be utilized in the performance of other orthopaedic procedures. For example, the concepts of the present disclosure may also be utilized in the performance of procedures to relieve carpal tunnel syndrome. Specifically, a small, portable, preferably disposable version of the endoscopic instruments hereinbefore described may be utilized during the performance of such a procedure. Typically, a surgeon performing a carpal tunnel procedure will utilize relatively large incisions along the wrist and hand of the patient and thereafter dissect a portion of the underlying tissue. This is done, primarily, so that the surgeon may directly visualize the underlying anatomy (such as median nerve in the case of carpal tunnel) thereby preventing inadvertent damage thereto.

However, by use of an endoscopic instrument constructed in accordance with the present disclosure, the affected soft tissues may be dissected subcutaneously while under direct visualization from the endoscope. Specifically, an endoscope may be integrated into the subcutaneous scalpel assembly thereby allowing the surgeon to directly visualize the surgical site.

Similar concepts may also be utilized in regard to the performance of a procedure to relieve compartment syndrome or plantar fasciitis. For example, the concepts of the present disclosure may be utilized to eliminate the need to cut an elongated incision in an extremity of the patient. To do so, an endoscope of the type described herein my be integrated into the hook portion of a hook knife instrument thereby allowing the surgeon to manipulate the relatively long instrument up through a small incision made in the extremity under the visualization provided by the endoscope. Once present at the surgical site, the endoscope provides the visualization necessary to aid the surgeon in the cutting of the desired tissue without damaging surrounding anatomical structures.

The concepts of the present disclosure may also be utilized in regard to orthobiologics. Specifically, the concepts of the present disclosure may be utilized to deliver and place orthobiologic components such as resorbable patches and the like. For example, devices such as those devices sold under the trade names Restore™, Orthosorb™ pins, α-BSM™, and Symphony™ may be placed utilizing the concepts of the present disclosure.

The concepts of the present disclosure may also be utilized to provide direct visualization during skinny wire placement in regard to circular external fixation. Such visualization allows the surgeon to avoid neurological bundles and blood vessels.

The concepts of the present disclosure may also be utilized in the evaluation and removal of a tumor biopsy or an aneurysmal bone cyst. In particular, under the visualization of an endoscope, the surgeon may gain access to the surgical site via a trocar. Thereafter, the surgeon may evaluate the tumor or cyst by use of the endoscope, and, if need be, remove the tumor or cyst via the cannula of the trocar. Moreover, if the procedure so requires, graft material may be implanted into the surgical site via the cannula of the trocar and under the visualization of the endoscope.

Moreover, while a number of the concepts of the present disclosure have herein been described in detail in regard to delivery and installation of a bone plate, it should be appreciated that the instruments and methods described herein may also be utilized to remove a bone plate or other hardware such as screws in an IM nail or the nail itself. For example, the plating instruments described herein may be utilized to locate and remove an implanted bone plate (including the locating and removal of each of the bone screws). More specifically, the tissue expander, under the visualization of the endoscope, may be positioned over each of the bone screws. Then, under the alignment provided by the screw alignment device, the bone screws may then be removed via a series of stab incisions. Once the screws have been removed, the bone plate may then be removed from the body of the patient via the incision through which the plating instrument was inserted.

While the concepts of the present disclosure have been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus and methods described herein. It will be noted that alternative embodiments of each of the apparatus and methods of the present disclosure may not include all of the features described yet still benefit from at least some of the advantages of such features. Those of ordinary skill in the art may readily devise their own implementations of apparatus and methods that incorporate one or more of the features of the present disclosure and fall within the spirit and scope of the present disclosure.

For example, in lieu of utilizing the plating instrument 300 described herein, a trocar alone may be utilized to perform a plating operation. For example, a trocar with embedded CMOS or conventional endoscopic camera may be advanced (with a sheath) through a jig connected to the plate. The holes in the jig are in direct alignment with the holes in the plate. As the trocar/camera is passed through a stab incision, the plate and surrounding areas can be visualized. Once the surgeon is satisfied with the plate placement and proposed screw location, the trocar/camera is removed from the sheath, whereupon drills, taps, depth gauges, and screwdrivers can be used in succession to place screws. The process is repeated for each screw.

Moreover, although the endoscope 330 of the bone plating instrument 300 is herein described as being advanced through the handle 304 of the instrument 300, it should be appreciated that other configurations are also contemplated. For instance, the endoscope 330 may be advanced into the workspace created by the tissue expander 308 via a stab incision which is distinct from the incision through which the tissue expander 308 enters the body.

In a specific implementation of this exemplary embodiment, the endoscope 330 may be advanced into the body in a similar nature as the bone screws 320. Specifically, the endoscope 330 may be advanced through one of the holes 326 in the screw alignment device 318 and thereafter through one of the holes 324 in the tissue expander 308. For example, both the screw alignment device 318 and the tissue expander 308 may be configured to include a pair of holes 326, 324, respectively. The endoscope 330 may be advanced through the first hole 326 of the device 318 and the first hole 324 of the expander 308 so as to visualize the insertion of a screw driver and bone screw 320 through the second hole 326 of the device 318 and the second hole of the expander 308.

It should be appreciated that the incisions through which the endoscope 330 is advanced may be later utilized for screw insertion to avoid the creation of additional stab incisions. Specifically, the stab incision through which the endoscope 330 is advanced to visualize insertion of a first bone screw 320 may be later utilized for the insertion of a second bone screw 320. The endoscope 330 may then visualize the insertion of the second bone screw 320 from a third stab incision which is later utilized for insertion of a third bone screw, and so forth.

The invention claimed is:

1. A bone plating instrument comprising:
a handle sized to receive a palm of a hand of an orthopedic surgeon,
a tissue expander non-removably secured to the handle, the tissue expander comprising a body having a top wall and a pair of downwardly extending side walls, wherein (i) the top wall has an access hole defined therein, and (ii) the top wall and the side walls define a working space configured to receive a tip of an endoscope, and
a screw alignment jig having a first end portion thereof secured to the handle such that a second end portion thereof is spaced-apart from the tissue expander and extends outwardly away from the handle in a direction toward the access hole of the tissue expander, the second end portion of the screw alignment jig having a guide hole aligned with the access hole of the tissue expander.

2. The bone plating instrument of claim 1, wherein the top wall and the pair of downwardly extending side walls define a semi-tubular shaped structure.

3. The bone plating instrument of claim 1, wherein the top wall and the pair of downwardly extending side walls define a non-arcuate shaped structure.

4. The bone plating instrument of claim 1, wherein the body has a chamfered portion around the periphery of the access hole.

5. The bone plating instrument of claim 1, wherein:
the body has a boss defined therein, and
the access hole extends through the boss.

6. The bone plating instrument of claim 1, further comprising a flexible seal covering the access hole.

7. The bone plating instrument of claim 1, wherein the body defines an elongated tunnel structure.

8. The bone plating instrument of claim 1, wherein the screw alignment jig includes a plurality of guide holes and the top wall of the body of the tissue expander has a plurality of access holes defined therein which are positioned to align with the plurality of guide holes of the screw alignment jig.

9. The bone plating instrument of claim 1, wherein:
the body has a flange extending therefrom, and
the flange is configured to be received into an opening of a bone plate.

10. The bone plating instrument of claim 1, further comprising means for securing a bone plate to the tissue expander.

* * * * *

UNITED STATES PATENT AND TRADEMARK OFFICE
CERTIFICATE OF CORRECTION

| | | |
|---|---|---|
| PATENT NO. | : 8,328,808 B2 | Page 1 of 1 |
| APPLICATION NO. | : 10/480053 | |
| DATED | : December 11, 2012 | |
| INVENTOR(S) | : Guzman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,355 days.

Signed and Sealed this
Eleventh Day of November, 2014

Michelle K. Lee
*Deputy Director of the United States Patent and Trademark Office*